(12) United States Patent
Cooke et al.

(10) Patent No.: US 6,974,894 B2
(45) Date of Patent: Dec. 13, 2005

(54) PLANT STARCH COMPOSITION

(75) Inventors: David Cooke, Bedfordshire (GB); Martine Debet, Northampton (GB); Michael J. Gidley, Northamptonshire (GB); Stephen A. Jobling, Huntingdon (GB); Richard Safford, Bedfordshire (GB); Christopher M. Sidebottom, Bedfordshire (GB); Roger J. Westcott, Northamptonshire (GB)

(73) Assignee: National Starch and Chemical Company, Bridgewater, NJ (US)

( * ) Notice: Subject to any disclaimer, the term of this patent is extended or adjusted under 35 U.S.C. 154(b) by 268 days.

(21) Appl. No.: 10/056,454

(22) Filed: Jan. 24, 2002

(65) Prior Publication Data

US 2003/0166919 A1 Sep. 4, 2003

Related U.S. Application Data

(62) Division of application No. 08/945,722, filed as application No. PCT/GB96/01075 on May 3, 1996, now Pat. No. 6,825,342.

(30) Foreign Application Priority Data

May 5, 1995 (GB) ............................................. 9509229
Apr. 10, 1996 (GB) ............................................. 9607409

(51) Int. Cl.$^7$ ...................... C12N 15/82; C12N 15/29; C12N 5/10; A01H 5/00; C12P 19/04
(52) U.S. Cl. ...................... 800/284; 800/278; 800/286; 800/317.2; 800/317.4; 800/320; 800/320.1; 800/320.2; 800/320.3; 536/23.2; 536/23.6; 435/101; 435/320.1; 435/419
(58) Field of Search ................................ 800/278, 284, 800/286, 317.2, 320, 317.4, 320.1–320.3, 285; 536/23.2, 23.6, 24.5; 435/101, 320.1, 419, 417, 468

(56) References Cited

U.S. PATENT DOCUMENTS

| | | | |
|---|---|---|---|
| 3,887,752 | A | 6/1975 | Elizer |
| 4,608,265 | A | 8/1986 | Zweircan et al. |
| 5,344,663 | A | 9/1994 | Jewell et al. |
| 6,162,966 | A | 12/2000 | Kossmann et al. |
| 6,169,226 | B1 | 1/2001 | Ek et al. |
| 6,215,042 | B1 * | 4/2001 | Willmitzer et al. ......... 800/284 |

FOREIGN PATENT DOCUMENTS

| | | |
|---|---|---|
| CA | 2097218 | 10/1999 |
| JP | 6261767 | 9/1994 |
| WO | WO 90/12084 | 10/1990 |
| WO | WO 92/11375 | 7/1992 |
| WO | WO 92/11382 | 7/1992 |
| WO | WO 92/14827 | 9/1992 |
| WO | WO 94/24292 | 10/1994 |
| WO | WO 95/07355 | 3/1995 |
| WO | WO 95/26407 | 10/1995 |
| WO | WO 96/08261 | 3/1996 |
| WO | WO 96/19581 | 6/1996 |
| WO | WO 96/34968 | 11/1996 |
| WO | WO 97/20040 | 6/1997 |

OTHER PUBLICATIONS

Kossmann et al. 1995. pp. 271–278 In: Carbohydrate Bioengineering. Petersen et al, eds. Elsevier: Amsterdam.*
Blennow & Johnson, 1997 Phytochem. 30, 437–444.
Burton, et al., "Starch Branching Enzymes Belong to Distinct Enzyme Families are Differently Expressed During Pea Embryo Development", The Piany Journalm 7(1):3–15 (1995).
Flipse, Planta 198:340++ (1996).
Khoshnoodi etal., "Characterization of the 97 and 103 kDa forms of starch branching enzymes from potato tubers", Febs Letters 332:132–138.
Koβmann et al., 1991 Mol. Gen. Genet. 230, 39–44.
Koβmann et al., Macromol. Symp. 120, 29–38 (1997).
Krohn et al., "Modification of starch structure in transgenic potato" Plant Physiology 105(1):37 (1994).
Larsson et al., "Three isoforms of starch synthase and two isoforms of branching enzyme are present in potato tuber starch" Plant Science (Shannon) 117(1–2):9–16 (1996).
Matzke & Matzke 1995 Plant Physiology 107, 679–685.
Mizuno et al., "Alteration of the structural properties of starch components by the lack of an isoform of starch branching enzyme in rice seeds" J.Biol. Chem. 268(25):19084–91 (1993).
Muller–Robert & Koβmann 1994 Plant Cell and Environment 17, 601–613.
Sheehy et al. 1988 PNAS 85, 8805–8809.
Takaha et al., J. Biol. Chem. 268(2):1391–1396 (1993).
van der Krol et al., Mol. Gen. Genet. 220, 204–212.
van der Leij et al., "Expression of the gene encoding granule bound starch synthase after introduction in an amylose–free and wildtype potato" Abstracts VIIth International Congress on Plant Tissue and Cell Culture, Amsterdam, Jun. 24–29, No. A5–28, pp. 177 (1990).
Visser et al., Inhibition of the expression of the gene for granule–bound starch synthase in potato antisense constructs: Mol. Gen. Genet. 225:289–296 (1991).
Willmitzer et al., "Starch synthesis in transgenic plants", Plant Polymeric Carbohydrates, International Symposium held in Berlin, Jul. 1–3 1993, pp. 33–39.

* cited by examiner

*Primary Examiner*—David T. Fox
(74) *Attorney, Agent, or Firm*—Morgan, Lewis & Bockius LLP

(57) ABSTRACT

Disclosed is a nucleotide sequence encoding an effective portion of a class A starch branching enzyme (SBE) obtainable from potato plants, or a functional equivalent thereof, together with, inter alia, a corresponding polypeptide, a method of altering the characteristics of a plant, a plant having altered characteristics; and starch, particularly starch obtained from a potato plant, having novel properties.

34 Claims, 75 Drawing Sheets

Fig. 4a SHEET 1

Fig. 4a SHEET 2

```
Majority  D E X X S E - R - - - - - - - - - - - - - - - - - - - - - - - - - - - - - - - - - - - - - - - - - - - - -

E                                                                                                         800
maize 2   E G V E P I E L S                                                                                             856
pea 1     D A G R R L H A K A E T G K T S P A E S I D V K A S R A S S K                                                 824
maize 1   D C D R E L R G G                                                                                             769
rice 1    D R M T E D Y Q                                                                                               789
potato1   D L P N                                                                                                       703
human E D K E A T A G G K K G W K F A R Q P S D Q D T K - - - - - - - - - - - - - - - - - - - - - - - - - - -
```

Fig. 4a SHEET 3

Fig. 4b

```
TTGATGGGGCCTTGAACTCAGCAATTTGACACTCAGTTAGTTACA
AACTACCCCGGAACTTGAGTCGTTAAACTGTGAGTCAATCAATGT

AAGGAATGAATAAAAGGATAGATTTGTAAAAACCCTAAGGAGAGA
TTCCTTACTTATTTTCCTATCTAAACATTTTGGGATTCCTCTCT
    M  N  K  R  I  D  L

GTTCCATCAGTGTACAAATCAATGGATTCAGCAGTAATGGTGAT
CAAGGTAGTCACATGTTTAGATTACCTAAGTCGTCATTACCACTA
 V  P  S  V  Y  K  S  N  G  F  S  S  N  G  D

Bgl II                              EcoR I
TCACGGAAGATCTTGGCTGAAAAGTCTTCTTACAATTCCGAATTC
AGTGCCTTCTAGAACCGACTTTTCAGAAGAATGTTAAGGCTTAAG
  S  R  K  I  L  A  E  K  S  S  Y  N  S  E  F

ACCCAGAGTGATAGCTCCTCATCCTCAACAGACCAATTTGAGTTC
TGGGTCTCACTATCGAGGAGTAGGAGTTGTCTGGTTAAACTCAAG
  T  Q  S  D  S  S  S  S  T  D  Q  F  E  F

AGTTCAACAATGGAACACGCTAGCCAGATTAAAACTGAGAACGAT
TCAAGTTGTTACCTTGTGCGATCGGTCTAATTTTGACTCTTGCTA
  S  S  T  M  E  H  A  S  Q  I  K  T  E  N  D

GATTTTGCTTCATCACTACAACTACAAGAAGGTGGTAAACTGGAG
CTAAAACGAAGTAGTGATGTTGATGTTCTTCCACCATTTGACCTC
  D  F  A  S  S  L  Q  L  Q  E  G  G  K  L  E
```

Fig. 5 Sheet 2

Fig. 5 SHEET 1

```
                    Bgl II
CTCCTATCACTTATCAGATCTCTATTTTTCTCTTAATTCCAACC
----+----+----+----+----+----+----+----+----+  90
GAGGATAGTGAATAGTCTAGAGATAAAAAGAGAATTAAGGTTGG

AGAAGAAAGATGGTGTATACACTCTCTGGAGTTCGTTTTCCTACT
----+----+----+----+----+----+----+----+----+  180
TCTTCTTTCTACCACATATGTGAGAGACCTCAAGCAAAAGGATGA
        M  V  Y  T  L  S  G  V  R  F  P  T

CGGAGGAATGCTAATGTTTCTGTATTCTTGAAAAAGCACTCTCTT
----+----+----+----+----+----+----+----+----+  270
GCCTCCTTACGATTACAAAGACATAAGAACTTTTTCGTGAGAGAA
 R  R  N  A  N  V  S  V  F  L  K  K  H  S  L

CGACCTTCTACAGTTGCAGCATCGGGGAAAGTCCTTGTGCCTGGA
----+----+----+----+----+----+----+----+----+  360
GCTGGAAGATGTCAACGTCGTAGCCCCTTTCAGGAACACGGACCT
 R  P  S  T  V  A  A  S  G  K  V  L  V  P  G

ACTGAGACATCTCCAGAAAATTCCCCAGCATCAACTGATGTAGAT
----+----+----+----+----+----+----+----+----+  450
TGACTCTGTAGAGGTCTTTTAAGGGGTCGTAGTTGACTACATCTA
 T  E  T  S  P  E  N  S  P  A  S  T  D  V  D

GACGTTGAGCCGTCAAGTGATCTTACAGGAAGTGTTGAAGAGCTG
----+----+----+----+----+----+----+----+----+  540
CTGCAACTCGGCAGTTCACTAGAATGTCCTTCACAACTTCTCGAC
 D  V  E  P  S  S  D  L  T  G  S  V  E  E  L

GAGTCTAAAACATTAAATACTTCTGAAGAGACAATTATTGATGAA
----+----+----+----+----+----+----+----+----+  630
CTCAGATTTTGTAATTTATGAAGACTTCTCTGTTAATAACTACTT
 E  S  K  T  L  N  T  S  E  E  T  I  I  D  E
```

Fig 5 SHEET 2

```
TCTGATAGGATCAGAGAGAGGGGCATCCCTCCACCTGGACTTGGT
AGACTATCCTAGTCTCTCTCCCCGTAGGGAGGTGGACCTGAACCA
 S   D   R   I   R   E   R   G   I   P   P   P   G   L   G

CACCTTGATTACAGGTATTCACAGTACAAGAAACTGAGGGAGGCA
GTGGAACTAATGTCCATAAGTGTCATGTTCTTTGACTCCCTCCGT
 H   L   D   Y   R   Y   S   Q   Y   K   K   L   R   E   A

GAAAAAATGGGTTTCACTCGTAGTGCTACAGGTATCACTTACCGT
CTTTTTTACCCAAAGTGAGCATCACGATGTCCATAGTGAATGGCA
 E   K   M   G   F   T   R   S   A   T   G   I   T   Y   R

AACAATTGGGACGCAAATGCTGACATTATGACTCGGAATGAATTT
TTGTTAACCCTGCGTTTACGACTGTAATACTGAGCCTTACTTAAA
 N   N   W   D   A   N   A   D   I   M   T   R   N   E   F

GCAATTCCTCATGGGTCCAGAGTGAAGATACGTATGGACACTCCA
CGTTAAGGAGTACCCAGGTCTCACTTCTATGCATACCTGTGAGGT
 A   I   P   H   G   S   R   V   K   I   R   M   D   T   P
```

Fig. 5 Sheet 4

Fig. 5 SHEET 3

```
                                                       Hinc II
CAGAAGATTTATGAAATAGACCCCCTTTTGACAAACTATCGTCAA
---+----+----+----+----+----+----+----+----+ 720
GTCTTCTAAATACTTTATCTGGGGGAAAACTGTTTGATAGCAGTT
  Q   K   I   Y   E   I   D   P   L   L   T   N   Y   R   Q ATTGACAAGTATGAGGGTGGTTTGGAAGCCTTTTCTCGTGGTTAT
---+----+----+----+----+----+----+----+----+ 810
TAACTGTTCATACTCCCACCAAACCTTCGGAAAAGAGCACCAATA
  I   D   K   Y   E   G   G   L   E   A   F   S   R   G   Y Pvu II
GAGTGGGCTCTTGGTGCCCAGTCAGCTGCCCTCATTGGAGATTTC
---+----+----+----+----+----+----+----+----+ 900
CTCACCCGAGAACCACGGGTCAGTCGACGGGAGTAACCTCTAAAG
  E   W   A   L   G   A   Q   S   A   A   L   I   G   D   F GGTGTCTGGGAGATTTTTCTGCCAAATAATGTGGATGGTTCTCCT
---+----+----+----+----+----+----+----+----+ 990
CCACAGACCCTCTAAAAAGACGGTTTATTACACCTACCAAGAGGA
  G   V   W   E   I   F   L   P   N   N   V   D   G   S   P TCAGGTGTTAAGGATTCCATTCCTGCTTGGATCAACTACTCTTTA
---+----+----+----+----+----+----+----+----+ 1080
AGTCCACAATTCCTAAGGTAAGGACGAACCTAGTTGATGAGAAAT
  S   G   V   K   D   S   I   P   A   W   I   N   Y   S   L
```

Fig. 5 SHEET 4

```
CAGCTTCCTGATGAAATTCCATATAATGGAATACATTATGATCCA
GTCGAAGGACTACTTTAAGGTATATTACCTTATGTAATACTAGGT
 Q  L  P  D  E  I  P  Y  N  G  I  H  Y  D  P

CCAAAGTCGCTGAGAATATATGAATCTCATATTGGAATGAGTAGT
GGTTTCAGCGACTCTTATATACTTAGAGTATAACCTTACTCATCA
 P  K  S  L  R  I  Y  E  S  H  I  G  M  S  S

HinD III
CTTCCTCGCATAAAAAAGCTTGGGTACAATGCGCTGCAAATTATG
GAAGGAGCGTATTTTTTCGAACCCATGTTACGCGACGTTTAATAC
 L  P  R  I  K  K  L  G  Y  N  A  L  Q  I  M

ACAAATTTTTTTGCACCAAGCAGCCGTTTTGGAACGCCCGACGAC
TGTTTAAAAAAACGTGGTTCGTCGGCAAAACCTTGCGGGCTGCTG
 T  N  F  F  A  P  S  S  R  F  G  T  P  D  D

CTCATGGACATTGTTCACAGCCATGCATCAAATAATACTTTAGAT
GAGTACCTGTAACAAGTGTCGGTACGTAGTTTATTATGAAATCTA
 L  M  D  I  V  H  S  H  A  S  N  N  T  L  D
```

Fig. 5 Sheet 6

Fig. 5 SHEET 5

```
CCCGAAGAGGAGAGGTATATCTTCCAACACCCACGGCCAAAGAAA
--------+--------+--------+--------+--------+ 1170
GGGCTTCTCCTCTCCATATAGAAGGTTGTGGGTGCCGGTTTCTTT
  P  E  E  E  R  Y  I  F  Q  H  P  R  P  K  K
```

```
                                        Xmn I
CCGGAGCCTAAAATTAACTCATACGTGAATTTTAGAGATGAAGTT
--------+--------+--------+--------+--------+ 1260
GGCCTCGGATTTTAATTGAGTATGCACTTAAAATCTCTACTTCAA
  P  E  P  K  I  N  S  Y  V  N  F  R  D  E  V
```

```
GCTATTCAAGAGCATTCTTATTACGCTAGTTTTGGTTATCATGTC
--------+--------+--------+--------+--------+ 1350
CGATAAGTTCTCGTAAGAATAATGCGATCAAAACCAATAGTACAG
  A  I  Q  E  H  S  Y  Y  A  S  F  G  Y  H  V
```

```
CTTAAGTCTTTGATTGATAAAGCTCATGAGCTAGGAATTGTTGTT
--------+--------+--------+--------+--------+ 1440
GAATTCAGAAACTAACTATTTCGAGTACTCGATCCTTAACAACAA
  L  K  S  L  I  D  K  A  H  E  L  G  I  V  V
```

```
GGACTGAACATGTTTGACTGCACCGATAGTTGTTACTTTCACTCT
--------+--------+--------+--------+--------+ 1530
CCTGACTTGTACAAACTGACGTGGCTATCAACAATGAAAGTGAGA
  G  L  N  M  F  D  C  T  D  S  C  Y  F  H  S
```

Fig. 5 SHEET 6

Sac I

```
GGAGCTCGTGGTTATCATTGGATGTGGGATTCCCGCCTCTTTAAC
CCTCGAGCACCAATAGTAACCTACACCCTAAGGGCGGAGAAATTG
 G  A  R  G  Y  H  W  M  W  D  S  R  L  F  N

TGGTGGTTGGATGCGTTCAAATTTGATGGATTTAGATTTGATGGT
ACCACCAACCTACGCAAGTTTAAACTACCTAAATCTAAACTACCA
 W  W  L  D  A  F  K  F  D  G  F  R  F  D  G

ACTGGGAACTACGAGGAATACTTTGGACTCGCAACTGATGTGGAT
TGACCCTTGATGCTCCTTATGAAACCTGAGCGTTGACTACACCTA
 T  G  N  Y  E  E  Y  F  G  L  A  T  D  V  D

TTCCCAGATGCAATTACCATTGGTGAAGATGTTAGCGGAATGCCG
AAGGGTCTACGTTAATGGTAACCACTTCTACAATCGCCTTACGGC
 F  P  D  A  I  T  I  G  E  D  V  S  G  M  P

CGGCTGCATATGGCAATTGCTGATAAACGGATTGAGTTGCTCAAG
GCCGACGTATACCGTTAACGACTATTTGCCTAACTCAACGAGTTC
 R  L  H  M  A  I  A  D  K  R  I  E  L  L  K

ACAAATAGAAGATGGTCGGAAAAGTGTGTTTCATACGCTGAAAGT
TGTTTATCTTCTACCAGCCTTTTCACACAAAGTATGCGACTTTCA
 T  N  R  R  W  S  E  K  C  V  S  Y  A  E  S
```

Fig 5 Sheet 8

Fig. 5 SHEET 7

```
TATGGAAACTGGGAGGTACTTAGGTATCTTCTCTCAAATGCGAGA
—+————+————+————+————+————+————+————+————+————+  1620
ATACCTTTGACCCTCCATGAATCCATAGAAGAGAGTTTACGCTCT
 Y  G  N  W  E  V  L  R  Y  L  L  S  N  A  R

GTGACATCAATGATGTATATTCACCACGGATTATCGGTGGGATTC
—+————+————+————+————+————+————+————+————+————+  1710
CACTGTAGTTACTACATATAAGTGGTGCCTAATAGCCACCCTAAG
 V  T  S  M  M  Y  I  H  H  G  L  S  V  G  F
```

Hinc II
```
GCTGTTGTGTATCTGATGCTGGTCAACGATCTTATTCATGGGCTT
—+————+————+————+————+————+————+————+————+————+  1800
CGACAACACATAGACTACGACCAGTTGCTAGAATAAGTACCCGAA
 A  V  V  Y  L  M  L  V  N  D  L  I  H  G  L ACATTTGTATTCCCGTCCAAGAGGGGGGTGTTGGCTTTGACTAT
—+————+————+————+————+————+————+————+————+————+  1890
TGTAAAACATAAGGGCAGGTTCTCCCCCCACAACCGAAACTGATA
 T  F  C  I  P  V  Q  E  G  G  V  G  F  D  Y AAACGGGATGAGGATTGGAGAGTGGGTGATATTGTTCATACACTG
—+————+————+————+————+————+————+————+————+————+  1980
TTTGCCCTACTCCTAACCTCTCACCCACTATAACAAGTATGTGAC
 K  R  D  E  D  W  R  V  G  D  I  V  H  T  L CATGATCAAGCTCTAGTCGGTGATAAAACTATAGCATTCTGGCTG
—+————+————+————+————+————+————+————+————+————+  2070
GTACTAGTTCGAGATCAGCCACTATTTTGATATCGTAAGACCGAC
 H  D  Q  A  L  V  G  D  K  T  I  A  F  W  L
```

Fig. 5 SHEET 8

```
                                                           Hinc II
ATGGACAAGGATATGTATGATTTTATGGCTCTGGATAGACCGTCA
─┼────┼────┼────┼────┼────┼────┼────┼────┼────┼─
TACCTGTTCCTATACATACTAAAATACCGAGACCTATCTGGCAGT
 M  D  K  D  M  Y  D  F  M  A  L  D  R  P  S Asp 718
                                  Kpn I
CTTGTAACTATGGGATTAGGAGGAGAAGGGTACCTAAATTTCATG
─┼────┼────┼────┼────┼────┼────┼────┼────┼────┼─
GAACATTGATACCCTAATCCTCCTCTTCCCATGGATTTAAAGTAC
 L  V  T  M  G  L  G  G  E  G  Y  L  N  F  M GAACAACACCTCTCTGATGGCTCAGTAATCCCCGGAAACCAATTC
─┼────┼────┼────┼────┼────┼────┼────┼────┼────┼─
CTTGTTGTGGAGAGACTACCGAGTCATTAGGGGCCTTTGGTTAAG
 E  Q  H  L  S  D  G  S  V  I  P  G  N  Q  F Ssp I
TATTTAAGATACCGTGGGTTGCAAGAATTTGACCGGCCTATGCAG
─┼────┼────┼────┼────┼────┼────┼────┼────┼────┼─
ATAAATTCTATGGCACCCAACGTTCTTAAACTGGCCGGATACGTC
 Y  L  R  Y  R  G  L  Q  E  F  D  R  P  M  Q ATATCACGAAAGGATGAAGGAGATAGGATGATTGTATTTGAAAAA
─┼────┼────┼────┼────┼────┼────┼────┼────┼────┼─
TATAGTGCTTTCCTACTTCCTCTATCCTACTAACATAAACTTTTT
 I  S  R  K  D  E  G  D  R  M  I  V  F  E  K TCAGACTATCGCATAGCCTGCCTGAAGCCTGGAAAATACAAGGTT
─┼────┼────┼────┼────┼────┼────┼────┼────┼────┼─
AGTCTGATAGCGTATCGGACGGACTTCGGACCTTTTATGTTCCAA
 S  D  Y  R  I  A  C  L  K  P  G  K  Y  K  V
```

Fig. 5 SHEET 9

```
ACATCATTAATAGATCGTGGGATAGCATTGCACAAGATGATTAGG
                                                       2160
TGTAGTAATTATCTAGCACCCTATCGTAACGTGTTCTACTAATCC
  T  S  L  I  D  R  G  I  A  L  H  K  M  I  R

EcoR I
GGAAATGAATTCGGCCACCCTGAGTGGATTGATTTCCCTAGGGCT
                                                       2250
CCTTTACTTAAGCCGGTGGGACTCACCTAACTAAAGGGATCCCGA
  G  N  E  F  G  H  P  E  W  I  D  F  P  R  A

AGTTATGATAAATGCAGACGGAGATTTGACCTGGGAGATGCAGAA
                                                       2340
TCAATACTATTTACGTCTGCCTCTAAACTGGACCCTCTACGTCTT
  S  Y  D  K  C  R  R  R  F  D  L  G  D  A  E

TATCTTGAAGATAAATATGAGTTTATGACTTCAGAACACCAGTTC
                                                       2430
ATAGAACTTCTATTTATACTCAAATACTGAAGTCTTGTGGTCAAG
  Y  L  E  D  K  Y  E  F  M  T  S  E  H  Q  F

GGAAACCTAGTTTTTGTCTTTAATTTTCACTGGACAAAAAGCTAT
                                                       2520
CCTTTGGATCAAAAACAGAAATTAAAAGTGACCTGTTTTTCGATA
  G  N  L  V  F  V  F  N  F  H  W  T  K  S  Y

GCCTTGGACTCAGATGATCCACTTTTTGGTGGCTTCGGGAGAATT
                                                       2610
CGGAACCTGAGTCTACTAGGTGAAAAACCACCGAAGCCCTCTTAA
  A  L  D  S  D  D  P  L  F  G  G  F  G  R  I
```

Fig. 5 SHEET 10

```
                         Ssp I
GATCATAATGCCGAATATTTCACCTTTGAAGGATGGTATGATGAT
CTAGTATTACGGCTTATAAAGTGGAAACTTCCTACCATACTACTA
 D   H   N   A   E   Y   F   T   F   E   G   W   Y   D   D

GTCTATGCACTAGTAGACAAGAAGAAGAAGAAGAAGAAGAAGAA
CAGATACGTGATCATCTGTTCTTCTTCTTCTTCTTCTTCTTCTT
 V   Y   A   L   V   D   K   E   E   E   E   E   E   E

TGAACGAACTTGTGATCGCGTTGAAAGATTTGAACGCTACATAGA
ACTTGCTTGAACACTAGCGCAACTTTCTAAACTTGCGATGTATCT

TCATGTGACACAAGGTTTGCAATTCTTTCCACTATTAGTAGTGCA
AGTACACTGTGTTCCAAACGTTAAGAAAGGTGATAATCATCACGT

EcoR I      Pst I
GATGAATTTATGTCGAATGCTGGGACGATCGAATTCCTGCAGGCC
CTACTTAAATACAGCTTACGACCCTGCTAGCTTAAGGACGTCCGG
```

Fig. 5 SHEET 11

```
CGTCCTCGTTCAATTATGGTGTATGCACCTTGTAAAACAGCAGTG
---+----+----+----+----+----+----+----+----+ 2700
GCAGGAGCAAGTTAATACCACATACGTGGAACATTTTGTCGTCAC
   R  P  R  S  I  M  V  Y  A  P  C  K  T  A  V

GAAGAAGAAGTAGCAGCAGTAGAAGAAGTAGTAGTAGAAGAAGAA
---+----+----+----+----+----+----+----+----+ 2790
CTTCTTCTTCATCGTCGTCATCTTCTTCATCATCATCTTCTTCTT
   E  E  E  V  A  A  V  E  E  V  V  E  E  E

Ssp I
GCTTCTTGACGTATCTGGCAATATTGCATCAGTCTTGGCGGAATT
---+----+----+----+----+----+----+----+----+ 2880
CGAAGAACTGCATAGACCGTTATAACGTAGTCAGAACCGCCTTAA

Cla I
ACGATATACGCAGAGATGAAGTGCTGAACAAACATATGTAAAATC
---+----+----+----+----+----+----+----+----+ 2970
TGCTATATGCGTCTCTACTTCACGACTTGTTTGTATACATTTTAG

GGGGGACCCCTTAGTTCT
---+----+----+--→ 3033
CCCCCTGGGGAATCAAGA
```

Fig. 5 SHEET 12

```
     ╭180        ╭190        ╭200        ╭210        ╭220
IYEIDPLLTNYRQHLDYRYSQYKKLREAIDKYEGGLEAFSRGYEKMGFTR
 :  ::DP L   Y :H:  .R .:Y .  :    I:KYEG  LE. F:: GY  K. GF. R
LLNLDPTLEPYLDHFRHRMKRYVDQKMLIEKYEGPLEEFAQGYLKFGFNR
     ╰100        ╰110        ╰120        ╰130        ╰140
     ╭230        ╭240        ╭250        ╭260        ╭270
SATGITYREWALGAQSAALIGDFNNWDANADIMTRNEFGVWEIFLPNNVD
 ...   I. YREWA : AQ. A. : IGDFN. W:::.::M.:::FGVW. I  :P:  VD
EDGCIVYREWAPAAQEAEVIGDFNGWNGSNHMMEKDQFGVWSIRIPD-VD
     ╰150        ╰160        ╰170        ╰180        ╰190
     ╭280        ╭290        ╭300        ╭310        ╭320
GSPAIPHGSRVKIRMDTPSGV-KDSIPAWINYSLQLPDEI--PYNGIHYD
 :. P. IPH. SRVK: R. .    :GV  D. IPAWI: Y:  . :..:   PY: G:.. D
SKPVIPHNSRVKFRFKHGNGVWVDRIPAWIKYATADATKFAAPYDGVYWD
     ╰200        ╰210        ╰220        ╰230        ╰240
     ╭330        ╭340        ╭350        ╭360        ╭370
PPEEERYIFQHPRPKKPKSLRIYESHIGMSSPEPKINSYVNFRDEVLPRI
PP . ERY  F:. PRP KP:: RIYE:H: GMSS:EP::NSY :F D: VLPRI
PPPSERYHFKYPRPPKPRAPRIYEAHVGMSSSEPRVNSYREFADDVLPRI
     ╰250        ╰260        ╰270        ╰280        ╰290
     ╭380        ╭390        ╭400        ╭410        ╭420
KKLGYNALQIMAIQEHSYYASFGYHVTNFFAPSSRFGTPDDLKSLIDKAH
K    YN::Q: MAI  EHSYY: SFGYHVTNFFA S: R: G. P: DLK  LIDKAH
KANNYNTVQLMAIMEHSYYGSFGYHVTNFFAVSNRYGNPEDLKYLIDKAH
     ╰300        ╰310        ╰320        ╰330        ╰340
     ╭430        ╭440        ╭450        ╭460        ╭470
ELGIVVLMDIVHSHASNNTLDGLNMFDC---TDSCYFHSGARGYHWMWDS
. LG:  VL: D: VHSHASNN. DGLN FD      ::.. YFH: G. RGYH : WDS
SLGLQVLVDVVHSHASNNVTDGLNGFDIGQGSQESYFHAGERGYHKLWDS
     ╰350        ╰360        ╰370        ╰380        ╰390
     ╭480        ╭490        ╭500        ╭510        ╭520
RLFNYGNWEVLRYLLSNARWWLDAFKFDGFRFDGVTSMMYIHHGLSVGFT
RLFNY: NWEVLR: LLSN RWWL:.::FDGFRFDG: TSM: Y: HHG:::GFT
RLFNYANWEVLRFLLSNLRWWLEEYNFDGFRFDGITSMLYVHHGINMGFT
     ╰400        ╰410        ╰420        ╰430        ╰440
     ╭530        ╭540        ╭550        ╭560        ╭570
GNYEEYFGLATDVDAVVYLMLVNDLIHGLFPDAITIGEDVSGMPTFCIPV
GNY: EYF:  ATDVDAVVYLML. N: LIH : FPDA. . I: EDVSGMP. :.  PV
GNYNEYFSEATDVDAVVYLMLANNLIHKIFPDATVIAEDVSGMPGLSRPV
     ╰450        ╰460        ╰470        ╰480        ╰490
     ╭580        ╭590        ╭600        ╭610        ╭620
QEGGVGFDYRLHMAIADKRIELLK-KRDEDWRVGDIVHTLTNRRWSEKCV
  EGG: GFDYRL  MAI: DK  I:  LK  K. DEDW. :   ::.. : LTNRR. : EKC:
SEGGIGFDYRLAMAIPDKWIDYLKNKNDEDWSMKEVTSSLTNRRYTEKCI
     ╰500        ╰510        ╰520        ╰530        ╰540
```

Fig. 6 SHEET 1

```
             ↓630        ↓640        ↓650        ↓660        ↓670
      SYAESHDQALVGDKTIAFWLMDKDMYDFMALDRPSTSLIDRGIALHKMIR
      :YAESHDQ::VGDKTIAF LMDK:MY. M:     :::::DRGIALHKMI:
      AYAESHDQSIVGDKTIAFLLMDKEMYSGMSCLTDASPVVDRGIALHKMIH
            ↑550        ↑560        ↑570        ↑580        ↑590
             ↓680        ↓690        ↓700        ↓710        ↓720
      LVTMGLGGEGYLNFMGNEFGHPEWIDFPRAEQHLSDGSVIPGNQFSYDKC
      : TM: LGGEGYLNFMGNEFGHPEWIDFPR           GN: . SYDKC
      FFTMALGGEGYLNFMGNEFGHPEWIDFPR----------EGNNWSYDKC
           ↑600        ↑610        ↑620                   ↑630
             ↓730        ↓740        ↓750        ↓760        ↓770
      RRRFDLGDAEYLRYRGLQEFDRPMQYLEDKYEFMTSEHQFISRKDEGDRM
      RR: . : L: D: E. LRY:  :: . FDR: M:  L:: K: . F:: S. . Q:: S. . D:::::
      RRQWNLADSEHLRYKFMNAFDRAMNSLDEKFSFLASGKQIVSSMDDDNKV
            ↑640        ↑650        ↑660        ↑670        ↑680
             ↓780        ↓790        ↓800        ↓810        ↓820
      IVFEKGNLVFVFNFHWTKSYSDYRIACLKPGKYKVALDSDDPLFGGFGRI
      : VFE: G: LVFVFNFH . :: Y. : Y::: C  PGKY: VAL: SD.   FGG GR
      VVFERGDLVFVFNFHPNNTYEGYKVGCDLPGKYRVALGSDAWEFGGHGRA
            ↑690        ↑700        ↑710        ↑720        ↑730
             ↓830        ↓840        ↓850        ↓860
      DHNAEYFT-------FEGWYDDRPRSIMVYAPCKTAVVYALVDKEEEEE
      : H: . : . FT            E.   :::RP. S:. V  :P  :T  V. Y    VD.    . E.
      GHDVDHFTSPEGIPGVPETNFNGRPNSFKVLSPARTCVAYYRVDERMSET
            ↑740        ↑750        ↑760        ↑770        ↑780
             ↓870
      EEEEEEV
      E:  : . ::
      EDYQTDI
            ↑790
```

Fig. 6 SHEET 2

```
         ↓10         ↓20         ↓30         ↓40
MVYTLSGVRFPTVPSVYKSNGFSSNGDRRNANVSVFLKKH--SLSRKILA
MVYT: SG: RFP. : PS: .KS  :  . DRR. : :  S FLK: :   S: SR.  L
MVYTISGIRFPVLPSLHKS---TLRCDRRASSHSFFLKNNSSSFSRTSLY
         ▲10         ▲20         ▲30         ▲40
    ↓50         ↓60         ↓70         ↓80         ↓90
EKSSYNSEFRPSTVAASGKVLVPGTQSDSSSSSTDQFEFTETSPENSPAS
. K S : SE : : ST: A. S: KVL: P. . Q D: S S : DQ: E . : : : E: : . .
AKFSRDSETKSSTIAESDKVLIPEDQ-DNSVSLADQLENPDITSEDAQNL
    ▲50         ▲60         ▲70         ▲80         ▲90
   ↓100        ↓110        ↓120        ↓130        ↓140
TDVDSSTMEHASQIKTENDDVEPSSDLTGSVEELDFASSLQLQEGGKLEE
. D:     TM. : : :   : .   :    . : : .   . . .   : S : : : : . : .   .
EDL---TMKDGNKYNID-ESTSSYREVGDEKGSVTSSSLVDVNTDTQ--A
    ▲100        ▲110        ▲120        ▲130        ▲140
   ↓150        ↓160        ↓170        ↓180        ↓190
SKTLNTSEETIIDESDRIRERGIPPPGLGQKIYEIDPLLTNYRQHLDYRY
. KT    S: . . :    : .    : I       IPPPG  GQKIYEIDPLL . . RQHLD: RY
KKTSVHSDKKVKVDKPKI----IPPPGSGQKIYEIDPLLQAHRQHLDFRY
    ▲150        ▲160        ▲170        ▲180
   ↓200        ↓210        ↓220        ↓230        ↓240
SQYKKLREAIDKYEGGLEAFSRGYEKMGFTRSATGITYREWALGAQSAAL
: QYK: : RE. IDKYEGGL: AFSRGYEK. GFTRSATGITYREW: GA: SAAL
GQYKRIREEIDKYEGGLDAFSRGYEKFGFTRSATGITYREWGPGAKSAAL
    ▲190        ▲200        ▲210        ▲220        ▲230
   ↓250        ↓260        ↓270        ↓280        ↓290
IGDFNNWDANADIMTRNEFGVWEIFLPNNVDGSPAIPHGSRVKIRMDTPS
: GDFNNW: : NAD: MT: : . FGVWEIFLPNN. DGSP: IPHGSRVKI: MDTPS
VGDFNNWNPNADVMTKDAFGVWEIFLPNNADGSPPIPHGSRVKIHMDTPS
    ▲240        ▲250        ▲260        ▲270        ▲280
   ↓300        ↓310        ↓320        ↓330        ↓340
GVKDSIPAWINYSLQLPDEIPYNGIHYDPPEEERYIFQHPRPKKPKSLRI
G: KDSIPAWI: : S: Q P: EIPYNGI. YDPPEEE: Y: F: HP: PK: P: S: RI
GIKDSIPAWIKFSVQAPGEIPYNGIYYDPPEEEKYVFKHPQPKRPQSIRI
    ▲290        ▲300        ▲310        ▲320        ▲330
   ↓350        ↓360        ↓370        ↓380        ↓390
YESHIGMSSPEPKINSYVNFRDEVLPRIKKLGYNALQIMAIQEHSYYASF
YESHIGMSSPEPKIN: Y. NFRD: VLPRIKKLGYNA: QIMAIQEHSYYASF
YESHIGMSSPEPKINTYANFRDDVLPRIKKLGYNAVQIMAIQEHSYYASF
    ▲340        ▲350        ▲360        ▲370        ▲380
   ↓400        ↓410        ↓420        ↓430        ↓440
GYHVTNFFAPSSRFGTPDDLKSLIDKAHELGIVVLMDIVHSHASNNTLDG
GYHVTNFFAPSSRFGTP: DLKSLID: AHELG: : VLMDIVHSH: SNNTLDG
GYHVTNFFAPSSRFGTPEDLKSLIDRAHELGLLVLMDIVHSHSSNNTLDG
    ▲390        ▲400        ▲410        ▲420        ▲430
```

Fig. 7 SHEET 1

```
     ₋450       ₋460       ₋470       ₋480       ₋490
LNMFDCTDSCYFHSGARGYHWMWDSRLFNYGNWEVLRYLLSNARWWLDAF
LNMFD TD: YFH: G: RGYHWMWDSRLFNYG: WEVLRYLLSNARWWLD. :
LNMFDGTDGHYFHPGSRGYHWMWDSRLFNYGSWEVLRYLLSNARWWLDEY
     ᴸ440       ᴸ450       ᴸ460       ᴸ470       ᴸ480
     ₋500       ₋510       ₋520       ₋530       ₋540
KFDGFRFDGVTSMMYIHHGLSVGFTGNYEEYFGLATDVDAVVYLMLVNDL
KFDGFRFDGVTSMMY. HHGL V: FTGNY. EYFGLATDV: AVVY: MLVNDL
KFDGFRFDGVTSMMYTHHGLQVSFTGNYSEYFGLATDVEAVVYMMLVNDL
     ᴸ490       ᴸ500       ᴸ510       ᴸ520       ᴸ530
     ₋550       ₋560       ₋570       ₋580       ₋590
IHGLFPDAITIGEDVSGMPTFCIPVQEGGVGFDYRLHMAIADKRIELLKK
IHGLFP: A: : IGEDVSGMPTFC: P. Q: GG: GF: YRLHMA: ADK: IELLKK
IHGLFPEAVSIGEDVSGMPTFCLPTQDGGIGFNYRLHMAVADKWIELLKK
     ᴸ540       ᴸ550       ᴸ560       ᴸ570       ᴸ580
     ₋600       ₋610       ₋620       ₋630       ₋640
RDEDWRVGDIVHTLTNRRWSEKCVSYAESHDQALVGDKTIAFWLMDKDMY
: DEDWR: GDIVHTLTNRRW EKCV YAESHDQALVGDKT: AFWLMDKDMY
QDEDWRMGDIVHTLTNRRWLEKCVVYAESHDQALVGDKTLAFWLMDKDMY
     ᴸ590       ᴸ600       ᴸ610       ᴸ620       ᴸ630
     ₋650       ₋660       ₋670       ₋680       ₋690
DFMALDRPSTSLIDRGIALHKMIRLVTMGLGGEGYLNFMGNEFGHPEWID
DFMALDRPST: LIDRGIALHKMIRL: TMGLGGEGYLNFMGNEFGHPEWID
DFMALDRPSTPLIDRGIALHKMIRLITMGLGGEGYLNFMGNEFGHPEWID
     ᴸ640       ᴸ650       ᴸ660       ᴸ670       ᴸ680
     ₋700       ₋710       ₋720       ₋730       ₋740
FPRAEQHLSDGSVIPGNQFSYDKCRRRFDLGDAEYLRYRGLQEFDRPMQY
FPR: EQHL: : G. : : PGN: SYDKCRRRFDLGDA: YLRY: G: QEFDR: MQ.
FPRGEQHLPNGKIVPGNNNSYDKCRRRFDLGDADYLRYHGMQEFDRAMQH
     ᴸ690       ᴸ700       ᴸ710       ᴸ720       ᴸ730
     ₋750       ₋760       ₋770       ₋780       ₋790
LEDKYEFMTSEHQFISRKDEGDRMIVFEKGNLVFVFNFHWTKSYSDYRIA
LE: . Y. FMTSEHQ: ISRK: EGDR: I: FE: : NLVFVFNFHWT: SYSDY: : :
LEETYGFMTSEHQYISRKNEGDRVIIFERDNLVFVFNFHWTNSYSDYKVG
     ᴸ740       ᴸ750       ᴸ760       ᴸ770       ᴸ780
     ₋800       ₋810       ₋820       ₋830       ₋840
CLKPGKYKVALDSDDPLFGGFGRIDHNAEYFTFEGWYDDRPRSIMVYAPC
CLKPGKYK: . LDSDD. LFGGF. R: : H. AEYFT EGWYDDRPRS: : VYAP.
CLKPGKYKIVLDSDDTLFGGFNRLNHTAEYFTSEGWYDDRPRSFLVYAPS
     ᴸ790       ᴸ800       ᴸ810       ᴸ820       ᴸ830
     ₋850       ₋860       ₋870
KTAVVYALVDKEEEEEEEEEEEVAA
: TAVVYAL. D  E. E   E . : . V. :
RTAVVYALADGVESEPIELSDGVES
     ᴸ840       ᴸ850       ᴸ860
```

Fig. 7 SHEET 2

```
  1    -----------------TTG--AT-----------
  1    -----------------TTGA-------------
  1    ---------------GA----------------
 45    AAAAACCTCCTCCACTCAGTCTTGGCATCTCTCTCTCT

72    TTTCTCTTAATTCCAACCAGGCGAATGAATAAAAGGAT-A
 73    TTTCTCTTAATTCCAACCAAGG-AATGAATAAAAGGAT-A
 71    TTTCTCTTAATTCCAACCAAGG-AATGAATAAAAGAT-A
165    TTTCTCTTAATTCCAACCAAGG-AATGAATAAAAGATTA

191    TGTACAAATCTAATGGATTCAGCAGTAATGGTGATCGGAG
191    TGTACAAATCTAATGGATTCAGCAGTAATGGTGATCGGAG
189    TGTACAAATCTAATGGATTCAGCAGTAATGGTGATCGGAG
274    TGTACAAATCTAATGGATTCAGCAGTAATGGTGATCGGAG

311    AATTCCGACCTTCTACAGTTGCAGCATCGGGGAAAGTCCT
311    AATTCCGACCTTCTACAGTTGCAGCATCGGGGAAAGTCCT
309    AATCCCGACCTTCTACAATTGCAGCATCGGGGAAAGTCCT
394    AATCCCGACCTTCTACAGTTGCAGCATCGGGGAAAGTCCT

431    CAGCATCAACTGATGTAGATAGTTCAACAATGGAACACGC
431    CAGCATCAACTGATGTAGATAGTTCAACAATGGAACACGC
429    CAGCATCAACTGATGTAGATAGTTCAACAATGGAACACGC
514    CAGCATCAACTGATGTCGATAGTTCAACAATGGAACACGC

551    CATCACTACAACTACAAGAAGGTGGTAAACTGGAGGAGTC
551    CATCACTACAACTACAAGAAGGTGGTAAACTGGAGGAGTC
549    CATCACTACAACTACAAGAAGGTGGTAAACTGGAGGAGTC
634    CATCACTACAACTACAAGAAGGTGGTAAACTGGAGGAGTC

671    TTGGTCAGAAGATTTATGAAATAGACCCCCTTTTGACAAA
671    TTGGTCAGAAGATTTATGAAATAGACCCCCTTTTGACAAA
669    TTGGTCAGAAGATTTATGAAATAGACCCCCTTTTGACAAA
754    TTGGTCAGAAGATTTATGAAATAGACCCCCTTTTGACAAA

791    AAGCTTTTTCTCGTGGTTATGAAAAAATGGGTTTCACTCG
791    AAGCCTTTTCTCGTGGTTATGAAAAAATGGGTTTCACTCG
789    AAGCTTTTTCTCGTGGTTATGAAACAATGGGTTTCACTCG
874    AAGCTTTTTCTCGTGGTTATGAAAAAATGGGTTTCACTCG
```

Fig. 8 Sheet 2

Fig. 8 SHEET 1

```
----------- -GGGCCTTGAACTCAGCAATTTGACACTCAGTTAGTTAC
------------TGGGGCCTTGAACTCAGCAATTTGACACTCAGTTAGTTAC
------------TGGGGCCTTGAACTCAGCAATTTGACACTCAGTTAGTTAC
TCACGCTTCTCTTGGGGCCTTGAACTCAGCAATTTGACACTCAGTTAGTTAC

GATTTGTAAAAACCCTAAGGAGAGAAGAAGAAAGATGGTGTATATACTCTCT
GATTTGTAAAAACCCTAAGGAGAGAAGAAGAAAGATGGTGTATACACTCTCT
GATTTGTAAAAACCCTAAGGAGAGAAGAAGAAAGATGGTGTATACACTCTCT
GATTTG-----------AAGGAGAGAAGAAGAAAGATGGTGTATACACTCTCT

GAATGCTAATGTTTCTGTATTCTTGAAAAAGCACTCTCTTTCACGGAAGATC
GAATGCTAATGTTTCTGTATTCTTGAAAAAGCACTCTCTTTCACGGAAGATC
GAATGCTAATATTTCTGTATTCTTGAAAAACACTCTCTTTCACGGAAGATC
GAATGCTAATGTTTCTGTATTCTTGAAAAAGCACTCTCTTTCACGGAAGATC

TGTGCCTGGAACCCAGAGTGATAGCTCCTCATCCTCAACAGACCAATTTGAG
TGTGCCTGGAACCCAGAGTGATAGCTCCTCATCCTCAACAGACCAATTTGAG
TGTGCCTGGAATCCAGAGTGATAGCTCCTCATCCTCAACAGATCAATTTGAG
TGTACCTGGAATCCAGAGTGATAGCTCCTCATCCTCAACAGACCAATTTGAG

TAGCCAGATTAAAACTGAGAACGATGACGTTGAGCCGTCAAGTGATCTTACA
TAGCCAGATTAAAACTGAGAACGATGACGTTGAGCCGTCAAGTGATCTTACA
TAGCCAGATTAAAACTGAGAACGATGACGTTGAGCCGTCAAGTGATCTTACA
TAGCCAGATTAAAACTGAGAACGATGACGTTGAGCCGTCAAGTGATCTTACA

TAAAACATTAAATACTTCTGAAGAGACAATTATTGATGAATCTGATAGGATC
TAAAACATTAAATACTTCTGAAGAGACAATTATTGATGAATCTGATAGGATC
TAAAACATTAAATACTTCTGAAGAGACAATTATTGATGAATCTGATAGGATC
TAAAACATTAAATACTTCTGAAGAGACAATTATTGATGAATCTGATAGGATC

CTATCGTCAACACCTTGATTACAGGTATTCACAGTACAAGAAACTGAGGGAG
CTATCGTCAACACCTTGATTACAGGTATTCACAGTACAAGAAACTGAGGGAG
CTATCGTCAACACCTTGATTACAGGTATTCACAGTACAAGAAACTGAGGGAG
CTATCGTCAACACCTTGATTACAGGTATTCACAGTACAAGAAATGAGGGAG

TAGTGCTACAGGTATCACTTACCGTGAGTGGGCTCCTGGTGCCCAGTCAGCT
TAGTGCTACAGGTATCACTTACCGTGAGTGGGCTCTTGGTGCCCAGTCAGCT
TAGTGCTACAGGTATCACTTACCGTGAGTGGGCTCCTGGTGCCCAGTCAGCT
TAGTGCTACAGGTATCACTTACCGTGAGTGGGCTCCTGGTGCCCAGTCAGCT
```

Fig. 8 Sheet 3

```
ACTCCTATCACTTATCAGATCTCTATTT 11con.seq
ACTCCTATCACTTATCAGATCTCTATTT 19con.seq
ACTGCCATCACTTATCAGATCTCTATTT 10con.seq
ACTCCTATCACTCATCAGATCTCTATTT psbe2con.seq GGAGTTCGTTTTCCTACTGTTCCATCAG 11con.seq
GGAGTTCGTTTTCCTACTGTTCCATCAG 19con.seq
GGAGTTCGTTTTCCTACTGTTCCATCAG 10con.seq
GGAGTTCGTTTTCCTACTGTTCCATCAG psbe2con.seq TTGGCTGAAAAGTCTTCTTACAATTCCG 11con.seq
TTGGCTGAAAAGTCTTCTTACAATTCCG 19con.seq
TTGGCTGAAAAGTCTTCTTACAATTCCG 10con.seq
TTGGCTGAAAAGTCTTCTTACCATTCCG psbe2con.seq TTCACTGAGACATCTCCAGAAAATTCCC 11con.seq
TTCACTGAGACATCTCCAGAAAATTCCC 19con.seq
TTCGCTGAGACATCTCCAGAAAATTCCC 10con.seq
TTCACTGAGACAGCTCCAGAAAATTCCC psbe2con.seq GGAAGTGTTGAAGAGCTGGATTTTGCTT 11con.seq
GGAAGTGTTGAAGAGCTGGATTTTGCTT 19con.seq
GGAAGTGTTGAAGAGCTGGATTTTGCTT 10con.seq
GGAAGTGTTGAAGAGTTGGATTTTGCTT psbe2con.seq AGAGAGAGGGGCATCCCTCCACCTGGAC 11con.seq
AGAGAGAGGGGCATCCCTCCACCTGGAC 19con.seq
AGAGAGAGGGGCATCCCTCCACCTGGAC 10con.seq
AGAGAGAGGGGCATCCCTCCACCTGGAC psbe2con.seq GCAATTGACAAGTATGAGGGTGGTTTGG 11con.seq
GCAATTGACAAGTATGAGGGTGGTTTGG 19con.seq
GCAATTGACAAGTATGAGGGTGGTTTGG 10con.seq
GCAATTGACAAGTATGAGGGTGGTTTGG psbe2con.seq GCCCTCATTGGAGATTTCAACAATTGGG 11con.seq
GCCCTCATTGGAGATTTCAACAATTGGG 19con.seq
GCCCTCATTGCCGATTTCAACAATTGGG 10con.seq
GCTCTCATTGGAGATTTCAACAATTGGG psbe2con.seq
```

Fig. 8
SHEET 3

```
910  ACGCAAATGCTGACATTATGACTCGGAATGAATTTGGTGTC
911  ACGCAAATGCTGACATTATGACTCGGAATGAATTTGGTGTC
909  ACGCAAATGCTGACTTTATGACTCGGAATGAATTTGGTGTC
994  ACGCAAATGCTGACATTATGACTCGGAATGAATTTGGTGTC

1030 CTCCATCAGGTGTTAAGGATTCCATTCCTGCTTGGATCAAC
1031 CTCCATCAGGTGTTAAGGATTCCATTCCTGCTTGGATCAAC
1029 CTCCATCAGGTGTTAAGGATTCCATTCCTGCTTGGATCAAC
1114 CTTCATCAGGTGTTAAGGATTCCATTCCTGCTTGGATCAAC

1150 AACACCCACGGCCAAAGAAACCAAAGTCGCTGAGAATATAT
1151 AACACCCACGGCCAAAGAAACCAAAGTCGCTGAGAATATAT
1149 AACACCCACGGCCAAAGAAACCAAAGTCGGTGAGAATATAT
1234 AACACCCACGGCCAAAGAAACCAAAGTCGCTGAGAATATAT

1270 TAAAAAA-GCTTGGGTACAATGCGCTGCCAATTATGGCTAT
1271 TAAAAAA-GCTTGGGTACAATGCGCTGCAAATTATGGCTAT
1269 TAAAAAAAGCTTGGGTACAATGCGGTGCAAATTATGGCTAT
1354 TAAAAAACCTTGGGTACAATGCGGTGCAAATTATGGCTAT

1389 GACGACCTTAAGTCTTCGATTGATAAAGCTCATGAGCTAGG
1390 GACGACCTTAAGTCTTTGATTGATAAAGCTCATGAGCTAGG
1389 GACGACCTTAAGTCTTTGATTGATAAAGCTCATGAGCTAGG
1473 GACGACCTTAAGTCTTTGATTGATAAAGCTCATGAGCTAGG

1509 GATAGTTGTTACTTTCACTCTGGAGCTCGTGGTTATCATTG
1510 GATAGTTGTTACTTTCACTCTGGAGCTCGTGGTTATCATTG
1509 GATAGTTGTTACTTTCACTCTGGAGCTCGTGGTTATCATTG
1593 GATAGTTGTTACTTTCACTCTGGAGCTCGTGGTTATCATTG

1628 GATGAGTTCAAATTTGATGGATTTAGATTCGATGGTGTGAC
1630 GATGCGTTCAAATTTGATGGATTTAGATTTGATGGTGTGAC
1629 GATGAGTTCAAATTTGATGGATTTAGATTTGATGGTGTGAC
1713 GATGAGTCCAAATTTGRTGGATTTAGATTTGATGGTGTGAC

1748 GTGGATGCTGTTGTGTATCTGATGCTGGTCAACGATCTTAT
1750 GTGGATGCTGTTGTGTATCTGATGCTGGTCAACGATCTTAT
1749 GTGGATGCTGTTGTGTATCTGATGCTGGTCAACGATCTTAT
1833 GTRGATGCTGCCGTGTATCTGATGCTGGCCAACGATCTTAT
```

Fig. 8
Sheet 5

Fig. 8
SHEET 4

```
TGGGAGATTTTTCTGCCAAATAATGTGGATGGTTCTCCTGCAATTC
TGGGAGATTTTTCTGCCAAATAATGTGGATGGTTCTCCTGCAATTC
TCAGAGATTTTTCTGCCAAATAATGTGGATGGTTCTCCTGCAATTC
TGGGAGATTTTTCTGCCAAATAATGTGGATGGTTCTCCTGCAATTC

TACTCTTTACAGCTTCCTGATGAAATTCCATATAATGGAATATATT
TACTCTTTACAGCTTCCTGATGAAATTCCATATAATGGAATACATT
TACTCTTTACAGCTTCCTGATGAAATTCCATATAATGGAATATATT
TACTCTTTACAGCTTCCTGATGAAATTCCATATAATGGAATATATT

GAATCTCATATTGGAATGAGTAGTCCGGAGCCTAAAATTAACTCAT
GAATCTCATATTGGAATGAGTAGTCCGGAGCCTAAAATTAACTCAT
GAATCTCATATTGGAATGAGTAGTCCGGAGCCTAAAATTAACTCAT
GAATCTCATATTGGAATGAGTAGTCCGGAGCCTAAAATTAACTCAT

TCAAGAGCATTCTTATTATGCTAGTTTTGGTTATCATGTCACAAAT
TCAAGAGCATTCTTATTACGCTAGTTTTGGTTATCATGTCACAAAT
TCAAGAGCATTCTTATTATGCTAGTTTTGGTTATCATGTCACAAAT
TCAAGAGCATTCTTATTATGCTAGTTTTGGTTATCATGTCACAAAT

AATTGTTGTTCTCATGGACATCGTTCACAGCCATGCATCAAATAAT
AATTGTTGTTCTCATGGACATTGTTCACAGCCATGCATCAAATAAT
AATTGTTGTTCTCATGGACATTGTTCACAGCCATGCATCAAATAAT
AATTGTTGTTCTCATGGACATTGTTCACAGCCATGCATCAAATAAT

GATGTGGGATT-CCGCCTCTTTAACTATGGAAACTGGGAGGTACTT
GATGTGGGATTCCCGCCTCTTTAACTATGGAAACTGGGAGGTACTT
GATGTGGGATTTCCGCCTCTTTAACTATGGAAACTGGGAGGTACTT
GATGTGGGATTCCCGCCTCTTTAACTATGGAAACTGGGAGGTACTT

ATCAATGATGTATACTCACCACGGATTATCGGTGGGATTCACTGGG
ATCAATGATGTATATTCACCACGGATTATCGGTGGGATTCACTGGG
ATCAATGATGTGTACTCACCACGGATTATCGGTGGGATTCACTGGG
ATCAATGATGTATACTCACCACGGATTATCGGTGGGATTCACTGGG

TCATAGGCTTTTCCCAGATGCAATTACCATTGGTGAAGATGTTAGC
TCATGGGCTTTTCCCAGATGCAATTACCATTGGTGAAGATGTTAGC
TCATGGGCTTTTCCCAGATGCAATTACCATTGGTGAAGATGTTAGC
TCATGGGCTTTTCCCAGATGCAATTACCATTGGTGAAGATGTTAGC
```

Fig. 8 Sheet 6

Fig. 8 SHEET 5

```
CTCATGGGTCCAGAGTGAAGATACGTATGGACA  11con.seq
CTCATGGGTCCAGAGTGAAGATACGTATGGACA  19con.seq
CTCATGGGTCCAGAGTGAAGATACGTATGGACA  10con.seq
CTCATGGGTCCAGAGTGAAGATACGCATGGACA  psbe2con.seq ATGATCCACCCGAAGAGGAGAGGTATATCTTCC  11con.seq
ATGATCCACCCGAAGAGGAGAGGTATATCTTCC  19con.seq
ATGATCCACCCGAAGAGGAGAGGTATATCTTCC  10con.seq
ATGATCCACCCGAAGAGGAGAGGTATCTCTTCC  psbe2con.seq ACGTGAATTTTAGAGATGAAGTTCTTCCTCGCA  11con.seq
ACGTGAATTTTAGAGATGAAGTTCTTCCTCGCA  19con.seq
ACGTGAATTTTAGAGATGAAGTTCTTCCTCGCA  10con.seq
ACGTGAATTTTAGAGATGAAGTTCTTCCTCGCA  psbe2con.seq TTTTTTGCACCAAGCAGCCGTTTTGGAACGCCC  11con.seq
TTTTTTGCACCAAGCAGCCGTTTTGGAACGCCC  19con.seq
TTTTTTGCACCAAGCAGCCGTTTTGGAACGCCC  10con.seq
TTTTTTGCACCAAGCAGCCGTTTTGGAACGCCC  psbe2con.seq ACTTTAGATGGACTGAACATGTTTGACGGCACC  11con.seq
ACTTTAGATGGACTGAACATGTTTGACTGCACC  19con.seq
ACTTTAGATGGACTGAACATGTTTGACGGCACA  10con.seq
ACTTTAGATGGACTGAACATGTTTGACGGCACA  psbe2con.seq AGGTATCTTCTCTCAAATGCGAGATGGTGGTTG  11con.seq
AGGTATCTTCTCTCAAATGCGAGATGGTGGTTG  19con.seq
AGGTATCTTCTCTCAAATGCGAGATGGTGGTTG  10con.seq
AGGTATCTTCTCTCAAATGCGAGATGGTGGTTG  psbe2con.seq AACTACGAGGAATACTTTGGACTCGCAACTGAT  11con.seq
AACTACGAGGAATACTTTGGACTCGCAACTGAT  19con.seq
AACTACGAGGAATACTTTGGACTCGCAACTGAT  10con.seq
AACTACGAGGAATACTTTGGACTCGCAACTGAT  psbe2con.seq GGAATGCCGACATTTTGTATTCCCGTTCAAGAT  11con.seq
GGAATGCCGACATTTTGTATTCCCGTCCAAGAG  19con.seq
GGAATGCCGACATTTTGTGTTCCCGTTCAAGAT  10con.seq
GGAATGCCGACATTTTGTATTCCCGTTCAAGAT  psbe2con.seq
```

Fig. 8
SHEET 6

```
1868  GGGGGTGTTGGCTTTGACTATCGGCTGCATATGGCAATTGC
1870  GGGGGTGTTGGCTTTGACTATCGGCTGCATATGGCAATTGC
1869  GGGGGTGTTGGCTTTGACTATCGGCTGCATATGGCAATTGC
1953  GGGGGTGTTGGCTTTGACTATCGGCTGCATATGGCAATTGC

1988  AGATGGTCGGAAAAGTGTGTTTCATACGCTGAAAGTCATGA
1990  AGATGGTCGGAAAAGTGTGTTTCATACGCTGAAAGTCATGA
1989  AGATGGTCGGAAAAGTGTGTTTCATACGCTGAAAGTCATGA
2073  AGATGGTCGGAAAAGTGTGTTTCATACGCTGAAAGTCATGA

2108  CCGCCAACATCATTAATAGATCGTGGGATAGCATTGCACAA
2110  CCGTCAACATCATTAATAGATCGTGGGATAGCATTGCACAA
2109  CCGTCAACATCATTAATAGATCGTGGGATAGCATTACACAA
2193  CCGTCAACATCATTAATAGATCGTGGGATAGCATTGCACAA

2228  TGGATTGATTTCCCTAGGGCTGACCACACCTTTCTGATGG
2230  TGGATTGATTTCCCTAGGGCTGAACAACACCTCTCTGATGG
2229  TGGATTGATTTCCCTAGGGCTGAACAACACCTCTCTGATGG
2313  TGGATTGATTTCCCTAGGGCTGAACAACACCTCTCTGATGG

2348  TACCATGGGTTACAAGAATTTGACTGGGCTATGCAGTATCT
2350  TACCGTGGGTTGCAAGAATTTGACCGGCCTATGCAGTATCT
2349  TACCGTGGGTTGCAAGAATTTGACCGGGCTATGCAGTATCT
2433  TACCGTGGGTTGCAAGAATTTGACCGGGCTATGCAGTATCT

2468  GAAAGAGGAAACCTAGTTTTCGTCTTTAATTTTCACTGGAC
2470  GAAAAAGGAAACCTAGTTTTTGTCTTTAATTTTCACTGGAC
2469  GAAAAAGGAAACCTAGTTTTTGTCTTTAATTTTCACTGGAC
2553  GAAAAAGGAAACCTAGTTTTTGTCTTTAATTTTCACTGGAC

2588  TTTGGTGGCTTCGGGAGAATTGATCATAATGCCGAATATTT
2590  TTTGGTGGCTTCGGGAGAATTGATCATAATGCCGAATATTT
2589  TTTGGTGGCTTCGGGAGAATTGATCATAATGCCGAATATTT
2673  TTTGGTGGCTTCGGGAGAATTGATCATAATGCCGAATGTTT

2708  CTAGTAGACAAACTAGAAG---------------------
2710  CTAGTAGACAAAGAAGAAGAAGAAGAAGAAGAAGAAGAAGA
2709  CTAGTAGACAAAGAAGAAGAAGAAGAAGAAG---------
2793  CTAGTAGACAAAGAAGAAGAAGAAGAAGAAG---------
```

Fig. 8 Sheet 8

Fig. 8 SHEET 7

```
TGATAAATGGATTGAGTTGCTCAAGAAACGGGATGAGGATTGGAGA
TGATAAACGGATTGAGTTGCTCAAGAAACGGGATGAGGATTGGAGA
TGATAAATGGATTGAGTTGCTCAAGAAACGGGATGAGGATTGGAGA
TGATAAATGGATTGAGTTGCTCAAGAAACGGGATGAGGATTGGAGA

TCAAGCTCTAGTCGGTGATAAAACTATAGCATTCTGGCTGATGGAC
TCAAGCTCTAGTCGGTGATAAAACTATAGCATTCTGGCTGATGGAC
TCAAGCTCTAGTCGGTGATAAAACTATAGCATTCTGGCTGATGGAC
TCAAGCTCTAGTCGGTGATAAAACTATAGCATTCTGGCTGATGGAC

GATGATTAGGCTTGTAACTATGGGATTAGGAGGAGAAGGGTACCTA
GATGATTAGGCTTGTAACTATGGGATTAGGAGGAGAAGGGTACCTA
GATGATTAGGCTTGTAACTATGGGATTAGGAGGAGAAGGGTACCTA
GATGATTAGGCTTGTAACTATGGGATTAGGAGGAGAAGGGTACCTA

CTCAGTAATTCCCGGAAACCAATTCAGTTATGATAAATGCAGACGG
CTCAGTAATCCCCGGAAACCAATTCAGTTATGATAAATGCAGACGG
CTCAGTAATTCCCAGAAACCAATTCAGTTATGATAAATGCAGACGG
CTCAGTAATTCCCGGAAACCAATTCAGTTATGATAAATGCAGACGG

TGAAGATAAATATGAGTTTATGACTTCAGAACACCAGTTCATATCA
TGAAGATAAATATGAGTTTATGACTTCAGAACACCAGTTCATATCA
TGAAGATAAATATGAGTTTATGACTTCAGAACACCAGTTCATATCA
TGAAGATAAATATGAGTTTATGACTTCAGAACACCAGTTCATATCA

AAATAGCTATTCAGACTATCGCATAGGCTGCCTGAAGCCTGGAAAA
AAAAAGCTATTCAGACTATCGCATACCCTGCCTGAAGCCTGGAAAA
AAAAGGCTATTCAGACTATCGCATAGGCTGCCTGAAGCCTGGAAAA
AAAAAGCTATTCAGACTATCGCATAGGCTGCTGAAGCCTGGAAAA

CACCTCTGAAGGATCGTATGATGATCGTCCTTGTTCAATTATGGTG
CACCTTTGAAGGATGGTATGATGATCGTCCTCGTTCAATTATGGTG
CACCTTTGAAGGATGGTATGATGATCGTCCTCGTTCAATTATGGTG
CACCTTTGAAGGATGGTATGATGATCGTCCTCGTTCAATTATGGTG

-----TAGCAGTAGTAGAAGAACCCATTG------AAGAATGAACG
AGAACTAGCACCAGTAGAAGAAGTAGTAGTAGAAGAAGAATGAACG
-----TAGCAGTAGTAGAAGAAGTAGTAGTAGAAGAAGAATGAACG
-----TAGCAGTAGTAGAAGAAGTAGTAGTAGAAGAAGAATGAACG
```

Fig. 8
Sheet 9

Fig. 8
SHEET 8

```
GTGGGTGATATTGTTCATACACTGACAAATAGA  11con.seq
GTGGGTGATATTGTTCATACACTGACAAATAGA  19con.seq
GTGGGTGATATTGTTCATACACTGACAAATAGA  10con.seq
GTGGGTGATATTGTTCATACACTGACAAATAGA  psbe2con.seq AAGGATATGTATGATTTTATGGCTCTGGATAGA  11con.seq
AAGGATATGTATGATTTTATGGCTCTGGATAGA  19con.seq
AAGGATATGTATGATTTTATGGCTCTGGATAGA  10con.seq
AAGGATATGTATGATTTTATGGCTTTGGATAGA  psbe2con.seq AATTTCATGGGAAATGAATTCGGCCACCCTGAG  11con.seq
AATTTCATGGGAAATGAATTCGGCCACCCTGAG  19con.seq
AATTTCATGGGAAATGAATTCGGCCACCCTGAG  10con.seq
AATTTCATGGGAAATGAATTCGGCCACCCTGAG  psbe2con.seq AGATTTGACCTGGGAGATGCAGAATATTTAAGA  11con.seq
AGATTTGACCTGGGAGATGCAGAATATTTAAGA  19con.seq
AGATTTGACCTGGGAGATGCAGAATATTTAAGA  10con.seq
AGATTTGACCTGGGAGATGCAGAATATTTAAGA  psbe2con.seq CGAAAGGATGAAGGAGATAGGATGATTGTATTT  11con.seq
CGAAAGGATGAAGGAGATAGGATGATTGTATTT  19con.seq
CGAAAGGATGAAGGAGATAGGATGATTGTATTT  10con.seq
CGAAAGGATGAAGGAGATAGGATGATTGTATTT  psbe2con.seq TACAAGGTTCTCTTGGACTCAGATGATCCACTT  11con.seq
TACAAGGTTGCCTTGGACTCAGATGATCCACTT  19con.seq
TACAAGGTTGCCTTGGACTCAGATGATCCACTT  10con.seq
TACAAGGTTGCCTTGGACTCAGATGATCCACTT  psbe2con.seq TATGCACCTAGTAGAACAGCAGTGGTCTATGCA  11con.seq
TATGCACCTTGTAAAACAGCAGTGGTCTATGCA  19con.seq
TATGCACCTAGTAGAACAGCAGTGGTCTATGCA  10con.seq
TATGCACCTAGTAGAACAGCAGTGGTCTATGCA  psbe2con.seq AACTTGTGATCGCGTTGAAAGATTTGAACGTTA  11con.seq
AACTTGTGATCGCGTTGAAAGATTTGAACG---  19con.seq
AACTTGTGATCGCGTTGAAAGATTTGAACG---  10con.seq
AACTTGTGATCGCGTTGAAAGATTTGAACG---  psbe2con.seq
```

Fig. 8
SHEET 9

```
2795 CTTGGTCATCCACATAGAGCTTCTTGAC--------------
2827 ---------CTACATAGAGCTTCTTGACGTATCTGGCAATAT
2814 ---------CCACATAGAGCTTCTTGACGTATCTGGCAATAT
2895 ---------CTACATAGAGCTTCTTGACGTATCTGGCAATAT

2898 AGAGATGAAGTGCTGAACAAA--CATATGTAAAATCGATGAA
2937 AGAGATGAAGTGCTGAACAAA--CATATGTAAAATCGATGAA
2924 AGAGATGAAGTGCTGAACAAAAACATATGTAAAATCGATGAA
3005 AGAGATGAAGTGCTGAACAAA--CATATGTAAAATCGATGAA 2975
3012
3003
3123 GCCCACTAGAAATCAATTATGTGAGACCTAAAAAACAATAAC
```

Fig. 8 Sheet 11

Fig. 8 SHEET 10

```
  ATCAGTCTTGGCGGAATTCCATGTGACAACAAGGTTTGCACTT
TGCATCAGTCTTGGCGGAATTTCATGTGACAC-AAGGTTTGCAATT
TGCATTAGTCTTGGCGGAATTTCATGTGACAA-CAGGTTTGCAATT
TGCATCAGTCTTGGCGGAATTTCATGTGACAA-AAGGTTTGCAATT

TTTATGTCGAATGCTGGGACGATCGAATTCCTGCAGCC
TTTATGTCGAATGCTGGGACGATCGAATTCCTGCAG
TTTATGTCGAATGCTGGGACGATCGAATTCCTGCAGCC
TTTATGTCGAATGCTGGGACGGGCTTCAGCACGTTTTGCTTAGTGA
```

} Fig. 8 Sheet 12

`CATAAAATGGAAATAGTGCTGATCTAATGATGTTTTAANCCNNNNA`

Fig. 8 SHEET 11

```
CTTTCCACTATTAGTAGTCCACCGATATACGC  11con.seq
CTTTCCACTATTAGTAGTGCAACGATATACGC  19con.seq
CTTTCCACTATTAGTAGTGCAACGATATACGC  10con.seq
CTTTCCACTATTAGTAGTGCAACGATATACGC  psbe2con.seq 11con.seq
                                  19con.seq
                                  10con.seq
GTTCTGTAAATTGTCATCTCTTTANATGTACA  psbe2con.seq 11con.seq
                                  19con.seq
                                  10con.seq
AAAAAAAAAAAAAAAACTCGAC            psbe2con.seq
```

Fig. 8 SHEET 12

```
GGATGCTAATGTTTCTGTATTCTTGAAAAAGCACTCTCTTTCACGG
CCTACGATTACAAAGACATAAGAACTTTTTCGTGAGAGAAAGTGCC
   A  N  V  S  V  F  L  K  K  H  S  L  S  R

TTCTACAGTTGCAGCATCGGGGAAAGTCCTTGTGCCTGGAAYCCAG
AAGATGTCAACGTCGTAGCCCCTTTCAGGAACACGGACCTTRGGTC
  S  T  V  A  A  S  G  K  V  L  V  P  G  ?  Q

GACATCTCCAGAAAATTCCCCAGCATCAACTGATGTAGATAGTTCA
CTGTAGAGGTCTTTTAAGGGGTCGTAGTTGACTACATCTATCAAGT
   T  S  P  E  N  S  P  A  S  T  D  V  D  S  S

TGAGCCGTCAAGTGATCTTACAGGAAGTGTTGAAGAGCTGGATTTT
ACTCGGCAGTTCACTAGAATGTCCTTCACAACTTCTCGACCTAAAA
   E  P  S  S  D  L  T  G  S  V  E  E  L  D  F

TAAAACATTAAATACTTCTGAAGAGACAATTATTGATGAATCTGAT
ATTTTGTAATTTATGAAGACTTCTCTGTTAATAACTACTTAGACTA
   K  T  L  N  T  S  E  E  T  I  I  D  E  S  D

Hinc II
GATTTATGAAATAGACCCCCTTTTGACAAACTATCGTCAACACCTT
CTAAATACTTTATCTGGGGGAAAACTGTTTGATAGCAGTTGTGGAA
   I  Y  E  I  D  P  L  L  T  N  Y  R  Q  H  L
```

Fig. 9 Sheet 2

Fig. 9 SHEET 1

Bgl II

```
AAGATCTTGGCTGAAAAGTCTTCTTACAATTCCGAATCCCGACC
                                              90
TTCTAGAACCGACTTTTCAGAAGAATGTTAAGGCTTAGGGCTGG
 K  I  L  A  E  K  S  S  Y  N  S  E  S  R  P

AGTGATAGCTCCTCATCCTCAACAGACCAATTTGAGTTCACTGA
                                              180
TCACTATCGAGGAGTAGGAGTTGTCTGGTTAAACTCAAGTGACT
 S  D  S  S  S  S  S  T  D  Q  F  E  F  T  E

ACAATGGAACACGCTAGCCAGATTAAAACTGAGAACGATGACGT
                                              270
TGTTACCTTGTGCGATCGGTCTAATTTTGACTCTTGCTACTGCA
 T  M  E  H  A  S  Q  I  K  T  E  N  D  D  V

GCTTCATCACTACAACTACAAGAAGGTGGTAAACTGGAGGAGTC
                                              360
CGAAGTAGTGATGTTGATGTTCTTCCACCATTTGACCTCCTCAG
 A  S  S  L  Q  L  Q  E  G  G  K  L  E  E  S

AGGATCAGAGAGAGGGGCATCCCTCCACCTGGACTTGGTCAGAA
                                              450
TCCTAGTCTCTCTCCCCGTAGGGAGGTGGACCTGAACCAGTCTT
 R  I  R  E  R  G  I  P  P  P  G  L  G  Q  K

GATTACAGGTATTCACAGTACAAGAAACTGAGGGAGGCAATTGA
                                              540
CTAATGTCCATAAGTGTCATGTTCTTTGACTCCCTCCGTTAACT
 D  Y  R  Y  S  Q  Y  K  K  L  R  E  A  I  D
```

Fig. 9 SHEET 2

```
                        HinD III
CAAGTATGAGGGTGGTTTGGAAGCTTTTTCTCGTGGTTATGAAAA
----+----+----+----+----+----+----+----+----+
GTTCATACTCCCACCAAACCTTCGAAAAAGAGCACCAATACTTTT
  K  Y  E  G  G  L  E  A  F  S  R  G  Y  E  K

Pvu II
GGCTCCTGGTGCCCAGTCAGCTGCCCTCATTGGAGATTTCAACAAT
----+----+----+----+----+----+----+----+----+
CCGAGGACCACGGGTCAGTCGACGGGAGTAACCTCTAAAGTTGTTA
  A  P  G  A  Q  S  A  A  L  I  G  D  F  N  N

CTGGGAGATTTTCTGCCAAATAATGTGGATGGTTCTCCTGCAATT
----+----+----+----+----+----+----+----+----+
GACCCTCTAAAAGACGGTTTATTACACCTACCAAGAGGACGTTAA
  W  E  I  F  L  P  N  N  V  D  G  S  P  A  I

TGTTAAGGATTCCATTCCTGCTTGGATCAACTACTCTTTACAGCTT
----+----+----+----+----+----+----+----+----+
ACAATTCCTAAGGTAAGGACGAACCTAGTTGATGAGAAATGTCGAA
  V  K  D  S  I  P  A  W  I  N  Y  S  L  Q  L

AGAGGAGAGGTATRTCTTCCAACACCCACGGCCAAAGAAACCAAAG
----+----+----+----+----+----+----+----+----+
TCTCCTCTCCATAYAGAAGGTTGTGGGTGCCGGTTTCTTTGGTTTC
  E  E  R  Y  ?  F  Q  H  P  R  P  K  K  P  K
```

Fig.9 Sheet 4

Fig.9 SHEET 3

```
ATGGGTTTCACTCGTAGTGCTACAGGTATCACTTACCGTGAGTG
----+----+----+----+----+----+----+----+----+ 630
TACCCAAAGTGAGCATCACGATGTCCATAGTGAATGGCACTCAC
 M  G  F  T  R  S  A  T  G  I  T  Y  R  E  W

TGGGACGCAAATGCTGACATTATGACTCGGAATGAATTTGGTGT
----+----+----+----+----+----+----+----+----+ 720
ACCCTGCGTTTACGACTGTAATACTGAGCCTTACTTAAACCACA
  W  D  A  N  A  D  I  M  T  R  N  E  F  G  V

CCTCATGGGTCCAGAGTGAAGATACGYATGGACACTCCATCAGG
----+----+----+----+----+----+----+----+----+ 810
GGAGTACCCAGGTCTCACTTCTATGCRTACCTGTGAGGTAGTCC
  P  H  G  S  R  V  K  I  R  M  D  T  P  S  G

CCTGATGAAATTCCATATAATGGAATATATTATGATCCACCCGA
----+----+----+----+----+----+----+----+----+ 900
GGACTACTTTAAGGTATATTACCTTATATAATACTAGGTGGGCT
  P  D  E  I  P  Y  N  G  I  Y  Y  D  P  P  E

TCGCTGAGAATATATGAATCTCATATTGGAATGAGTAGTCCGGA
----+----+----+----+----+----+----+----+----+ 990
AGCGACTCTTATATACTTAGAGTATAACCTTACTCATCAGGCCT
  S  L  R  I  Y  E  S  H  I  G  M  S  S  P  E
```

Fig. 9 SHEET 4

```
                                                    Xmn I
GCCTAAAATTAACTCATACGTGAATTTTAGAGATGAAGTTCTTCCT
----+----|----+----|----+----|----+----|----+----|
CGGATTTTAATTGAGTATGCACTTAAAATCTCTACTTCAAGAAGGA
  P  K  I  N  S  Y  V  N  F  R  D  E  V  L  P

TCAAGAGCATTCTTATTATGCTAGTTTTGGTTATCATGTCACAAAT
----+----|----+----|----+----|----+----|----+----|
AGTTCTCGTAAGAATAATACGATCAAAACCAATAGTACAGTGTTTA
  Q  E  H  S  Y  Y  A  S  F  G  Y  H  V  T  N

GTCTTTGATTGATAAAGCTCATGAGCTAGGAATTGTTGTTCTCATG
----+----|----+----|----+----|----+----|----+----|
CAGAAACTAACTATTTCGAGTACTCGATCCTTAACAACAAGAGTAC
  S  L  I  D  K  A  H  E  L  G  I  V  V  L  M

GAACATGTTTGACGGCACAGATAGTTGTTACTTTCACTCTGGAGCT
----+----|----+----|----+----|----+----|----+----|
CTTGTACAAACTGCCGTGTCTATCAACAATGAAAGTGAGACCTCGA
  N  M  F  D  G  T  D  S  C  Y  F  H  S  G  A

AAACTGGGAGGTACTTAGGTATCTTCTCTCAAATGCGAGATGGTGG
----+----|----+----|----+----|----+----|----+----|
TTTGACCCTCCATGAATCCATAGAAGAGAGTTTACGCTCTACCACC
  N  W  E  V  L  R  Y  L  L  S  N  A  R  W  W

ATCAATGATGTATACTCACCACGGATTATCGGTGGGATTCACTGGG
----+----|----+----|----+----|----+----|----+----|
TAGTTACTACATATGAGTGGTGCCTAATAGCCACCCTAAGTGACCC
  S  M  M  Y  T  H  H  G  L  S  V  G  F  T  G
```

Fig. 9 SHEET 5

```
CGCATAAAAAASCTTGGGTACAATGCGGTGCAAATTATGGCTAT
----+----+----+----+----+----+----+----+----+ 1080
GCGTATTTTTSGAACCCATGTTACGCCACGTTTAATACCGATA
  R  I  K  ?  L  G  Y  N  A  V  Q  I  M  A  I

TTTTTTGCACCAAGCAGCCGTTTTGGAACGCCCGACGACCTTAA
----+----+----+----+----+----+----+----+----+ 1170
AAAAAACGTGGTTCGTCGGCAAAACCTTGCGGGCTGCTGGAATT
  F  F  A  P  S  S  R  F  G  T  P  D  D  L  K

GACATTGTTCACAGCCATGCATCAAATAATACTTTAGATGGACT
----+----+----+----+----+----+----+----+----+ 1260
CTGTAACAAGTGTCGGTACGTAGTTTATTATGAAATCTACCTGA
  D  I  V  H  S  H  A  S  N  N  T  L  D  G  L
```

Sac I

```
CGTGGTTATCATTGGATGTGGGATTCCCGCCTCTTTAACTATGG
----+----+----+----+----+----+----+----+----+ 1350
GCACCAATAGTAACCTACACCCTAAGGGCGGAGAAATTGATACC
  R  G  Y  H  W  M  W  D  S  R  L  F  N  Y  G

TTGGATGAGTTCAAATTTGATGGATTTAGATTTGATGGTGTGAC
----+----+----+----+----+----+----+----+----+ 1440
AACCTACTCAAGTTTAAACTACCTAAATCTAAACTACCACACTG
  L  D  E  F  K  F  D  G  F  R  F  D  G  V  T

AACTACGAGGAATACTTTGGACTCGCAACTGATGTGGATGCTGT
----+----+----+----+----+----+----+----+----+ 1530
TTGATGCTCCTTATGAAACCTGAGCGTTGACTACACCTACGACA
  N  Y  E  E  Y  F  G  L  A  T  D  V  D  A  V
```

Fig. 9 SHEET 6

```
                          Hinc II
TGTGTATCTGATGCTGGTCAACGATCTTATTCACGGCTTTTCCCA
---+----+----+----+----+----+----+----+----+--
ACACATAGACTACGACCAGTTGCTAGAATAAGTGCCCGAAAAGGGT
 V  Y  L  M  L  V  N  D  L  I  H  G  L  F  P TTGTATTCCCGTTCAAGATGGGGGTGTTGGCTTTGACTATCGGCTG
---+----+----+----+----+----+----+----+----+--
AACATAAGGGCAAGTTCTACCCCCACAACCGAAACTGATAGCCGAC
 C  I  P  V  Q  D  G  G  V  G  F  D  Y  R  L GGATGAGGATTGGAGAGTGGGTGATATTGTTCATACACTGACAAAT
---+----+----+----+----+----+----+----+----+--
CCTACTCCTAACCTCTCACCCACTATAACAAGTATGTGACTGTTTA
 D  E  D  W  R  V  G  D  I  V  H  T  L  T  N TCAAGCTCTAGTCGGTGATAAAACTATAGCATYCTGGCTGATGGAC
---+----+----+----+----+----+----+----+----+--
AGTTCGAGATCAGCCACTATTTTGATATCGTARGACCGACTACCTG
 Q  A  L  V  G  D  K  T  I  A  ?  W  L  M  D ATTAATAGATCGTGGGATAGCATTGCACAAGATGATTAGGCTTGTA
---+----+----+----+----+----+----+----+----+--
TAATTATCTAGCACCCTATCGTAACGTGTTCTACTAATCCGAACAT
 L  I  D  R  G  I  A  L  H  K  M  I  R  L  V
```

Fig. 9 SHEET 7

Fig. 9 Sheet 8

```
GATGCAATTACCATTGGTGAAGATGTTAGCGGAATGCCGACATT
────┼────┼────┼────┼────┼────┼────┼────┼────┼──── 1620
CTACGTTAATGGTAACCACTTCTACAATCGCCTTACGGCTGTAA
  D   A   I   T   I   G   E   D   V   S   G   M   P   T   F
```

Nde I

```
CATATGGCAATTGCTGATAAATGGATTGAGTTGCTCAAGAAACG
────┼────┼────┼────┼────┼────┼────┼────┼────┼──── 1710
GTATACCGTTAACGACTATTTACCTAACTCAACGAGTTCTTTGC
  H   M   A   I   A   D   K   W   I   E   L   L   K   K   R
```

```
AGAAGATGGTCGGAAAAGTGTGTTTCATMCGCTGAAAGTCATGA
────┼────┼────┼────┼────┼────┼────┼────┼────┼──── 1800
TCTTCTACCAGCCTTTTCACACAAAGTAKGCGACTTTCAGTACT
  R   R   W   S   E   K   C   V   S   ?   A   E   S   H   D
```

Hinc II

```
AAGGATATGTATGATTTTATGGCTCTGGATAGACCGTCAACATC
────┼────┼────┼────┼────┼────┼────┼────┼────┼──── 1890
TTCCTATACATACTAAAATACCGAGACCTATCTGGCAGTTGTAG
  K   D   M   Y   D   F   M   A   L   D   R   P   S   T   S
```

Asp 718
Kpn I

```
ACTATGGGATTAGGAGGAGAAGGGTACCTAAATTTCATGGGAAA
────┼────┼────┼────┼────┼────┼────┼────┼────┼──── 1980
TGATACCCTAATCCTCCTCTTCCCATGGATTTAAAGTACCCTTT
  T   M   G   L   G   G   E   G   Y   L   N   F   M   G   N
```

Fig. 9 SHEET 8

```
                EcoR I
       TGAATTCGGCCACCCTGAGTGGATTGATTTCCCTAGGGCTGARCAA
       ACTTAAGCCGGTGGGACTCACCTAACTAAAGGGATCCCGACTYGTT
        E  F  G  H  P  E  W  I  D  F  P  R  A  E  Q

Ssp I
       TGATAAATGCAGACGGAGATTTGACCTGGGAGATGCAGAATATTTA
       ACTATTTACGTCTGCCTCTAAACTGGACCCTCTACGTCTTATAAAT
        D  K  C  R  R  R  F  D  L  G  D  A  E  Y  L

TGAAGATAAATATGAGTTTATGACTTCAGAACACCAGTTCATATCA
       ACTTCTATTTATACTCAAATACTGAAGTCTTGTGGTCAAGTATAGT
        E  D  K  Y  E  F  M  T  S  E  H  Q  F  I  S

CCTAGTTTTTGTCTTTAATTTTCACTGGACAAATAGCTATTCAGAC
       GGATCAAAAACAGAAATTAAAAGTGACCTGTTTATCGATAAGTCTG
        L  V  F  V  F  N  F  H  W  T  N  S  Y  S  D

GGACTCAGATGATCCACTTTTTGGTGGCTTCGGGAGAATTGATCAT
       CCTGAGTCTACTAGGTGAAAAACCACCGAAGCCCTCTTAACTAGTA
        D  S  D  D  P  L  F  G  G  F  G  R  I  D  H

YCGYYCAATTATGGTGTATGCACCTAGTAGAACAGCAGTGGTCTAT
       RGCRRGTTAATACCACATACGTGGATCATCTTGTCGTCACCAGATA
        R  ?  I  M  V  Y  A  P  S  R  T  A  V  V  Y

NGAAGAATTTT
       ─────────→ 2531
       NCTTCTTAAAA
        E  E  F
```

Fig 9 Sheet 10

Fig 9 SHEET 9

```
      CACCTCTCTGATGGCTCAGTAATTCCCGGAAACCAATTCAGTTA
      ----+----+----+----+----+----+----+----+----+  2070
      GTGGAGAGACTACCGAGTCATTAAGGGCCTTTGGTTAAGTCAAT
       H  L  S  D  G  S  V  I  P  G  N  Q  F  S  Y
```

```
           Nco I
           ┊
      AGATACCATGGGTTGCAAGAATTTGACCGGGCTATGCAGTATCT
      ----+----+----+----+----+----+----+----+----+  2160
      TCTATGGTACCCAACGTTCTTAAACTGGCCCGATACGTCATAGA
       R  Y  H  G  L  Q  E  F  D  R  A  M  Q  Y  L
```

```
      CGAAAGGATGAAGGAGATAGGATGATTGTATTTGAAARAGGAAA
      ----+----+----+----+----+----+----+----+----+  2250
      GCTTTCCTACTTCCTCTATCCTACTAACATAAACTTTYTCCTTT
       R  K  D  E  G  D  R  M  I  V  F  E  ?  G  N
```

```
      TATCGCATAGGCTGCCTGAAGCCTGGAAAATACAAGGTTGGCTT
      ----+----+----+----+----+----+----+----+----+  2340
      ATAGCGTATCCGACGGACTTCGGACCTTTTATGTTCCAACCGAA
       Y  R  I  G  C  L  K  P  G  K  Y  K  V  G  L
```

```
           Ssp I
           ┊
      AATGCCGAATATTTCACCTCTGAAGGATCGTATGATGATCGYCC
      ----+----+----+----+----+----+----+----+----+  2430
      TTACGGCTTATAAAGTGGAGACTTCCTAGCATACTACTAGCRGG
       N  A  E  Y  F  T  S  E  G  S  Y  D  D  R  P
```

```
      GCACTAGTAGACAAANTAGAAGNAGAAGAAGAAGAAGAANCCGN
      ----+----+----+----+----+----+----+----+----+  2520
      CGTGATCATCTGTTTNATCTTCNTCTTCTTCTTCTTNGGCN
       A  L  V  D  K  ?  E  ?  E  E  E  E  E  ?  ?
```

Fig. 9 SHEET 10

```
              10         20        30
 1    --GATGGGGCCTTGAACTCAGCAATTTGACACTCAGT
 1    TTGATGGG-CCTTGAACTCAGCAATTTGACACTCAGT
 1    TTGATGGGGCCTTGAACTCAGCAATTTGACACTCAGT
 1    T-----------------------------------
 1    ------------------------------------

80         90       100
69    TTTTTCTCTTAATTCCAACCAAGG-AATGAATAAAAA
70    TTTTTCTCTTAATTCCAACCAGGGGAATGAATAAAAG
71    TTTTTCTCTTAATTCCAACCAAGG-AATGAATAAAAG
 7    ----------------------------AAGAG
 1    ----------------------------AAGAG 150        160       170
138   GAAAGATGGTGTATACACTCTCTGGAGTTCGTTTTCC
140   GAAAGATGGTGTATATACTCTCTGGAGTTCGTTTTCC
140   GAAAGATGGTGTATACACTCTCTGGAGTTCGTTTTCC
33    ---------------------------------TCT
 1

220        230       240
208   CAGCAGTAATGGTGATCGGAGGAATGCTAATATTTCT
210   CAGCAGTAATGGTGATCGGAGGAATGCTAATGTTTCT
210   CAGCAGTAATGGTGATCGGAGGAATGCTAATGTTTCT
48    CA----------------------------------
 1    ---------------------GGATGCTAATGTTTCT 290        300       310  *
278   ATCTTGGCTGAAAAGTCTTCTTACAATTCCGAATCCC
280   ATCTTGGCTGAAAAGTCTTCTTACAATTCCGAATTCC
280   ATCTTGGCTGAAAAGTCTTCTTACAATTCCGAATTCC
57    ATCTTGGCTGAAAAGTCTTCTTACAATTCCGAATTCC
50    ATCTTGGCTGAAAAGTCTTCTTACAATTCCGAATCCC
                                        *
```

Fig. 10 Sheet 2

Fig. 10 SHEET 1

```
        40         50         60         70
         |          |          |          |
TAGTTACACTGCCATCACTTATCAGATCTCTAT  10con. seq
TAGTTACACTCCTATCACTTATCAGATCTCTAT  11con. seq
TAGTTACACTCCTATCACTTATCAGATCTCTAT  19con. seq
------------CATTA---------------- 86CON. SEQ
--------------------------------- pcrsbe2con. seq 110        120        130        140
         |          |          |          |
GATAGATTTGTAAAAACCCTAAGGAGAGAAGAA  10con. seq
GATAGATTTGTAAAAACCCTAAGGAGAGAAGAA  11con. seq
GATAGATTTGTAAAAACCCTAAGGAGAGAAGAA  19con. seq
GAGAAATT------AACTATGAGAGGA------ 86CON. SEQ
--------------------------------- pcrsbe2con. seq 180        190        200        210
         |          |          |          |
TACTGTTCCATCAGTGTACAAATCTAATGGATT  10con. seq
TACTGTTCCATCAGTGTACAAATCTAATGGATT  11con. seq
TACTGTTCCATCAGTGTACAAATCTAATGGATT  19con. seq
CACCAT--CACCA-------------------T 86CON. SEQ
--------------------------------- pcrsbe2con. seq 250        260        270        280
         |          |          |          |
GTATTCTTGAAAAAACACTCTCTTTCACGGAAG  10con. seq
GTATTCTTGAAAAAGCACTCTCTTTCACGGAAG  11con. seq
GTATTCTTGAAAAAGCACTCTCTTTCACGGAAG  19con. seq
-------------------------CCATGG--G 86CON. SEQ
GTATTCTTGAAAAAGCACTCTCTTTCACGGAAG  pcrsbe2con. seq 320        330        340        350
         |          |          |          |
GACCTTCTACAATTGCAGCATCGGGGAAAGTCC  10con. seq
GACCTTCTACAGTTGCAGCATCGGGGAAAGTCC  11con. seq
GACCTTCTACAGTTGCAGCATCGGGGAAAGTCC  19con. seq
GACCTTCTACAGTTGCAGCATCGGGGAAAGTCC  86CON. SEQ
GACCTTCTACAGTTGCAGCATCGGGGAAAGTCC  pcrsbe2con. seq
```

Fig. 10 SHEET 2

```
            360 *        370         380
348  TTGTGCCTGGAATCCAGAGTGATAGCTCCTCATCCTC
350  TTGTGCCTGGAACCCAGAGTGATAGCTCCTCATCCTC
350  TTGTGCCTGGAACCCAGAGTGATAGCTCCTCATCCTC
127  TTGTGCCTGGAACCCAGAGTGATAGCTCCTCATCCTC
120  TTGTGCCTGGAAYCCAGAGTGATAGCTCCTCATCCTC 430         440         450
418  AGAAAATTCCCCAGCATCAACTGATGTAGATAGTTCA
420  AGAAAATTCCCCAGCATCAACTGATGTAGATAGTTCA
420  AGAAAATTCCCCAGCATCAACTGATGTAGATAGTTCA
197  AGAAAATTCCCCAGCATCAACTGATGTAGATAGTTCA
190  AGAAAATTCCCCAGCATCAACTGATGTAGATAGTTCA 500         510         520
488  AACGATGACGTTGAGCCGTCAAGTGATCTTACAGGAA
490  AACGATGACGTTGAGCCGTCAAGTGATCTTACAGGAA
490  AACGATGACGTTGAGCCGTCAAGTGATCTTACAGGAA
267  AACGATGACGTTGAGCCGTCAAGTGATCTTACAGGAA
260  AACGATGACGTTGAGCCGTCAAGTGATCTTACAGGAA 570         580         590
558  AACTACAAGAAGGTGGTAAACTGGAGGAGTCTAAAAC
560  AACTACAAGAAGGTGGTAAACTGGAGGAGTCTAAAAC
560  AACTACAAGAAGGTGGTAAACTGGAGGAGTCTAAAAC
337  AACTACAAGAAGGTGGTAAACTGGAGGAGTCTAAAAC
330  AACTACAAGAAGGTGGTAAACTGGAGGAGTCTAAAAC 640         650         660
628  ATCTGATAGGATCAGAGAGAGGGGCATCCCTCCACCT
630  ATCTGATAGGATCAGAGAGAGGGGCATCCCTCCACCT
630  ATCTGATAGGATCAGAGAGAGGGGCATCCCTCCACCT
407  ATCTGATAGGATCAGAGAGAGGGGCATCCCTCCACCT
400  ATCTGATAGGATCAGAGAGAGGGGCATCCCTCCACCT
```

Fig. 10 Sheet 4

Fig. 10 SHEET 3

```
         390       400       410       420
          |         |         |         |
AACAGATCAATTTGAGTTCGCTGAGACATCTCC  10con. seq
AACAGACCAATTTGAGTTCACTGAGACATCTCC  11con. seq
AACAGACCAATTTGAGTTCACTGAGACATCTCC  19con. seq
AACAAACCAATTTGAGTTCACTGAGACATCTCC  86CON. SEQ
AACAGACCAATTTGAGTTCACTGAGACATCTCC  pcrsbe2con. seq 460       470       480       490
          |         |         |         |
ACAATGGAACACGCTAGCCAGATTAAAACTGAG  10con. seq
ACAATGGAACACGCTAGCCAGATTAAAACTGAG  11con. seq
ACAATGGAACACGCTAGCCAGATTAAAACTGAG  19con. seq
ACAATGGAACACGCTAGCCAGATTAAAACTGAG  86CON. SEQ
ACAATGGAACACGCTAGCCAGATTAAAACTGAG  pcrsbe2con. seq 530       540       550       560
          |         |         |         |
GTGTTGAAGAGCTGGATTTTGCTTCATCACTAC  10con. seq
GTGTTGAAGAGCTGGATTTTGCTTCATCACTAC  11con. seq
GTGTTGAAGAGCTGGATTTTGCTTCATCACTAC  19con. seq
GTGTTGAAGAGCTGGATTTTGCTTCATCACTAC  86CON. SEQ
GTGTTGAAGAGCTGGATTTTGCTTCATCACTAC  pcrsbe2con. seq 600       610       620       630
          |         |         |         |
ATTAAATACTTCTGAAGAGACAATTATTGATGA  10con. seq
ATTAAATACTTCTGAAGAGACAATTATTGATGA  11con. seq
ATTAAATACTTCTGAAGAGACAATTATTGATGA  19con. seq
ATTAAATACTTCTGAAGAGACAATTATTGATGA  86CON. SEQ
ATTAAATACTTCTGAAGAGACAATTATTGATGA  pcrsbe2con. seq 670       680       690       700
          |         |         |         |
GGACTTGGTCAGAAGATTTATGAAATAGACCCC  10con. seq
GGACTTGGTCAGAAGATTTATGAAATAGACCCC  11con. seq
GGACTTGGTCAGAAGATTTATGAAATAGACCCC  19con. seq
GGACTTGGTCAGAAGATTTATGAAATAGACCCC  86CON. SEQ
GGACTTGGTCAGAAGATTTATGAAATAGACCCC  pcrsbe2con. seq
```

Fig.10 SHEET 4

|     |     |     |     |
| --- | --- | --- | --- |
|     | 710 | 720 | 730 |
| 698 | CTTTTGACAAACTATCGTCAACACCTTGATTACAGGT |
| 700 | CTTTTGACAAACTATCGTCAACACCTTGATTACAGGT |
| 700 | CTTTTGACAAACTATCGTCAACACCTTGATTACAGGT |
| 477 | CTTTTGACAAACTATCGTCAACACCTTGATTACAGGT |
| 470 | CTTTTGACAAACTATCGTCAACACCTTGATTACAGGT |

|     | 780 | 790 | 800 |
| --- | --- | --- | --- |
| 768 | ACAAGTATGAGGGTGGTTTGGAAGCTTTTCTCGTGG |
| 770 | ACAAGTATGAGGGTGGTTTGGAAGC-TTTTCTCGTGG |
| 770 | ACAAGTATGAGGGTGGTTTGGAAGCCTTTTCTCGTGG |
| 547 | ACAAGTATGAGGGTGGTTTGGAAGCTTTTCTCGTGG |
| 540 | ACAAGTATGAGGGTGGTTTGGAAGCTTTTCTCGTGG |

|     | 850 | 860 | 870 |
| --- | --- | --- | --- |
| 838 | AGGTATCACTTACCGTGAGTGGGCTCCTGGTGCCCAG |
| 839 | AGGTATCACTTACCGTGAGTGGGCTCCTGGTGCCCAG |
| 840 | AGGTATCACTTACCGTGAGTGGGCTCTTGGTGCCCAG |
| 617 | AGGTATCACTTACCGTGAGTGGGCTCCTGGTGCCCAG |
| 610 | AGGTATCACTTACCGTGAGTGGGCTCCTGGTGCCCAG |

|     | 920 | 930 | 940 |
| --- | --- | --- | --- |
| 908 | GACGCAAATGCTGACTTTATGACTCGGAATGAATTTG |
| 909 | GACGCAAATGCTGACATTATGACTCGGAATGAATTTG |
| 910 | GACGCAAATGCTGACATTATGACTCGGAATGAATTTG |
| 687 | GACGCAAATGCTGACATTATGACTCGGAATGAATTTG |
| 680 | GACGCAAATGCTGACATTATGACTCGGAATGAATTTG |

|     | 990 | 1000 | 1010 |
| --- | --- | --- | --- |
| 978 | ATGGTTCTCCTGCAATTCCTCATGGGTCCAGAGTGAA |
| 979 | ATGGTTCTCCTGCAATTCCTCATGGGTCCAGAGTGAA |
| 980 | ATGGTTCTCCTGCAATTCCTCATGGGTCCAGAGTGAA |
| 757 | ATGGTTCTCCTGCAATTCCTCATGGGTCCAGAGTGAA |
| 750 | ATGGTTCTCCTGCAATTCCTCATGGGTCCAGAGTGAA |

Fig. 10 Sheet 6

Fig. 10 SHEET 5

```
        740       750       760       770
ATTCACAGTACAAGAAACTGAGGGAGGCAATTG  10con. seq
ATTCACAGTACAAGAAACTGAGGGAGGCAATTG  11con. seq
ATTCACAGTACAAGAAACTGAGGGAGGCAATTG  19con. seq
ATTCACAGTACAAGAAACTGAGGGAGGCAATTG  86CON. SEQ
ATTCACAGTACAAGAAACTGAGGGAGGCAATTG  pcrsbe2con. seq 810       820       830       840
TTATGAAAGAATGGGTTTCACTCGTAGTGCTAC  10con. seq
TTATGAAAAAATGGGTTTCACTCGTAGTGCTAC  11con. seq
TTATGAAAAAATGGGTTTCACTCGTAGTGCTAC  19con. seq
TTATGAAAAAATGGGTTTCACTCGTAGTGCTAC  86CON. SEQ
TTATGAAAAAATGGGTTTCACTCGTAGTGCTAC  pcrsbe2con. seq 880       890       900       910
TCAGCTGCCCTCATTGGGGATTTCAACAATTGG  10con. seq
TCAGCTGCCCTCATTGGAGATTTCAACAATTGG  11con. seq
TCAGCTGCCCTCATTGGAGATTTCAACAATTGG  19con. seq
TCAGCTGCCCTCATTGGAGATTTCAACAATTGG  86CON. SEQ
TCAGCTGCCCTCATTGGAGATTTCAACAATTGG  pcrsbe2con. seq 950       960       970       980
GTGTCTGAGAGATTTTTCTGCCAAATAATGTGG  10con. seq
GTGTCTGGGAGATTTTTCTGCCAAATAATGTGG  11con. seq
GTGTCTGGGAGATTTTTCTGCCAAATAATGTGG  19con. seq
GTGTCTGGGAGATTTTTCTGCCAAATAATGTGG  86CON. SEQ
GTGTCTGGGAGATTTTTCTGCCAAATAATGTGG  pcrsbe2con. seq 1020      1030      1040      1050
GATACGTATGGACACTCCATCAGGTGTTAAGGA  10con. seq
GATACGTATGGACACTCCATCAGGTGTTAAGGA  11con. seq
GATACGTATGGACACTCCATCAGGTGTTAAGGA  19con. seq
GATACGTATGGACACTCCATCAGGTGTTAAGGA  86CON. SEQ
GATACGYATGGACACTCCATCAGGTGTTAAGGA  pcrsbe2con. seq
```

Fig. 10 SHEET 6

```
            1060       1070       1080
1048  TTCCATTCCTGCTTGGATCAACTACTCTTTACAGCTT
1049  TTCCATTCCTGCTTGGATCAACTACTCTTTACAGCTT
1050  TTCCATTCCTGCTTGGATCAACTACTCTTTACAGCTT
 827  TTCCATTCCTGCTTGGATCAACTACTC--TACAGCTT
 820  TTCCATTCCTGCTTGGATCAACTACTCTTTACAGCTT 1130       1140       1150
1118  GATCCACCCGAAGAGGAGAGGTATATCTTCCAACACC
1119  GATCCACCCGAAGAGGAGAGGTATATCTTCCAACACC
1120  GATCCACCCGAAGAGGAGAGGTATATCTTCCAACACC
 895  GATCCACCCGAAGAGGAGAGGTATATCTTCCAACACC
 890  GATCCACCCGAAGAGGAGAGGTATRTCTTCCAACACC 1200       1210       1220
1188  ATGAATCTCATATTGGAATGAGTAGTCCGGAGCCTAA
1189  ATGAATCTCATATTGGAATGAGTAGTCCGGAGCCTAA
1190  ATGAATCTCATATTGGAATGAGTAGTCCGGAGCCTAA
 965  ATGAATCTCATATTGGAATGAGTAGTCCGGAGCCTAA
 960  ATGAATCTCATATTGGAATGAGTAGTCCGGAGCCTAA 1270       1280       1290
1258  TCTTCCTCGCATAAAAAAAGCTTGGGTACAATGCGGT
1259  TCTTCCTCGCATAAAAAA-GCTTGGGTACAATGCGCT
1260  TCTTCCTCGCATAAAAAA-GCTTGGGTACAATGCGCT
1035  TCTTCCTCGCATAAAAAA-GCTTGGGTACAATGCGCT
1030  TCTTCCTCGCATAAAAAA-SCTTGGGTACAATGCGGT 1340       1350       1360
1328  TGCTAGTTTTGGTTATCATGTCACAAATTTTTTTGCA
1328  TGCTAGTTTTGGTTATCATGTCACAAATTTTTTTGCA
1329  CGCTAGTTTTGGTTATCATGTCACAAATTTTTTTGCA
1104  TGCTAGTTTTGGTTATCATGTCACAAATTTTTTTGCA
1099  TGCTAGTTTTGGTTATCATGTCACAAATTTTTTTGCA
```

Fig. 10 Sheet 8

Fig. 10 SHEET 7

```
          1090      1100      1110      1120
CCTGATGAAATTCCATATAATGGAATATATTAT  10con. seq
CCTGATGAAATTCCATATAATGGAATATATTAT  11con. seq
CCTGATGAAATTCCATATAATGGAATACATTAT  19con. seq
CCTGATGAAATTCCATATAATGGAATATATTAT  86CON. SEQ
CCTGATGAAATTCCATATAATGGAATATATTAT  pcrsbe2con. seq 1160      1170      1180      1190
CACGGCCAAAGAAACCAAAGTCGGTGAGAATAT  10con. seq
CACGGCCAAAGAAACCAAAGTCGCTGAGAATAT  11con. seq
CACGGCCAAAGAAACCAAAGTCGCTGAGAATAT  19con. seq
CACGGCCAAAGAAACCAAAGTCGCTGAGAATAT  86CON. SEQ
CACGGCCAAAGAAACCAAAGTCGCTGAGAATAT  pcrsbe2con seq 1230      1240      1250      1260
AATTAACTCATACGTGAATTTTAGAGATGAAGT  10con. seq
AATTAACTCATACGTGAATTTTAGAGATGAAGT  11con. seq
AATTAACTCATACGTGAATTTTAGAGATGAAGT  19con. seq
AATTAACTCATACGTGAATTTTAGAGATGAAGT  86CON. SEQ
AATTAACTCATACGTGAATTTTAGAGATGAAGT  pcrsbe2con. seq 1300      1310      1320      1330
GCAAATTATGGCTATTCAAGAGCATTCTTATTA  10con. seq
GCGAATTATGGCTATTCAAGAGCATTCTTATTA  11con. seq
GCAAATTATGGCTATTCAAGAGCATTCTTATTA  19con. seq
GCAAATTATGGCTATTCAAGAGCATTCTTATTA  86CON. SEQ
GCAAATTATGGCTATTCAAGAGCATTCTTATTA  pcrsbe2con. seq 1370      1380      1390      1400
CCAAGCAGCCGTTTTGGAACGCCCGACGACCTT  10con. seq
CCAAGCAGCCGTTTTGGAACGCCCGACGACCTT  11con. seq
CCAAGCAGCCGTTTTGGAACGCCCGACGACCTT  19con. seq
CCAAGCAGCCGTTTTGGAACGCCCGACGACCTT  86CON. SEQ
CCAAGCAGCCGTTTTGGAACGCCCGACGACCTT  pcrsbe2con. seq
```

Fig. 10 SHEET 8

```
              1410         1420         1430
1398  AAGTCTTTGATTGATAAAGCTCATGAGCTAGGAATTG
1398  AAGTCTTCGATTGATAAAGCTCATGAGCTAGGAATTG
1399  AAGTCTTTGATTGATAAAGCTCATGAGCTAGGAATTG
1174  AAGTCTTTGATTGATAAAGCTCATGAGCTAGGAATTG
1169  AAGTCTTTGATTGATAAAGCTCATGAGCTAGGAATTG 1480         1490         1500
1468  CAAATAATACTTTAGATGGACTGAACATGTTTGACGG
1468  CAAATAATACTTTAGATGGACTGAACATGTTTGACGG
1469  CAAATAATACTTTAGATGGACTGAACATGTTTGACTG
1244  CAAATAATACTTTAGATGGACTGAACATGTTTGACGG
1239  CAAATAATACTTTAGATGGACTGAACATGTTTGACGG 1550         1560         1570
1538  TGGTTATCATTGGATGTGGGATTTCCGCCTCTTTAAC
1538  TGGTTATCATTGGATGTGGGATT-CCGCCTCTTTAAC
1539  TGGTTATCATTGGATGTGGGATTCCCGCCTCTTTAAC
1314  TGGTTATCATTGGATGTGGGATTCCCGCCTTTTAAC
1309  TGGTTATCATTGGATGTGGGATTCCCGCCTCTTTAAC 1620         1630         1640
1608  TCAAATGCGAGATGGTGGTTGGATGAGTTCAAATTTG
1607  TCAAATGCGAGATGGTGGTTGGATGAGTTCAAATTTG
1609  TCAAATGCGAGATGGTGGTTGGATGCGTTCAAATTTG
1384  TCAAATGCGAGATGGTGGTTGGATGAGTTCAAATTTG
1379  TCAAATGCGAGATGGTGGTTGGATGAGTTCAAATTTG 1690         1700         1710
1678  TGTGTACTCACCACGGATTATCGGTGGGATTCACTGG
1677  TGTATACTCACCACGGATTATCGGTGGGATTCACTGG
1679  TGTATATTCACCACGGATTATCGGTGGGATTCACTGG
1454  TGTATACTCACCACGGATTATCGGTGGGATTCACTGG
1449  TGTATACTCACCACGGATTATCGGTGGGATTCACTGG
```

Fig. 10 Sheet 10

Fig. 10 SHEET 9

```
     1440      1450      1460      1470
TTGTTCTCATGGACATTGTTCACAGCCATGCAT  10con. seq
TTGTTCTCATGGACAT[C]GTTCACAGCCATGCAT 11con. seq
TTGTTCTCATGGACATTGTTCACAGCCATGCAT  19con. seq
TTGTTCTCATGGACATTGTTCACAGCCATGCAT  86CON. SEQ
TTGTTCTCATGGACATTGTTCACAGCCATGCAT  pcrsbe2con. seq 1510      1520      1530      1540
CAC[A]GATAGTTGTTACTTTCACTCTGGAGCTCG 10con. seq
CACCGATAGTTGTTACTTTCACTCTGGAGCTCG  11con. seq
CACCGATAGTTGTTACTTTCACTCTGGAGCTCG  19con. seq
CACCGATAGTTGTTACTTTCACTCTGGAGCTCG  86CON. SEQ
CAC[A]GATAGTTGTTACTTTCACTCTGGAGCTCG pcrsbe2con. seq 1580      1590      1600      1610
TATGGAAACTGGGAGGTACTTAGGTATCTTCTC  10con. seq
TATGGAAACTGGGAGGTACTTAGGTATCTTCTC  11con. seq
TATGGAAACTGGGAGGTACTTAGGTATCTTCTC  19con. seq
TATGGAAACTGGGAGGTACTTAGGTATCTTCTC  86CON. SEQ
TATGGAAACTGGGAGGTACTTAGGTATCTTCTC  pcrsbe2con. seq 1650      1660      1670      1680
ATGGATTTAGATTTGATGGTGTGACATCAATGA  10con. seq
ATGGATTTAGATT[C]GATGGTGTGACATCAATGA 11con. seq
ATGGATTTAGATTTGATGGTGTGACATCAATGA  19con. seq
ATGGATTTAGATTTGATGGTGTGACATCAATGA  86CON. SEQ
ATGGATTTAGATTTGATGGTGTGACATCAATGA  pcrsbe2con. seq 1720      1730      1740      1750
GAACTACGAGGAATACTTTGGACTCGCAACTGA  10con. seq
GAACTACGAGGAATACTTTGGACTCGCAACTGA  11con. seq
GAACTACGAGGAATACTTTGGACTCGCAACTGA  19con. seq
GAACTACGAGGAATACTTTGGACTCGCAACTGA  86CON. SEQ
GAACTACGAGGAATACTTTGGACTCGCAACTGA  pcrsbe2con. seq
```

Fig. 10 SHEET 10

```
         1760      1770      1780
1748 TGTGGATGCTGTTGTGTATCTGATGCTGGTCAACGAT
1747 TGTGGATGCTGTTGTGTATCTGATGCTGGTCAACGAT
1749 TGTGGATGCTGTTGTGTATCTGATGCTGGTCAACGAT
1524 TGTGGATGCTGTTGTGTATCTGATGCTGGTCAACGAT
1519 TGTGGATGCTGTTGTGTATCTGATGCTGGTCAACGAT 1830      1840      1850
1818 ATTGGTGAAGATGTTAGCGGAATGCCGACATTTTGTG
1817 ATTGGTGAAGATGTTAGCGGAATGCCGACATTTTGTA
1819 ATTGGTGAAGATGTTAGCGGAATGCCGACATTTTGTA
1594 ATTGGTGAAGATGTTAGCGGAATGCCGACATTTTGTA
1589 ATTGGTGAAGATGTTAGCGGAATGCCGACATTTTGTA 1900      1910      1920
1888 ATCGGCTGCATATGGCAATTGCTGATAAATGGATTGA
1887 ATCGGCTGCATATGGCAATTGCTGATAAATGGATTGA
1889 ATCGGCTGCATATGGCAATTGCTGATAAACGGATTGA
1664 ATCGGCTGCATATGGCAATTGCTGATAAATGGATTGA
1659 ATCGGCTGCATATGGCAATTGCTGATAAATGGATTGA 1970      1980      1990
1958 GGGTGATATTGTTCATACACTGACAAATAGAAGATGG
1957 GGGTGATATTGTTCATACACTGACAAATAGAAGATGG
1959 GGGTGATATTGTTCATACACTGACAAATAGAAGATGG
1734 GGGTGATATTGTTCATACACTGACAAATAGAAGATGG
1729 GGGTGATATTGTTCATACACTGACAAATAGAAGATGG 2040      2050      2060
2028 GATCAAGCTCTAGTCGGTGATAAAACTATAGCATTCT
2027 GATCAAGCTCTAGTCGGTGATAAAACTATAGCATTCT
2029 GATCAAGCTCTAGTCGGTGATAAAACTATAGCATTCT
1804 GATCAAGCTCTAGTCGGTGATAAAACTATAGCATTCT
1799 GATCAAGCTCTAGTCGGTGATAAAACTATAGCATYCT
```

Fig. 10 Sheet 12

Fig. 10 SHEET 11

```
         1790       1800      1810       1820
CTTATTCATGGGCTTTTCCCAGATGCAATTACC  10con. seq
CTTATTCATAGGCTTTTCCCAGATGCAATTACC  11con. seq
CTTATTCATGGGCTTTTCCCAGATGCAATTACC  19con. seq
CTTATTCATGGGCTTTTCCCAGATGCAATTACC  86CON. SEQ
CTTATTCACGGGCTTTTCCCAGATGCAATTACC  pcrsbe2con. seq 1860       1870      1880       1890
TTCCCGTTCAAGATGGGGGTGTTGGCTTTGACT  10con. seq
TTCCCGTTCAAGATGGGGGTGTTGGCTTTGACT  11con. seq
TTCCCGTCCAAGAGGGGGGTGTTGGCTTTGACT  19con. seq
TTCCCGTTCAAGATGGGGGTGTTGGCTTTGACT  86CON. SEQ
TTCCCGTTCAAGATGGGGGTGTTGGCTTTGACT  pcrsbe2con. seq 1930       1940      1950       1960
GTTGCTCAAGAAACGGGATGAGGATTGGAGAGT  10con. seq
GTTGCTCAAGAAACGGGATGAGGATTGGAGAGT  11con. seq
GTTGCTCAAGAAACGGGATGAGGATTGGAGAGT  19con. seq
GTTGCTCAAGAAACGGGATGAGGATTGGAGAGT  86CON. SEQ
GTTGCTCAAGAAACGGGATGAGGATTGGAGAGT  pcrsbe2con. seq 2000       2010      2020       2030
TCGGAAAAGTGTGTTTCATACGCTGAAAGTCAT  10con. seq
TCGGAAAAGTGTGTTTCATACGCTGAAAGTCAT  11con. seq
TCGGAAAAGTGTGTTTCATACGCTGAAAGTCAT  19con. seq
TCGGAAAAGTGTGTTTCATACGCTGAAAGTCAT  86CON. SEQ
TCGGAAAAGTGTGTTTCATMCGCTGAAAGTCAT  pcrsbe2con. seq 2070       2080      2090       2100
GGCTGATGGACAAGGATATGTATGATTTTATGG  10con. seq
GGCTGATGGACAAGGATATGTATGATTTTATGG  11con. seq
GGCTGATGGACAAGGATATGTATGATTTTATGG  19con. seq
GGCTGATGGACAAGGATATGTATGATTTTATGG  86CON. SEQ
GGCTGATGGACAAGGATATGTATGATTTTATGG  pcrsbe2con. seq
```

Fig. 10

```
                  2110  *   2120        2130
2098  CTCTGGATAGACCGTCAACATCATTAATAGATCGTGG
2097  CTCTGGATAGACCGCCAACATCATTAATAGATCGTGG
2099  CTCTGGATAGACCGTCAACATCATTAATAGATCGTGG
1874  CTCTGGATAGACCGCCAACATCATTAATAGATCGTGG
1869  CTCTGGATAGACCGYCAACAYCATTAATAGATCGTGG
                     *

2180        2190        2200
2168  TATGGGATTAGGAGGAGAAGGGTACCTAAATTTCATG
2167  TATGGGATTAGGAGGAGAAGGGTACCTAAATTTCATG
2169  TATGGGATTAGGAGGAGAAGGGTACCTAAATTTCATG
1944  TATGGGATTAGGAGGAGAAGGGTACCTAAATTTCATG
1939  TATGGGATTAGGAGGAGAAGGGTACCTAAATTTCATG

2250  *   2260        2270
2238  TTCCCTAGGGCTGAACAACACCTCTCTGATGGCTCAG
2237  TTCCCTAGGGCTGAGCCACACCTTTCTGATGGCTCAG
2239  TTCCCTAGGGCTGAACAACACCTCTCTGATGGCTCAG
2014  TTCCCTAGGGCTGAACAACACCTCTCTGATGACTCAG
2009  TTCCCTAGGGCTGARCAACACCTCTCTGATGGCTCAG
                     *

2320        2330        2340
2308  GCAGACGGAGATTTGACCTGGGAGATGCAGAATATTT
2307  GCAGACGGAGATTTGACCTGGGAGATGCAGAATATTT
2309  GCAGACGGAGATTTGACCTGGGAGATGCAGAATATTT
2084  GCAGACGGAGATTTGACCTGGGAGATGCAGAATATTT
2079  GCAGACGGAGATTTGACCTGGGAGATGCAGAATATTT 2390        2400        2410
2378  TATGCAGTATCTTGAAGATAAATATGAGTTTATGACT
2377  TATGCAGTATCTTGAAGATAAATATGAGTTTATGACT
2379  TATGCAGTATCTTGAAGATAAATATGAGTTTATGACT
2154  TATGCAGTATCTTGAAGATAAATATGAGTTTATGACT
2149  TATGCAGTATCTTGAAGATAAATATGAGTTTATGACT
```

Fig. 10 Sheet 14

Fig. 10 SHEET 13

```
        2140      2150      2160      2170
         |         |         |         |
GATAGCATTACACAAGATGATTAGGCTTGTAAC  10con. seq
GATAGCATTGCACAAGATGATTAGGCTTGTAAC  11con. seq
GATAGCATTGCACAAGATGATTAGGCTTGTAAC  19con. seq
GATAGCATTGCACAAGATGATTAGGCTTGTAAC  86CON. SEQ
GATAGCATTGCACAAGATGATTAGGCTTGTAAC  pcrsbe2con. seq 2210      2220      2230      2240
         |         |         |         |
GGAAATGAATTCGGCCACCCTGAGTGGATTGAT  10con. seq
GGAAATGAATTCGGCCACCCTGAGTGGATTGAT  11con. seq
GGAAATGAATTCGGCCACCCTGAGTGGATTGAT  19con. seq
GGAAATGAATTCGGCCACCCTGAGTGGATTGAT  86CON. SEQ
GGAAATGAATTCGGCCACCCTGAGTGGATTGAT  pcrsbe2con. seq 2280      2290      2300      2310
         |         |         |         |
TAATTCCCAGAAACCAATTCAGTTATGATAAAT  10con. seq
TAATTCCCGGAAACCAATTCAGTTATGATAAAT  11con. seq
TAATCCCCGGAAACCAATTCAGTTATGATAAAT  19con. seq
TAATTCCCGGAAACCAATTCAGTTATGATAAAT  86CON. SEQ
TAATTCCCGGAAACCAATTCAGTTATGATAAAT  pcrsbe2con. seq 2350      2360      2370      2380
         |         |         |         |
AAGATACCGTGGGTTGCAAGAATTTGACCGGGC  10con. seq
AAGATACCATGGGTTACAAGAATTTGACTGGGC  11con. seq
AAGATACCGTGGGTTGCAAGAATTTGACCGGCC  19con. seq
AAGATACCGTGGGTTGCAAGAATTTGACCGGGC  86CON. SEQ
AAGATACCATGGGTTGCAAGAATTTGACCGGGC  pcrsbe2con. seq 2420      2430      2440      2450
         |         |         |         |
TCAGAACACCAGTTCATATCACGAAAGGATGAA  10con. seq
TCAGAACACCAGTTCATATCACGAAAGGATGAA  11con. seq
TCAGAACACCAGTTCATATCACGAAAGGATGAA  19con. seq
TCAGAACACCAGTTCATATCACGAAAGGATGAA  86CON. SEQ
TCAGAACACCAGTTCATATCACGAAAGGATGAA  pcrsbe2con. seq
```

Fig. 10 SHEET 14

```
                    2460         2470    *  2480
        2448  GGAGATAGGATGATTGTATTTGAAAAAGGAAACCTAG
        2447  GGAGATAGGATGATTGTATTTGAAAGAGGAAACCTAG
        2449  GGAGATAGGATGATTGTATTTGAAAAAGGAAACCTAG
        2224  GGAGATAGGATGATTGTATTTGAAAAAGGAAACCTAG
        2219  GGAGATAGGATGATTGTATTTGAAARAGGAAACCTAG
                                          *
                    2530         2540         2550
        2518  ATTCAGACTATCGCATAGGCTGCCTGAAGCCTGGAAA
        2517  ATTCAGACTATCGCATAGGCTGCCTGAAGCCTGGAAA
        2519  ATTCAGACTATCGCATAGCCTGCCTGAAGCCTGGAAA
        2294  ATTCAGACTATCGCATAGGCTGCCTGAAGCCTGGAAA
        2289  ATTCAGACTATCGCATAGGCTGCCTGAAGCCTGGAAA 2600         2610         2620
        2588  TTTTGGTGGCTTCGGGAGAATTGATCATAATGCCGAA
        2587  TTTTGGTGGCTTCGGGAGAATTGATCATAATGCCGAA
        2589  TTTTGGTGGCTTCGGGAGAATTGATCATAATGCCGAA
        2364  TTTTGGTGGCTTCGGGAGAATTGATCATAATGCCGAA
        2359  TTTTGGTGGCTTCGGGAGAATTGATCATAATGCCGAA 2670         2680      * 2690
        2658  CCTCGTTCAATTATGGTGTATGCACCTAGTAGAACAG
        2657  CCTTGTTCAATTATGGTGTATGCACCTAGTAGAACAG
        2659  CCTCGTTCAATTATGGTGTATGCACCTTGTAAAACAG
        2434  CCTCGTTCAATTATGGTGTATGCACCTTGTAGAACAG
        2429  CCTCGTTCAATTATGGTGTATGCACCTAGTAGAACAG
                                          *
                    2740         2750         2760
        2722  ------AAGAAGAAGAAGAAGAAGTAGCAGTAGT
        2722  -----------------------AGAAGTAGCAGTAGT
        2729  AAGAAGAAGAAGAAGAAGAAGAAGTAGCAGCAGT
        2501  AAGAAGAAGAAGAAGAAGAAGAAGTAGCAGTAGT
        2499  NAGAAGAAGAAGAAGAAN---------------
```

Fig. 10 Sheet 16

Fig. 10 SHEET 15

```
      2490      2500      2510    ҈   2520
TTTTTGTCTTTAATTTTCACTGGACAAAAGGCT   10con. seq
TTTTCGTCTTTAATTTTCACTGGACAAATAGCT   11con. seq
TTTTTGTCTTTAATTTTCACTGGACAAAAAGCT   19con. seq
TTTTTGTCTTTAATTTTCACTGGACAAAAAGCT   86CON. SEQ
TTTTTGTCTTTAATTTTCACTGGACAAATAGCT   pcrsbe2con. seq
                                  ҈

2560      2570      2580      2590
ATACAAGGTTGCCTTGGACTCAGATGATCCACT   10con. seq
ATACAAGGTTGTCTTGGACTCAGATGATCCACT   11con. seq
ATACAAGGTTGCCTTGGACTCAGATGATCCACT   19con. seq
ATACAAGGTTGCCTTGGACTCAGATGATCCACT   86CON. SEQ
ATACAAGGTTGGCTTGGACTCAGATGATCCACT   pcrsbe2con. seq 2630    ҈ 2640   ҈ 2650      2660
TATTTCACCTTTGAAGGATGGTATGATGATCGT   10con. seq
TATTTCACCTCTGAAGGATCGTATGATGATCGT   11con. seq
TATTTCACCTTTGAAGGATGGTATGATGATCGT   19con. seq
TATTTCACCTTTGAAGGATGGTATGATGATCGT   86CON. SEQ
TATTTCACCTCTGAAGGATCGTATGATGATCGT   pcrsbe2con. seq
             ҈         ҈

2700      2710      2720      2730
CAGTGGTCTATGCACTAGTAGACAAAG----   10con. seq
CAGTGGTCTATGCACTAGTAGACAAACT---   11con. seq
CAGTGGTCTATGCACTAGTAGACAAAGAAGAAG   19con. seq
CAGTGGTCTATGCACTAGTAGACAAAG--AAG   86CON. SEQ
CAGTGGTCTATGCACTAGTAGACAAANTAGAAG   pcrsbe2con. seq 2770      2780      2790      2800
AGAAGAAGTAGTAGTAGAAGAAGAATGAACGAA   10con. seq
AGAAGAACCCATTG------AAGAATGAACGAA   11con. seq
AGAAGAAGTAGTAGTAGAAGAAGAATGAACGAA   19con. seq
AGAAGAAGTAGTAGTAGAAGAAGAATGAACGAA   86CON. SEQ
-----------CCGNNGAAGAAT--------   pcrsbe2con. seq
```

Fig. 10

```
                    2810        2820       2830
2786  CTTGTGATCGCGTTGAAAGATTTGAACGCCACATAGA
2764  CTTGTGATCGCGTTGAAAGATTTGAACGTTACTTGG-
2799  CTTGTGATCGCGTTGAAAGATTTGAACGCTACATAGA
2571  CTTGTG
2529  ------------------------------------

2880        2890       2900
2856  CTTGGCGGAATTTCATGTGACAACA-GGTTTGCAATT
2829  CTTGGCGGAATTGCATGTGACAACAAGGTTTGCAGTT
2869  CTTGGCGGAATTTCATGTGACACAA-GGTTTGCAATT
2576  
2529  ------------------------------------

2950        2960       2970
2925  GAGATGAAGTGCTGAACAAAAACATATGTAAAATCGA
2899  GAGATGAAGTGCTGAACAAA--CATATGTAAAATCGA
2938  GAGATGAAGTGCTGAACAAA--CATATGTAAAATCGA
2576  
2529  ------------------------------------

3020       3030
2995  CCTGCAG------------------CC
2967  CCTGCAG------------------CC
3006  CCTGCAGGCCGGGGGACCCCTTAGTTCT
2576  
2529  ---------------------------T
```

Fig. 10 Sheet 18

Fig. 10 SHEET 17

```
             2840       2850       2860       2870
GCTTCTTGACGTATCTGGCAATATTGCATTAGT  10con. seq
--TCATCCACATA--GAGCTTCTTGACATCAGT  11con. seq
GCTTCTTGACGTATCTGGCAATATTGCATCAGT  19con. seq
                                   86CON. SEQ
-------------------------------    pcrsbe2con. seq 2910       2920       2930       2940
CTTTCCACTATTAGTAGTGCAACGATATACGCA  10con. seq
CTTTCCACTATTAGTAGTCCACCGATATACGCA  11con. seq
CTTTCCACTATTAGTAGTGCAACGATATACGCA  19con. seq
                                   86CON. SEQ
-------------------------------    pcrsbe2con. seq 2980       2990       3000       3010
TGAATTTATGTCGAATGCTGGGACGATCGAATT  10con. seq
TGAATTTATGTCGAATGCTGGGACGATCGAATT  11con. seq
TGAATTTATGTCGAATGCTGGGACGATCGAATT  19con. seq
                                   86CON. SEQ
-------------------------------    pcrsbe2con. seq
```

10con. seq
                                   11con. seq
                                   19con. seq
                                   86CON. SEQ
                                   pcrsbe2con. seq

Fig. 10 SHEET 18

```
                                              NcoI
                                              BstXI
TCATTAAAGAGGAGAAATTAACTATGAGAGGATCTCACCATCACCATCACCATGGGATCT    60
----+----|----+----|----+----|----+----|----+----|----+----|
AGTAATTTCTCCTCTTTAATTGATACTCTCCTAGAGTGGTAGTGGTAGTGGTACCCTAGA
                       M  R  G  S  H  H  H  H  H  H  G  I
                          EcoRI

TGGCTGAAAAGTCTTCTTACAATTCCGAATTCCGACCTTCTACAGTTGCAGCATCGGGGA    120
----+----|----+----|----+----|----+----|----+----|----+----|
ACCGACTTTTCAGAAGAATGTTAAGGCTTAAGGCTGGAAGATGTCAACGTCGTAGCCCCT
 L  A  E  K  S  S  Y  N  S  E  F  R  P  S  T  V  A  A  S  G

AAGTCCTTGTGCCTGGAACCCAGAGTCTCCTCATCCTCAACAACCAATTTGAGT        180
----+----|----+----|----+----|----+----|----+----|----+----|
TTCAGGAACACGGACCTTGGGTCTCAGAGGAGTAGGAGTTGTTGGTTAAACTCA
 K  V  L  V  P  G  T  Q  S  D  S  S  S  S  T  N  Q  F  E

TCACTGAGACATCTCCAGAAAATTCCCCAGCATCAACTGATGTAGATAGTTCAACAATGG    240
----+----|----+----|----+----|----+----|----+----|----+----|
AGTGACTCTGTAGAGGTCTTTTAAGGGGTCGTAGTTGACTACATCTATCAAGTTGTTACC
 F  T  E  T  S  P  E  N  S  P  A  S  T  D  V  D  S  S  T  M
```

Fig. 12 SHEET 1

Fig. 12
SHEET 2

```
AACACGCTAGCCAGATTAAAACTGAGAACGATGACGTTGAGCCGTCAAGTGATCTTACAG
                                                              300
TTGTGCGATCGGTCTAATTTTGACTCTTGCTACTGCAACTCGGCAGTTCACTAGAATGTC
 E  H  A  S  Q  I  K  T  E  N  D  D  V  E  P  S  S  D  L  T

GAAGTGTTGAAGAGCTGGATTTTGCTTCATCACTACAACTACAAGAAGGTGGTAAACTGG
                                                              360
CTTCACAACTTCTCGACCTAAAACGAAGTAGTGATGTTGATGTTCTTCCACCATTTGACC
 G  S  V  E  E  L  D  F  A  S  S  L  Q  L  Q  E  G  G  K  L

AGGAGTCTAAAACATTAAATACTTCTGAAGAGACAATTATTGATGAATCTGATAGGATCA
                                                              420
TCCTCAGATTTTGTAATTTATGAAGACTTCTCTGTTAATAACTACTTAGACTATCCTAGT
 E  E  S  K  T  L  N  T  S  E  E  T  I  I  D  E  S  D  R  I

GAGAGAGGGGGCATCCCCTCCACCTGGGACTTGGTCAGAAGATTTATGAAATAGACCCCTTT
                                                              480
CTCTCTCCCCGTAGGGGAGGTGGACCCTGAACCAGTCTTCTAAATACTTTATCTGGGGAAA
 R  E  R  G  I  P  P  P  G  L  G  Q  K  I  Y  E  I  D  P  L
                         Hinc II TGACAAACTATCGTCAACACCTTGATTACACAGTATTCACAGTACAAGAAACTGAGGAGG
                                                              540
ACTGTTTGATAGCAGTTGTGGAACTAATGTGTCATAAGTGTCATGTTCTTTGACTCCCTCC
 L  T  N  Y  R  Q  H  L  D  Y  R  Y  S  Q  Y  K  K  L  R  E
```

HinD III

```
CAATTGACAAGTATGAGGGTTTGGAAGCTTTTTCTCGTGGTTATGAAAAAATGGGTT
---+---------+---------+---------+---------+---------+ 600
GTTAACTGTTCATACTCCCCAAACCTTCGAAAAGAGCACCAATACTTTTTACCCAA
 A  I  D  K  Y  E  G  G  L  E  A  F  S  R  G  Y  E  K  M  G
```

Pvu II

```
TCACTCGTAGTGTCTACAGGTATCACTTACCGTGAGTGGGCTCCTGGTGCCCAGTCAGCTG
---+---------+---------+---------+---------+---------+ 660
AGTGAGCATCACAGATGTCCATAGTGAATGGCACTCACCCGAGGACCACGGGTCAGTCGAC
 F  T  R  S  A  T  G  I  T  Y  R  E  W  A  P  G  A  Q  S  A
```

```
CCCTCATTGGAGATTTCAACAATTGGGACGCAAATGCTGACATTATGACTCGGAATGAAT
---+---------+---------+---------+---------+---------+ 720
GGGAGTAACCTCTAAAGTTGTTAACCCTGCGTTTACGACTGTAATACTGAGCCTTACTTA
 A  L  I  G  D  F  N  W  D  A  N  A  D  I  M  T  R  N  E
```

```
TTGGTGTCTGGGAGATTTTTCTGCCAAAATAATGTGGATGGTTCTCCTGCAATTCCTCATG
---+---------+---------+---------+---------+---------+ 780
AACCACAGACCCTCTAAAAAGACGGTTTATTACACCTACCAAGAGGACGTTAAGGAGTAC
 F  G  V  W  E  I  F  L  P  N  N  V  D  G  S  P  A  I  P  H
```

Fig 12
SHEET 3

```
SnaBI
GGTCCAGAGTGAAGATACGTAGGACACTCCATCAGGTGTTAAGGATTCCATTCCTGCTT
                                                              840
CCAGGTCTCACTTCTATGCATACCGTGAGGTAGTCCACAATTCCTAAGGTAAGGACGAA
 G  S  R  V  K  I  R  M  D  T  P  S  G  V  K  D  S  I  P  A

GGATCAACTACTCTTCACAGCTTCCTGATGAAATTCCATATAATGGAATATATTATGATC
                                                              900
CCTAGTTGATGAGAAGTGTCGAAGGACTACTTTAAGGTATATTACCTTATATAATACTAG
 W  I  N  Y  S  Q  L  P  D  E  I  P  Y  N  G  I  Y  Y  D

CACCCGAAGAGGAGGTATATCTTCCAACACCCACGGCCAAAGAAACCAAAGTCGCTGA
                                                              960
GTGGGCTTCTCCTCCATATAGAAGGTTGTGGGTGCCGGTTTCTTTGGTTTCAGGACT
 P  P  E  E  E  R  Y  I  F  Q  H  P  R  P  K  K  P  K  S  L

GAATATATGAATCTCATATATTGGAATGAGTAGTCCGGAGCCTAAAATTAACTCATACGTGA
                                                              1020
CTTATATACTTAGAGTATAACCTTACTCATCAGGCCTCGGATTTAATTGAGTATGCACT
 R  I  Y  E  S  H  I  G  M  S  S  P  E  P  K  I  N  S  Y  V
```

Fig. 12 SHEET 4

Fig. 12
SHEET 5

```
        Xmn I                    HinD III
ATTTAGAGATGAAGTTCTTCCTCGCATAAAAAAAGCTTGGGTACAATGCGGTGCAAATTA
                                                              1080
TAAATCTCTACTTCAAGAAGGAGCGTATTTTTTCGAACCCATGTTACGCCACGTTTAAT
 N  F  R  D  E  V  L  P  R  I  K  K  L  G  Y  N  A  V  Q  I

TGGCTATTCAAGAGCATTCTTATTATGCTAGTTTTGGTTATCATGTCACAAATTTTTTG
                                                              1140
ACCGATAAGTTCTCGTAAGAATAATACGATCAAAACCAATAGTACAGTGTTTAAAAAAC
 M  A  I  Q  E  H  S  Y  Y  A  S  F  G  Y  H  V  T  N  F  F

CACCAAGCAGCCGTTTTGGAACGCCCGACGACCTTAAGTCTTTGATTGATAAAGCTCATG
                                                              1200
GTGGTTCGTCGGCAAAACCTTGCGGGCTGCTGGAATTCAGAAACTAACTATTTCGAGTAC
 A  P  S  S  R  F  G  T  P  D  D  L  K  S  L  I  D  K  A  H

Nsi I
AGCTAGGAATTGTTGTTCTCATGGACATTGTTCACAGCCATGCATCAAATAATACTTTAG
                                                              1260
TCGATCCTTAACAACAAGAGTACCTGTAACAAGTGTCGGTACGTAGTTTATTATGAAATC
 E  L  G  I  V  V  L  M  D  I  V  H  S  H  A  S  N  N  T  L
```

```
                                     Sac I
ATGGACTGAACATGTTTGACGGCACCGATAGTTGTTACTTTCACTCTGGAGCTCGTGGTT
----------+---------+---------+---------+---------+---------+  1320
TACCTGACTTGTACAAACTGCCGTGGCTATCAACAATGAAAGTGAGACCTCGAGCACCAA
 D  G  L  N  M  F  D  G  T  D  S  C  Y  F  H  S  G  A  R  G

ATCATTGGATGTGGGATTCCCGCCTTTTAACTATGGAAACTGGGAGGTACTTAGGTATC
----------+---------+---------+---------+---------+---------+  1380
TAGTAACCTACACCCTAAGGGCGGAAAATTGATACCTTTGACCCTCCATGAATCCATAG
 Y  H  W  M  D  S  R  L  F  N  Y  G  N  W  E  V  L  R  Y

TTCTCTCAAATGCGAGATGGGTGGTTGGATGAGTTCAAATTTGATGGATTTAGATTTGATG
----------+---------+---------+---------+---------+---------+  1440
AAGAGAGTTTACGCTCTACCACCAACCTACTCAAGTTTAAACTACCTAAATCTAAACTAC
 L  L  S  N  A  R  W  W  L  D  E  F  K  F  D  G  F  R  F  D

GTGTGACATCAATGATGTATACTCACCACGGATTATCGGTGGGATTCACTGGGAACTACG
----------+---------+---------+---------+---------+---------+  1500
CACACTGTAGTTACTACATATGAGTGGTGCCTAATAGCCACCCTAAGTGACCCTTGATGC
 G  V  T  S  M  M  Y  T  H  H  G  L  S  V  G  F  T  G  N  Y
```

Fig. 12
SHEET 6

Fig 12
SHEET 7

```
                                          Hinc II
AGGAATACTTTGGACTCGCAACTGATGTCTGTTGTATCTGATGCTGGTCAACG   1560
TCCTTATGAAACCTGAGCGTTGACTACACCTACGACAACACATAGACTACCAGTTGC
  E  E  Y  F  G  L  A  T  D  V  D  A  V  V  Y  L  M  L  V  N ATCTTATTCATGGGCTTTTCCCAGATGCAATTACCATTGGTGAAGATGTTAGCGGAATGC   1620
TAGAATAAGTACCCGAAAAGGGTCTACGTTAATGGTAACCACTTCTACAATCGCCTTACG
  D  L  I  H  G  L  F  P  D  A  I  T  G  E  D  V  S  G  M CGACATTTTGTATTCCCGTTCAAGATGGGGGTGTTGGCTTTGACTATCGGCTGCATATGG   1680
GCTGTAAAACATAAGGGCAAGTTCTACCCCCACAACCGAAACTGATAGCCGACGTATACC
  P  T  F  C  I  P  V  Q  D  G  G  V  G  F  D  Y  R  L  H  M CAATTGCTGATAAATGGATTGAGTTGCTCAAGAAAACGGGATGAGGAGATTGGAGAGTGGGTG   1740
GTTAACGACTATTTACCTAACTCAACGAGTTCTTTGCCCTACTCCTAACCTCTCACCCAC
  A  I  A  D  K  W  I  E  L  L  K  K  R  D  E  D  W  R  V  G ATATTGTTCATACACTGACAAATAGAAGAGGTCGGAAAAGTGTGTTTCATACGCTGAAA   1800
TATAACAAGTATGTGACTGTTTATCTTCTACCAGCCTTTTCACACAAAGTATGCGACTTT
  D  I  V  H  T  L  T  N  R  R  W  S  E  K  C  V  S  Y  A  E
```

Fig 12
SHEET 8

```
GTCATGATCAAGCTCTAGTCGGTGATAAAACTATAGCATTCTGGCTGATGGACAAGGATA
CAGTACTAGTTCGAGATCAGCCACTATTTTGATATCGTAAGACCGACTACCTGTTCCTAT    1860
 S  H  D  Q  A  L  V  G  D  K  T  I  A  F  W  L  M  D  K  D

TGTATGATTTTATGGCTCTGGATAGACCGCCAACATCATTAATAGATCGTGGATAGCAT
ACATACTAAAATACCGAGACCTATCTGGCGGTTGTAGTAATTATCTAGCACCTATCGTA    1920
 M  Y  D  F  M  A  L  D  R  P  P  T  S  L  I  D  R  G  I  A
                                              Asp 718
                                                  Kpn I
TGCACAAGATGATTAGGCTTGTAACTATGGGATTAGGAGGAGAAGGGTACCTAAATTTCA
ACGTGTTCTACTAATCCGAACATTGATACCCTAATCCTCCTCTTCCCATGGATTTAAAGT    1980
 L  H  K  M  I  R  L  V  T  M  G  L  G  G  E  G  Y  L  N  F
       EcoR I
TGGGAAATGAATTCGGCCACCCTGAGTGGATTGATTCCCTAGGGCTGAACAACACCTCT
ACCCTTTACTTAAGCCGGTGGGACTCACCTAACTAAAGGGATCCCGACTTGTGTGGAGA    2040
 M  G  N  E  F  G  H  P  E  W  I  D  F  P  R  A  E  Q  H  L
```

```
CTGATGACTCAGTTATGATAAATGCAGACGGAGATTTG
                                      +2100
GACTACTGAGTCATTAAGGGCCTTTGGTTAAGTCAATACTATTACGTCTGCCTCTAAAC
 S  D  D  S  V  I  P  G  N  Q  F  S  Y  D  K  C  R  R  R  F

ACCTGGGAGATGCAGAATATTTAAGATACCGTGGGTTGCAAGAATTTGACCGGCTATGC
                                      +2160
TGGACCCTCTACGTCTTATAAATTCTATGGCACCCAACGTTCTTAAACTGGCCCGATACG
     Ssp I
 D  L  G  D  A  E  Y  L  R  Y  R  G  L  Q  E  F  D  R  A  M

AGTATCTTGAAGATAAATATGAGTTTATGACTTCAGAACACCAGTTCATATCACGAAAGG
                                      +2220
TCATAGAACTTCTATTTATACTCAAATACTGAAGTCTTGTGGTCAAGTATAGTGCTTTCC
 Q  Y  L  E  D  K  Y  E  F  M  T  S  E  H  Q  F  I  S  R  K

ATGAAGGAGATAGGATGATTGTATTTGAAAAAGGAAACCTAGTTTTTGTCTTTAATTTTC
                                      +2280
TACTTCCTCTATCCTACTAACATAAACTTTTTCCTTTGGATCAAAACAGAAATTAAAAG
 D  E  G  D  R  M  I  V  F  E  K  G  N  L  V  F  V  F  N  F

ACTGGACAAAAAGCTATTCAGACTATCGCATAGGCTGCCTGAAGCCTGGAAAATACAAGG
                                      +2340
TGACCTGTTTTTCGATAAGTCTGATAGCGTATCCGACGGACTTCGGACCTTTATGTTCC
 H  W  T  K  S  Y  S  D  Y  R  I  G  C  L  K  P  G  K  Y  K
```

Fig. 12
SHEET 9

```
TTGCCTTGGACTCAGATGATCCACTTTTGGTGGCTTCGGGAGAATTGATCATAATGCCG
                                                           2400
AACGGAACCTGAGTCTACTAGGTGAAAAACCACCGAAGCCCTCTTAACTAGTATTACGGC
 V  A  L  D  S  D  D  P  L  F  G  G  F  G  R  I  D  H  N  A

SspI
AATATTTCACCTTTGAAGGATGGTATGATGATCGTCCTCGTTCAATTATGGTGTATGCAC
                                                           2460
TTATAAAGTGGAAACTTCCTACCATACTACTAGCAGGAGCAAGTTAATACCACATACGTG
 E  Y  F  T  F  E  G  W  Y  D  D  R  P  R  S  I  M  V  Y  A

CTTGTAGAACAGCAGTGGTCTATGCACTAGTAGACAAAGAAGAAGAAGAAGAAGAAGAAG
                                                           2520
GAACATCTTGTCGTCACCAGATACGTGATCATCTGTTTCTTCTTCTTCTTCTTCTTCTTC
 P  C  R  T  A  V  V  Y  Y  A  L  V  D  K  E  E  E  E  E  E

AAGAAGAAGTAGCAGTAGTAGAAGAAGTAGTAGAAGAATGAACGAACTTGTG
                                              ──────▶ 2578
TTCTTCTTCATCGTCATCATCTTCTTCATCATCATCTTCTTACTTGCTTGAACAC
 E  E  E  V  A  V  V  E  E  V  V  E  E  E
```

Fig 12
SHEET 10

SEQUENCE LISTING

<160> NUMBER OF SEQ ID NOS: 43

<210> SEQ ID NO 1
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaggatccgt cgacatcgat aatacgactc actataggga ttttttttttt tttttt        57

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaggatccgt cgacatc                                                    17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gacatcgata atacgac                                                    17

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
catccaacca ccatctcgca                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttgagagaag atacctaagt                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
atgttcagtc catctaaagt                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agaacaacaa ttcctagctc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggggccttga actcagcaat                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgtcccagca ttcgacataa                                              20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cttggatcct tgaactcagc aatttg                                       26

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
taactcgagc aacgcgatca caagttcgt                                    29

<210> SEQ ID NO 12
<211> LENGTH: 3003
<212> TYPE: DNA
<213> ORGANISM: Solanum tuberosum

<400> SEQUENCE: 12
gatggggcct tgaactcagc aatttgacac tcagttagtt acactgccat cacttatcag    60
atctctattt tttctcttaa ttccaaccaa ggaatgaata aaagataga tttgtaaaaa     120
```

-continued

```
ccctaaggag agaagaagaa agatggtgta tacactctct ggagttcgtt ttcctactgt      180
tccatcagtg tacaaatcta atggattcag cagtaatggt gatcggagga atgctaatat      240
ttctgtattc ttgaaaaaac actctctttc acggaagatc ttggctgaaa agtcttctta      300
caattccgaa tcccgacctt ctacaattgc agcatcgggg aaagtccttg tgcctggaat      360
ccagagtgat agctcctcat cctcaacaga tcaatttgag ttcgctgaga catctccaga      420
aaattcccca gcatcaactg atgtagatag ttcaacaatg gaacacgcta gccagattaa      480
aactgagaac gatgacgttg agccgtcaag tgatcttaca ggaagtgttg aagagctgga      540
ttttgcttca tcactacaac tacaagaagg tggtaaactg gaggagtcta aaacattaaa      600
tacttctgaa gagacaatta ttgatgaatc tgataggatc agagagaggg gcatccctcc      660
acctggactt ggtcagaaga tttatgaaat agaccccctt ttgacaaact atcgtcaaca      720
ccttgattac aggtattcac agtacaagaa actgagggag gcaattgaca gtatgagggg      780
tggtttggaa gcttttctc gtggttatga agaatgggt ttcactcgta gtgctacagg      840
tatcacttac cgtgagtggg ctcctggtgc ccagtcagct gccctcattg ggatttcaa      900 caattgggac gcaaatgctg actttatgac tcggaatgaa tttggtgtct gagagatttt      960
tctgccaaat aatgtggatg gttctcctgc aattcctcat gggtccgagt gaagatacg      1020 tatgacact ccatcaggtg ttaaggattc cattcctgct ggatcaact actctttaca     1080 gcttcctgat gaaattccat ataatggaat atattatgat ccacccgaag aggagaggta      1140
tatcttccaa cacccacggc caaagaaacc aaagtcggtg agaatatatg aatctcatat      1200
tggaatgagt agtccggagc ctaaaattaa ctcatacgtg aattttagag atgaagttct      1260
tcctcgcata aaaaaagctt gggtacaatg cggtgcaaat tatggctatt caagagcatt      1320
cttattatgc tagttttggt tatcatgtca caaattttttt tgcaccaagc agccgttttg      1380
gaacgcccga cgaccttaag tctttgattg ataaagctca tgagctagga attgttgttc      1440
tcatggacat tgttcacagc catgcatcaa ataatacttt agatggactg aacatgtttg      1500
acggcacaga tagttgttac tttcactctg gagctcgtgg ttatcattgg atgtgggatt      1560
tccgcctctt taactatgga aactgggagg tacttaggta tcttctctca aatgcgagat      1620
ggtggttgga tgagttcaaa tttgatggat ttagattcga tggtgtgaca tcaatgatgt      1680
gtactcacca cggattatcg gtgggattca ctgggaacta cgaggaatac tttggactcg      1740
caactgatgt ggatgctgtt gtgtatctga tgctggtcaa cgatcttatt catgggcttt      1800
tcccagatgc aattaccatt ggtgaagatg ttagcggaat gccgacattt tgtgttcccg      1860
ttcaagatgg gggtgttggc tttgactatc ggctgcatat ggcaattgct gataaatgga      1920
ttgagttgct caagaaacgg gatgaggatt ggagagtggg tgatattgtt catacactga      1980
caaatagaag atggtcggaa aagtgtgttt catacgctga aagtcatgat caagctctag      2040
tcggtgataa aactatagca ttctggctga tggacaagga tatgtatgat tttatggctc      2100
tggatagacc gtcaacatca ttaatagatc gtgggatagc attacacaag atgattaggc      2160
ttgtaactat gggattagga ggagaagggt acctaaattt catgggaaat gaattcggcc      2220
accctgagtg gattgatttc cctagggctg aacaacacct ctctgatggc tcagtaattc      2280
ccagaaacca attcagttat gataaatgca gacggagatt tgacctggga gatgcagaat      2340
atttaagata ccgtgggttg caagaattgg accgggctat gcagtatctt gaagataaat      2400
atgagtttat gacttcagaa caccagttca tatcacgaaa ggatgaagga gataggatga      2460
```

```
ttgtatttga aaaaggaaac ctagttttg tctttaattt tcactggaca aaaggctatt      2520
cagactatcg cataggctgc ctgaagcctg gaaaatacaa ggttgccttg gactcagatg      2580
atccactttt tggtggcttc gggagaattg atcataatgc cgaatatttc acctttgaag      2640
gatggtatga tgatcgtcct cgttcaatta tggtgtatgc acctagtaga acagcagtgg      2700
tctatgcact agtagacaaa gaagaagaag aagaagaaga agtagcagta gtagaagaag      2760
tagtagtaga agaagaatga acgaacttgt gatcgcgttg aaagatttga acgccacata      2820
gagcttcttg acgtatctgg caatattgca ttagtcttgg cggaatttca tgtgacaaca      2880
ggtttgcaat tctttccact attagtagtg caacgatata cgcagagatg aagtgctgaa      2940
caaaaacata tgtaaaatcg atgaatttat gtcgaatgct gggacgatcg aattcctgca      3000
gcc                                                                    3003

<210> SEQ ID NO 13
<211> LENGTH: 2975
<212> TYPE: DNA
<213> ORGANISM: Solanum tuberosum

<400> SEQUENCE: 13
ttgatgggcc ttgaactcag caatttgaca ctcagttagt tacactccta tcacttatca        60
gatctctatt ttttctctta attccaacca ggggaatgaa taaaaggata gatttgtaaa       120
aaccctaagg agagaagaag aaagatggtg tatatactct ctggagttcg ttttcctact       180
gttccatcag tgtacaaatc taatggattc agcagtaatg gtgatcggag gaatgctaat       240
gtttctgtat tcttgaaaaa gcactctctt tcacggaaga tcttggctga aaagtcttct       300
tacaattccg aattccgacc ttctacagtt gcagcatcgg ggaaagtcct tgtgcctgga       360
acccagagtg atagctcctc atcctcaaca gaccaatttg agttcactga acatctcca       420 gaaaattccc cagcatcaac tgatgtagat agttcaacaa tggaacacgc tagccagatt       480
aaaactgaga acgatgacgt tgagccgtca agtgatctta caggaagtgt tgaagagctg       540
gattttgctt catcactaca actcaagaa ggtggtaaac tggaggagtc taaaacatta       600
aatacttctg aagagacaat tattgatgaa tctgatagga tcagagagag gggcatccct       660
ccacctggac ttggtcagaa gatttatgaa atagaccccc ttttgacaaa ctatcgtcaa       720
caccttgatt acaggtattc acagtacaag aaactgaggg aggcaattga caagtatgag       780
ggtggtttgg aagcttttct cgtgggttatg aaaaaatggg tttcactcgt agtgctacag       840
gtatcactta ccgtgagtgg gctcctggtg cccagtcagc tgccctcatt ggagatttca       900
acaattggga cgcaaatgct gacattatga ctcggaatga atttggtgtc tgggagattt       960
ttctgccaaa taatgtggat ggttctcctg caattcctca tgggtccaga gtgaagatac      1020
gtatggacac tccatcaggt gttaaggatt ccattcctgc ttggatcaac tactctttac      1080
agcttcctga tgaaattcca tataatgaa tatattatga tccacccgaa gaggagaggt      1140
atatcttcca acacccacgg ccaaagaaac caagtcgct gagaatatat gaatctcata      1200
ttggaatgag tagtccggag cctaaaatta actcatacgt gaattttaga gatgaagttc      1260
ttcctcgcat aaaaaagctt gggtacaatg cgctgcgaat tatggctatt caagagcatt      1320
cttattatgc tagttttggt tatcatgtca caattttttt tgcaccaagc agccgttttg      1380
gaacgcccga cgaccttaag tcttcgattg ataaagctca tgagctagga attgttgttc      1440
tcatggacat cgttcacagc catgcatcaa ataaatcttt agatggactg aacatgtttg      1500
acggcaccga tagttgttac tttcactctg gagctcgtgg ttatcattgg atgtgggatt      1560
```

-continued

```
ccgcctcttt aactatggaa actgggaggt acttaggtat cttctctcaa atgcgagatg    1620
gtggttggat gagttcaaat ttgatggatt tagattcgat ggtgtgacat caatgatgta    1680
tactcaccac ggattatcgg tgggattcac tgggaactac gaggaatact ttggactcgc    1740
aactgatgtg gatgctgttg tgtatctgat gctggtcaac gatcttattc ataggctttt    1800
cccagatgca attaccattg gtgaagatgt tagcggaatg ccgacatttt gtattcccgt    1860
tcaagatggg ggtgttggct tgactatcg gctgcatatg gcaattgctg ataaatggat    1920
tgagttgctc aagaaacggg atgaggattg gagagtgggt gatattgttc atacactgac    1980
aaatagaaga tggtcggaaa agtgtgtttc atacgctgaa agtcatgatc aagctctagt    2040
cggtgataaa actatagcat tctggctgat ggacaaggat atgtatgatt ttatggctct    2100
ggatagaccg ccaacatcat aatagatcg tgggatagca ttgcacaaga tgattaggct    2160
tgtaactatg ggattaggag gagaagggta cctaaatttc atgggaaatg aattcggcca    2220
ccctgagtgg attgatttcc ctagggctga gccacacctt tctgatggct cagtaattcc    2280
cggaaaccaa ttcagttatg ataaatgcag acggagattt gacctgggag atgcagaata    2340
tttaagatac catgggttac aagaatttga ctgggctatg cagtatcttg aagataaata    2400
tgagtttatg acttcagaac accagttcat atcacgaaag gatgaaggag ataggatgat    2460
tgtatttgaa agaggaaacc tagttttcgt ctttaattt cactggacaa atagctattc    2520
agactatcgc ataggctgcc tgaagcctgg aaaatacaag gttgtcttgg actcagatga    2580
tccacttttt ggtggcttcg ggagaattga tcataatgcc gaatatttca cctctgaagg    2640
atcgtatgat gatcgtcctt gttcaattat ggtgtatgca cctagtagaa cagcagtggt    2700
ctatgcacta gtagacaaac tagaagtagc agtagtagaa gaacccattg aagaatgaac    2760
gaacttgtga tcgcgttgaa agatttgaac gttacttggt catccacata gagcttcttg    2820
acatcagtct tggcggaatt gcatgtgaca acaaggtttg cagttctttc cactattagt    2880
agtccaccga tatacgcaga gatgaagtgc tgaacaaaca tatgtaaaat cgatgaattt    2940
atgtcgaatg ctgggacgat cgaattcctg cagcc                              2975
```

<210> SEQ ID NO 14
<211> LENGTH: 3033
<212> TYPE: DNA
<213> ORGANISM: Solanum tuberosum
<220> FEATURE:
<221> NAME/KEY: CDS
<222> LOCATION: (96)..(116)
<220> FEATURE:
<221> NAME/KEY: CDS
<222> LOCATION: (145)..(2790)

<400> SEQUENCE: 14

```
ttgatgggc cttgaactca gcaatttgac actcagttag ttacactcct atcacttatc     60
agatctctat tttttctctt aattccaacc aagga atg aat aaa agg ata gat       113
                                        Met Asn Lys Arg Ile Asp
                                        1               5 ttg taaaaccct aaggagagaa gaagaaag atg gtg tat aca ctc tct gga        165
Leu                                 Met Val Tyr Thr Leu Ser Gly
                                                10 gtt cgt ttt cct act gtt cca tca gtg tac aaa tct aat gga ttc agc      213
Val Arg Phe Pro Thr Val Pro Ser Val Tyr Lys Ser Asn Gly Phe Ser
15                  20                  25                  30 agt aat ggt gat cgg agg aat gct aat gtt tct gta ttc ttg aaa aag      261
Ser Asn Gly Asp Arg Arg Asn Ala Asn Val Ser Val Phe Leu Lys Lys
```

```
                    35                  40                  45
cac tct ctt tca cgg aag atc ttg gct gaa aag tct tct tac aat tcc       309
His Ser Leu Ser Arg Lys Ile Leu Ala Glu Lys Ser Ser Tyr Asn Ser
             50                  55                  60 gaa ttc cga cct tct aca gtt gca gca tcg ggg aaa gtc ctt gtg cct       357
Glu Phe Arg Pro Ser Thr Val Ala Ala Ser Gly Lys Val Leu Val Pro
         65                  70                  75 gga acc cag agt gat agc tcc tca tcc aca gac caa ttt gag ttc           405
Gly Thr Gln Ser Asp Ser Ser Ser Ser Thr Asp Gln Phe Glu Phe
     80                  85                  90 act gag aca tct cca gaa aat tcc cca gca tca act gat gta gat agt       453
Thr Glu Thr Ser Pro Glu Asn Ser Pro Ala Ser Thr Asp Val Asp Ser
95                 100                 105                 110 tca aca atg gaa cac gct agc cag att aaa act gag aac gat gac gtt       501
Ser Thr Met Glu His Ala Ser Gln Ile Lys Thr Glu Asn Asp Asp Val
                115                 120                 125 gag ccg tca agt gat ctt aca gga agt gtt gaa gag ctg gat ttt gct       549
Glu Pro Ser Ser Asp Leu Thr Gly Ser Val Glu Glu Leu Asp Phe Ala
            130                 135                 140 tca tca cta caa cta caa gaa ggt ggt aaa ctg gag gag tct aaa aca       597
Ser Ser Leu Gln Leu Gln Glu Gly Gly Lys Leu Glu Glu Ser Lys Thr
        145                 150                 155 tta aat act tct gaa gag aca att att gat gaa tct gat agg atc aga       645
Leu Asn Thr Ser Glu Glu Thr Ile Ile Asp Glu Ser Asp Arg Ile Arg
    160                 165                 170 gag agg ggc atc cct cca cct gga ctt ggt cag aag att tat gaa ata       693
Glu Arg Gly Ile Pro Pro Pro Gly Leu Gly Gln Lys Ile Tyr Glu Ile
175                 180                 185                 190 gac ccc ctt ttg aca aac tat cgt caa cac ctt gat tac agg tat tca       741
Asp Pro Leu Leu Thr Asn Tyr Arg Gln His Leu Asp Tyr Arg Tyr Ser
                195                 200                 205 cag tac aag aaa ctg agg gag gca att gac aag tat gag ggt ggt ttg       789
Gln Tyr Lys Lys Leu Arg Glu Ala Ile Asp Lys Tyr Glu Gly Gly Leu
            210                 215                 220 gaa gcc ttt tct cgt ggt tat gaa aaa atg ggt ttc act cgt agt gct       837
Glu Ala Phe Ser Arg Gly Tyr Glu Lys Met Gly Phe Thr Arg Ser Ala
        225                 230                 235 aca ggt atc act tac cgt gag tgg gct ctt ggt gcc cag tca gct gcc       885
Thr Gly Ile Thr Tyr Arg Glu Trp Ala Leu Gly Ala Gln Ser Ala Ala
    240                 245                 250 ctc att gga gat ttc aac aat tgg gac gca aat gct gac att atg act       933
Leu Ile Gly Asp Phe Asn Asn Trp Asp Ala Asn Ala Asp Ile Met Thr
255                 260                 265                 270 cgg aat gaa ttt ggt gtc tgg gag att ttt ctg cca aat aat gtg gat       981
Arg Asn Glu Phe Gly Val Trp Glu Ile Phe Leu Pro Asn Asn Val Asp
                275                 280                 285 ggt tct cct gca att cct cat ggg tcc aga gtg aag ata cgt atg gac      1029
Gly Ser Pro Ala Ile Pro His Gly Ser Arg Val Lys Ile Arg Met Asp
            290                 295                 300 act cca tca ggt gtt aag gat tcc att cct gct tgg atc aac tac tct      1077
Thr Pro Ser Gly Val Lys Asp Ser Ile Pro Ala Trp Ile Asn Tyr Ser
        305                 310                 315 tta cag ctt cct gat gaa att cca tat aat gga ata cat tat gat cca      1125
Leu Gln Leu Pro Asp Glu Ile Pro Tyr Asn Gly Ile His Tyr Asp Pro
    320                 325                 330 ccc gaa gag gag agg tat atc ttc caa cac cca cgg cca aag aaa cca      1173
Pro Glu Glu Glu Arg Tyr Ile Phe Gln His Pro Arg Pro Lys Lys Pro
335                 340                 345                 350 aag tcg ctg aga ata tat gaa tct cat att gga atg agt agt ccg gag      1221
```

| | | |
|---|---|---|
| Lys Ser Leu Arg Ile Tyr Glu Ser His Ile Gly Met Ser Ser Pro Glu<br>355 360 365 | | |
| cct aaa att aac tca tac gtg aat ttt aga gat gaa gtt ctt cct cgc<br>Pro Lys Ile Asn Ser Tyr Val Asn Phe Arg Asp Glu Val Leu Pro Arg<br>370 375 380 | | 1269 |
| ata aaa aag ctt ggg tac aat gcg ctg caa att atg gct att caa gag<br>Ile Lys Lys Leu Gly Tyr Asn Ala Leu Gln Ile Met Ala Ile Gln Glu<br>385 390 395 | | 1317 |
| cat tct tat tac gct agt ttt ggt tat cat gtc aca aat ttt ttt gca<br>His Ser Tyr Tyr Ala Ser Phe Gly Tyr His Val Thr Asn Phe Phe Ala<br>400 405 410 | | 1365 |
| cca agc agc cgt ttt gga acg ccc gac gac ctt aag tct ttg att gat<br>Pro Ser Ser Arg Phe Gly Thr Pro Asp Asp Leu Lys Ser Leu Ile Asp<br>415 420 425 430 | | 1413 |
| aaa gct cat gag cta gga att gtt gtt ctc atg gac att gtt cac agc<br>Lys Ala His Glu Leu Gly Ile Val Val Leu Met Asp Ile Val His Ser<br>435 440 445 | | 1461 |
| cat gca tca aat aat act tta gat gga ctg aac atg ttt gac tgc acc<br>His Ala Ser Asn Asn Thr Leu Asp Gly Leu Asn Met Phe Asp Cys Thr<br>450 455 460 | | 1509 |
| gat agt tgt tac ttt cac tct gga gct cgt ggt tat cat tgg atg tgg<br>Asp Ser Cys Tyr Phe His Ser Gly Ala Arg Gly Tyr His Trp Met Trp<br>465 470 475 | | 1557 |
| gat tcc cgc ctc ttt aac tat gga aac tgg gag gta ctt agg tat ctt<br>Asp Ser Arg Leu Phe Asn Tyr Gly Asn Trp Glu Val Leu Arg Tyr Leu<br>480 485 490 | | 1605 |
| ctc tca aat gcg aga tgg tgg ttg gat gcg ttc aaa ttt gat gga ttt<br>Leu Ser Asn Ala Arg Trp Trp Leu Asp Ala Phe Lys Phe Asp Gly Phe<br>495 500 505 510 | | 1653 |
| aga ttt gat ggt gtg aca tca atg atg tat att cac cac gga tta tcg<br>Arg Phe Asp Gly Val Thr Ser Met Met Tyr Ile His His Gly Leu Ser<br>515 520 525 | | 1701 |
| gtg gga ttc act ggg aac tac gag gaa tac ttt gga ctc gca act gat<br>Val Gly Phe Thr Gly Asn Tyr Glu Glu Tyr Phe Gly Leu Ala Thr Asp<br>530 535 540 | | 1749 |
| gtg gat gct gtt gtg tat ctg atg ctg gtc aac gat ctt att cat ggg<br>Val Asp Ala Val Val Tyr Leu Met Leu Val Asn Asp Leu Ile His Gly<br>545 550 555 | | 1797 |
| ctt ttc cca gat gca att acc att ggt gaa gat gtt agc gga atg ccg<br>Leu Phe Pro Asp Ala Ile Thr Ile Gly Glu Asp Val Ser Gly Met Pro<br>560 565 570 | | 1845 |
| aca ttt tgt att ccc gtc caa gag ggg ggt gtt ggc ttt gac tat cgg<br>Thr Phe Cys Ile Pro Val Gln Glu Gly Gly Val Gly Phe Asp Tyr Arg<br>575 580 585 590 | | 1893 |
| ctg cat atg gca att gct gat aaa cgg att gag ttg ctc aag aaa cgg<br>Leu His Met Ala Ile Ala Asp Lys Arg Ile Glu Leu Leu Lys Lys Arg<br>595 600 605 | | 1941 |
| gat gag gat tgg aga gtg ggt gat att gtt cat aca ctg aca aat aga<br>Asp Glu Asp Trp Arg Val Gly Asp Ile Val His Thr Leu Thr Asn Arg<br>610 615 620 | | 1989 |
| aga tgg tcg gaa aag tgt gtt tca tac gct gaa agt cat gat caa gct<br>Arg Trp Ser Glu Lys Cys Val Ser Tyr Ala Glu Ser His Asp Gln Ala<br>625 630 635 | | 2037 |
| cta gtc ggt gat aaa act ata gca ttc tgg ctg atg gac aag gat atg<br>Leu Val Gly Asp Lys Thr Ile Ala Phe Trp Leu Met Asp Lys Asp Met<br>640 645 650 | | 2085 |
| tat gat ttt atg gct ctg gat aga ccg tca aca tca tta ata gat cgt<br>Tyr Asp Phe Met Ala Leu Asp Arg Pro Ser Thr Ser Leu Ile Asp Arg<br>655 660 665 670 | | 2133 |

-continued

| | | |
|---|---|---|
| ggg ata gca ttg cac aag atg att agg ctt gta act atg gga tta gga<br>Gly Ile Ala Leu His Lys Met Ile Arg Leu Val Thr Met Gly Leu Gly<br>675 680 685 | | 2181 |
| gga gaa ggg tac cta aat ttc atg gga aat gaa ttc ggc cac cct gag<br>Gly Glu Gly Tyr Leu Asn Phe Met Gly Asn Glu Phe Gly His Pro Glu<br>690 695 700 | | 2229 |
| tgg att gat ttc cct agg gct gaa caa cac ctc tct gat ggc tca gta<br>Trp Ile Asp Phe Pro Arg Ala Glu Gln His Leu Ser Asp Gly Ser Val<br>705 710 715 | | 2277 |
| atc ccc gga aac caa ttc agt tat gat aaa tgc aga cgg aga ttt gac<br>Ile Pro Gly Asn Gln Phe Ser Tyr Asp Lys Cys Arg Arg Arg Phe Asp<br>720 725 730 | | 2325 |
| ctg gga gat gca gaa tat tta aga tac cgt ggg ttg caa gaa ttt gac<br>Leu Gly Asp Ala Glu Tyr Leu Arg Tyr Arg Gly Leu Gln Glu Phe Asp<br>735 740 745 750 | | 2373 |
| cgg cct atg cag tat ctt gaa gat aaa tat gag ttt atg act tca gaa<br>Arg Pro Met Gln Tyr Leu Glu Asp Lys Tyr Glu Phe Met Thr Ser Glu<br>755 760 765 | | 2421 |
| cac cag ttc ata tca cga aag gat gaa gga gat agg atg att gta ttt<br>His Gln Phe Ile Ser Arg Lys Asp Glu Gly Asp Arg Met Ile Val Phe<br>770 775 780 | | 2469 |
| gaa aaa gga aac cta gtt ttt gtc ttt aat ttt cac tgg aca aaa agc<br>Glu Lys Gly Asn Leu Val Phe Val Phe Asn Phe His Trp Thr Lys Ser<br>785 790 795 | | 2517 |
| tat tca gac tat cgc ata gcc tgc ctg aag cct gga aaa tac aag gtt<br>Tyr Ser Asp Tyr Arg Ile Ala Cys Leu Lys Pro Gly Lys Tyr Lys Val<br>800 805 810 | | 2565 |
| gcc ttg gac tca gat gat cca ctt ttt ggt ggc ttc ggg aga att gat<br>Ala Leu Asp Ser Asp Asp Pro Leu Phe Gly Gly Phe Gly Arg Ile Asp<br>815 820 825 830 | | 2613 |
| cat aat gcc gaa tat ttc acc ttt gaa gga tgg tat gat gat cgt cct<br>His Asn Ala Glu Tyr Phe Thr Phe Glu Gly Trp Tyr Asp Asp Arg Pro<br>835 840 845 | | 2661 |
| cgt tca att atg gtg tat gca cct tgt aaa aca gca gtg gtc tat gca<br>Arg Ser Ile Met Val Tyr Ala Pro Cys Lys Thr Ala Val Val Tyr Ala<br>850 855 860 | | 2709 |
| cta gta gac aaa gaa gaa gaa gaa gaa gaa gaa gaa gaa gaa gta<br>Leu Val Asp Lys Glu Glu Glu Glu Glu Glu Glu Glu Glu Glu Val<br>865 870 875 | | 2757 |
| gca gca gta gaa gaa gta gta gta gaa gaa gaa tgaacgaact tgtgatcgcg<br>Ala Ala Val Glu Glu Val Val Val Glu Glu Glu<br>880 885 | | 2810 |
| ttgaaagatt tgaacgctac atagagcttc ttgacgtatc tggcaatatt gcatcagtct | | 2870 |
| tgcggaatt tcatgtgaca caaggtttgc aattctttcc actattagta gtgcaacgat | | 2930 |
| atacgcagag atgaagtgct gaacaaacat atgtaaaatc gatgaattta tgtcgaatgc | | 2990 |
| tgggacgatc gaattcctgc aggccggggg accccttagt tct | | 3033 |

<210> SEQ ID NO 15
<211> LENGTH: 889
<212> TYPE: PRT
<213> ORGANISM: Solanum tuberosum

<400> SEQUENCE: 15

Met Asn Lys Arg Ile Asp Leu Met Val Tyr Thr Leu Ser Gly Val Arg
1               5                   10                  15

Phe Pro Thr Val Pro Ser Val Tyr Lys Ser Asn Gly Phe Ser Ser Asn
                20                  25                  30

Gly Asp Arg Arg Asn Ala Asn Val Ser Val Phe Leu Lys Lys His Ser

```
                35                  40                  45
Leu Ser Arg Lys Ile Leu Ala Glu Lys Ser Ser Tyr Asn Ser Glu Phe
         50                  55                  60

Arg Pro Ser Thr Val Ala Ser Gly Lys Val Leu Val Pro Gly Thr
 65                  70                  75                  80

Gln Ser Asp Ser Ser Ser Ser Thr Asp Gln Phe Glu Phe Thr Glu
                 85                  90                  95

Thr Ser Pro Glu Asn Ser Pro Ala Ser Thr Asp Val Asp Ser Ser Thr
                100                 105                 110

Met Glu His Ala Ser Gln Ile Lys Thr Glu Asn Asp Asp Val Glu Pro
            115                 120                 125

Ser Ser Asp Leu Thr Gly Ser Val Glu Glu Leu Asp Phe Ala Ser Ser
130                 135                 140

Leu Gln Leu Gln Glu Gly Gly Lys Leu Glu Ser Lys Thr Leu Asn
145                 150                 155                 160

Thr Ser Glu Glu Thr Ile Ile Asp Glu Ser Asp Arg Ile Arg Glu Arg
                165                 170                 175

Gly Ile Pro Pro Pro Gly Leu Gly Gln Lys Ile Tyr Glu Ile Asp Pro
            180                 185                 190

Leu Leu Thr Asn Tyr Arg Gln His Leu Asp Tyr Arg Tyr Ser Gln Tyr
            195                 200                 205

Lys Lys Leu Arg Glu Ala Ile Asp Lys Tyr Glu Gly Gly Leu Glu Ala
210                 215                 220

Phe Ser Arg Gly Tyr Glu Lys Met Gly Phe Thr Arg Ser Ala Thr Gly
225                 230                 235                 240

Ile Thr Tyr Arg Glu Trp Ala Leu Gly Ala Gln Ser Ala Ala Leu Ile
                245                 250                 255

Gly Asp Phe Asn Asn Trp Asp Ala Asn Ala Asp Ile Met Thr Arg Asn
            260                 265                 270

Glu Phe Gly Val Trp Glu Ile Phe Leu Pro Asn Asn Val Asp Gly Ser
            275                 280                 285

Pro Ala Ile Pro His Gly Ser Arg Val Lys Ile Arg Met Asp Thr Pro
            290                 295                 300

Ser Gly Val Lys Asp Ser Ile Pro Ala Trp Ile Asn Tyr Ser Leu Gln
305                 310                 315                 320

Leu Pro Asp Glu Ile Pro Tyr Asn Gly Ile His Tyr Asp Pro Pro Glu
                325                 330                 335

Glu Glu Arg Tyr Ile Phe Gln His Pro Arg Pro Lys Lys Pro Lys Ser
            340                 345                 350

Leu Arg Ile Tyr Glu Ser His Ile Gly Met Ser Ser Pro Glu Pro Lys
            355                 360                 365

Ile Asn Ser Tyr Val Asn Phe Arg Asp Glu Val Leu Pro Arg Ile Lys
370                 375                 380

Lys Leu Gly Tyr Asn Ala Leu Gln Ile Met Ala Ile Gln Glu His Ser
385                 390                 395                 400

Tyr Tyr Ala Ser Phe Gly Tyr His Val Thr Asn Phe Phe Ala Pro Ser
                405                 410                 415

Ser Arg Phe Gly Thr Pro Asp Asp Leu Lys Ser Leu Ile Asp Lys Ala
            420                 425                 430

His Glu Leu Gly Ile Val Val Leu Met Asp Ile Val His Ser His Ala
            435                 440                 445

Ser Asn Asn Thr Leu Asp Gly Leu Asn Met Phe Asp Cys Thr Asp Ser
450                 455                 460
```

```
-continued

Cys Tyr Phe His Ser Gly Ala Arg Gly Tyr His Trp Met Trp Asp Ser
465                 470                 475                 480

Arg Leu Phe Asn Tyr Gly Asn Trp Glu Val Leu Arg Tyr Leu Leu Ser
            485                 490                 495

Asn Ala Arg Trp Trp Leu Asp Ala Phe Lys Phe Asp Gly Phe Arg Phe
                500                 505                 510

Asp Gly Val Thr Ser Met Met Tyr Ile His His Gly Leu Ser Val Gly
            515                 520                 525

Phe Thr Gly Asn Tyr Glu Glu Tyr Phe Gly Leu Ala Thr Asp Val Asp
530                 535                 540

Ala Val Val Tyr Leu Met Leu Val Asn Asp Leu Ile His Gly Leu Phe
545                 550                 555                 560

Pro Asp Ala Ile Thr Ile Gly Glu Asp Val Ser Gly Met Pro Thr Phe
                565                 570                 575

Cys Ile Pro Val Gln Glu Gly Val Gly Phe Asp Tyr Arg Leu His
                580                 585                 590

Met Ala Ile Ala Asp Lys Arg Ile Glu Leu Leu Lys Lys Arg Asp Glu
        595                 600                 605

Asp Trp Arg Val Gly Asp Ile Val His Thr Leu Thr Asn Arg Arg Trp
        610                 615                 620

Ser Glu Lys Cys Val Ser Tyr Ala Glu Ser His Asp Gln Ala Leu Val
625                 630                 635                 640

Gly Asp Lys Thr Ile Ala Phe Trp Leu Met Asp Lys Asp Met Tyr Asp
                645                 650                 655

Phe Met Ala Leu Asp Arg Pro Ser Thr Ser Leu Ile Asp Arg Gly Ile
                660                 665                 670

Ala Leu His Lys Met Ile Arg Leu Val Thr Met Gly Leu Gly Gly Glu
            675                 680                 685

Gly Tyr Leu Asn Phe Met Gly Asn Glu Phe Gly His Pro Glu Trp Ile
690                 695                 700

Asp Phe Pro Arg Ala Glu Gln His Leu Ser Asp Gly Ser Val Ile Pro
705                 710                 715                 720

Gly Asn Gln Phe Ser Tyr Asp Lys Cys Arg Arg Phe Asp Leu Gly
                725                 730                 735

Asp Ala Glu Tyr Leu Arg Tyr Arg Gly Leu Gln Glu Phe Asp Arg Pro
            740                 745                 750

Met Gln Tyr Leu Glu Asp Lys Tyr Glu Phe Met Thr Ser Glu His Gln
            755                 760                 765

Phe Ile Ser Arg Lys Asp Glu Gly Asp Arg Met Ile Val Phe Glu Lys
770                 775                 780

Gly Asn Leu Val Phe Val Phe Asn Phe His Trp Thr Lys Ser Tyr Ser
785                 790                 795                 800

Asp Tyr Arg Ile Ala Cys Leu Lys Pro Gly Lys Tyr Lys Val Ala Leu
                805                 810                 815

Asp Ser Asp Asp Pro Leu Phe Gly Gly Phe Gly Arg Ile Asp His Asn
            820                 825                 830

Ala Glu Tyr Phe Thr Phe Glu Gly Trp Tyr Asp Asp Arg Pro Arg Ser
        835                 840                 845

Ile Met Val Tyr Ala Pro Cys Lys Thr Ala Val Val Tyr Ala Leu Val
        850                 855                 860

Asp Lys Glu Glu Glu Glu Glu Glu Glu Glu Glu Val Ala Ala
865                 870                 875                 880
```

-continued

Val Glu Glu Val Val Val Glu Glu Glu
            885

<210> SEQ ID NO 16
<211> LENGTH: 2576
<212> TYPE: DNA
<213> ORGANISM: Solanum tuberosum

<400> SEQUENCE: 16

```
tcattaaaga ggagaaatta actatgagag gatctcacca tcaccatcac catgggatct      60
tggctgaaaa gtcttcttac aattccgaat tccgaccttc tacagttgca gcatcgggga     120
aagtccttgt gcctggaacc cagagtgata gctcctcatc ctcaacaaac caatttgagt     180
tcactgagac atctccagaa aattccccag catcaactga tgtagatagt tcaacaatgg     240
aacacgctag ccagattaaa actgagaacg atgacgttga gccgtcaagt gatcttacag     300
gaagtgttga agagctggat tttgcttcat cactacaact acaagaaggt ggtaaactgg     360
aggagtctaa acattaaat acttctgaag agacaattat tgatgaatct gataggatca     420
gagagagggg catccctcca cctggacttg gtcagaagat ttatgaaata dacccccttt     480
tgacaaacta tcgtcaacac cttgattaca gtattcaca gtacaagaaa ctgagggagg     540
caattgacaa gtatgagggt ggtttggaag ctttttctcg tggttatgaa aaatgggtt     600
tcactcgtag tgctacaggt atcacttacc gtgagtgggc tcctggtgcc cagtcagctg     660
ccctcattgg agatttcaac aattgggacg caaatgctga cattatgact cggaatgaat     720
ttggtgtctg ggagattttt ctgccaaata atgtggatgt ttctcctgca attcctcatg     780
ggtccagagt gaagatacgt atggacactc catcaggtgt taaggattcc attcctgctt     840
ggatcaacta ctctacagct tcctgatgaa attccatata atggaatata ttatgatcca     900
cccgaagagg agaggtatat cttccaacac ccacggccaa agaaaccaaa gtcgctgaga     960
atatatgaat ctcatattgg aatgagtagt ccggagccta aaattaactc atacgtgaat    1020
tttagagatg aagttcttcc tcgcataaaa aagcttgggt acaatgcgct gcaaattatg    1080
gctattcaag agcattctta ttatgctagt tttggttatc atgtcacaaa ttttttttgca    1140
ccaagcagcc gttttggaac gcccgacgac cttaagtctt tgattgataa agctcatgag    1200
ctaggaattg ttgttctcat ggacattgtt cacagccatg catcaaataa tactttagat    1260
ggactgaaca tgtttgacgg caccgatagt tgttactttc actctggagc tcgtggttat    1320
cattggatgt gggattcccg ccttttaac tatggaaact gggaggtact taggtatctt    1380
ctctcaaatg cgagatggtg gttggatgag ttcaaatttg atggatttag atttgatggt    1440
gtgacatcaa tgatgtatac tcaccacgga ttatcggtgg gattcactgg gaactacgag    1500
gaatactttg gactcgcaac tgatgtggat gctgttgtgt atctgatgct ggtcaacgat    1560
cttattcatg gcttttccc agatgcaatt accattggtg aagatgttag cggaatgccg    1620
acattttgta ttcccgttca agatgggggt gttggctttg actatcggct gcatatggca    1680
attgctgata aatggattga gttgctcaag aaacgggatg aggattggag agtgggtgat    1740
attgttcata cactgacaaa tagaagatgg tcggaaaagt gtgtttcata cgctgaaagt    1800
catgatcaag ctctagtcgg tgataaaact atagcattct ggctgatgga caaggatatg    1860
tatgatttta tggctctgga tagaccgcca acatcattaa tagatcgtgg gatagcattg    1920
cacaagatga ttaggcttgt aactatggga ttaggaggag aagggtacct aaatttcatg    1980
ggaaatgaat tcggccaccc tgagtggatt gatttcccta gggctgaaca acacctctct    2040
```

```
gatgactcag taattcccgg aaaccaattc agttatgata aatgcagacg gagatttgac    2100
ctgggagatg cagaatattt aagataccgt gggttgcaag aatttgaccg ggctatgcag    2160
tatcttgaag ataaatatga gtttatgact tcagaacacc agttcatatc acgaaaggat    2220
gaaggagata ggatgattgt atttgaaaaa ggaaacctag ttttttgtctt taattttcac    2280 tggacaaaaa gctattcaga ctatcgcata ggctgcctga agcctggaaa atacaaggtt    2340
gccttggact cagatgatcc acttttttggt ggcttcggga gaattgatca taatgccgaa    2400
tatttcacct ttgaaggatg gtatgatgat cgtcctcgtt caattatggt gtatgcacct    2460
tgtagaacag cagtggtcta tgcactagta gacaaagaag aagaagaaga agaagaagaa    2520
gaagaagtag cagtagtaga agaagtagta gtagaagaag aatgaacgaa cttgtg        2576
```

```
<210> SEQ ID NO 17
<211> LENGTH: 2529
<212> TYPE: DNA
<213> ORGANISM: Solanum tuberosum
<220> FEATURE:
<221> NAME/KEY: modified_base
<222> LOCATION: (2492)..(2492)
<223> OTHER INFORMATION: a, c, g, t, other or unknown
<220> FEATURE:
<221> NAME/KEY: modified_base
<222> LOCATION: (2499)..(2499)
<223> OTHER INFORMATION: a, c, g, t, other or unknown
<220> FEATURE:
<221> NAME/KEY: modified_base
<222> LOCATION: (2516)..(2516)
<223> OTHER INFORMATION: a, c, g, t, other or unknown
<220> FEATURE:
<221> NAME/KEY: modified_base
<222> LOCATION: (2520)..(2521)
<223> OTHER INFORMATION: a, c, g, t, other or unknown

<400> SEQUENCE: 17
```

```
ggatgctaat gtttctgtat tcttgaaaaa gcactctctt tcacggaaga tcttggctga     60
aaagtcttct tacaattccg aatcccgacc ttctacagtt gcagcatcgg ggaaagtcct    120
tgtgcctgga ayccagagtg atagctcctc atcctcaaca gaccaatttg agttcactga    180
gacatctcca gaaaattccc cagcatcaac tgatgtagat agttcaacaa tggaacacgc    240
tagccagatt aaaactgaga acgatgacgt tgagccgtca agtgatctta caggaagtgt    300
tgaagagctg gattttgctt catcactaca actacaagaa ggtggtaaac tggaggagtc    360
taaaacatta aatacttctg aagagacaat tattgatgaa tctgatagga tcagagagag    420
gggcatccct ccacctggac ttggtcagaa gatttatgaa atagaccccc ttttgacaaa    480
ctatcgtcaa caccttgatt acaggtattc acagtacaag aaactgaggg aggcaattga    540
caagtatgag ggtggtttgg aagcttttttc tcgtggttat gaaaaaatgg gtttcactcg    600
tagtgctaca ggtatcactt accgtgagtg ggctcctggt gcccagtcag ctgccctcat    660
tggagatttc aacaattggg acgcaaatgc tgacattatg actcggaatg aatttggtgt    720
ctgggagatt tttctgccaa ataatgtgga tggttctcct gcaattcctc atgggtccag    780
agtgaagata cgyatggaca ctccatcagg tgttaaggat tccattcctg cttggatcaa    840
ctactcttta cagcttcctg atgaaattcc atataatgga atatattatg atccacccga    900
agaggagagg tatrtcttcc aacacccacg gccaaagaaa ccaaagtcgc tgagaatata    960
tgaatctcat attggaatga gtagtccgga gcctaaaatt aactcatacg tgaattttag   1020
agatgaagtt cttcctcgca taaaaaasct tgggtacaat gcggtgcaaa ttatggctat   1080
tcaagagcat tcttattatg ctagttttgg ttatcatgtc acaaatttttt ttgcaccaag   1140
```

```
cagccgtttt ggaacgcccg acgaccttaa gtctttgatt gataaagctc atgagctagg    1200
aattgttgtt ctcatggaca ttgttcacag ccatgcatca ataatactt tagatggact    1260 gaacatgttt gacggcacag atagttgtta ctttcactct ggagctcgtg gttatcattg    1320
gatgtgggat tcccgcctct ttaactatgg aaactgggag gtacttaggt atcttctctc    1380
aaatgcgaga tggtggttgg atgagttcaa atttgatgga tttagatttg atggtgtgac    1440
atcaatgatg tatactcacc acggattatc ggtgggattc actgggaact acgaggaata    1500
ctttggactc gcaactgatg tggatgctgt tgtgtatctg atgctggtca acgatcttat    1560
tcacgggctt ttcccagatg caattaccat tggtgaagat gttagcggaa tgccgacatt    1620
ttgtattccc gttcaagatg ggggtgttgg cttttgactat cggctgcata tggcaattgc    1680
tgataaatgg attgagttgc tcaagaaacg ggatgaggat tggagagtgg gtgatattgt    1740
tcatacactg acaaatagaa gatggtcgga aaagtgtgtt tcatmcgctg aaagtcatga    1800
tcaagctcta gtcggtgata aaactatagc atyctggctg atggacaagg atatgtatga    1860
ttttatggct ctggatagac cgycaacayc attaatagat cgtgggatag cattgcacaa    1920
gatgattagg cttgtaacta tgggattagg aggagaaggg tacctaaatt tcatgggaaa    1980
tgaattcggc caccctgagt ggattgattt ccctagggct garcaacacc tctctgatgg    2040
ctcagtaatt cccggaaacc aattcagtta tgataaatgc agacggagat ttgacctggg    2100
agatgcagaa tatttaagat accatgggtt gcaagaattt gaccgggcta tgcagtatct    2160
tgaagataaa tatgagttta tgacttcaga acaccagttc atatcacgaa aggatgaagg    2220
agataggatg attgtatttg aaaraggaaa cctagttttt gtctttaatt ttccactggac    2280 aaatagctat tcagactatc gcataggctg cctgaagcct ggaaaataca aggttggctt    2340
ggactcagat gatccacttt ttggtggctt cgggagaatt gatcataatg ccgaatattt    2400
cacctctgaa ggatcgtatg atgatcgtcc tcgttcaatt atggtgtatg cacctagtag    2460
aacagcagtg gtctatgcac tagtagacaa antagaagna gaagaagaag aagaanccgn    2520 ngaagaatt                                                            2529
```

<210> SEQ ID NO 18
<211> LENGTH: 3187
<212> TYPE: DNA
<213> ORGANISM: Solanum tuberosum
<220> FEATURE:
<221> NAME/KEY: modified_base
<222> LOCATION: (3071)..(3071)
<223> OTHER INFORMATION: a, c, g, t, other or unknown
<220> FEATURE:
<221> NAME/KEY: modified_base
<222> LOCATION: (3159)..(3159)
<223> OTHER INFORMATION: a, c, g, t, other or unknown
<220> FEATURE:
<221> NAME/KEY: modified_base
<222> LOCATION: (3162)..(3165)
<223> OTHER INFORMATION: a, c, g, t, other or unknown

<400> SEQUENCE: 18

```
aaaaacctcc tccactcagt cttgggatct ctctctctct tcacgcttct cttggggcct      60
tgaactcagc aatttgacac tcagttagtt acactgccat cactcatcag atctctattt     120
tttctcttaa ttccaaccaa ggaatgaatt aaaagattag atttgaagga gagaagaaga     180
aagatggtgt atacactctc tggagttcgt tttcctactg ttccatcagt gtacaaatct     240
aatggattca gcagtaatgg tgatcggagg aatgctaatg tttctgtatt cttgaaaaag     300
```

-continued

```
cactctcttt cacggaagat cttggctgaa aagtcttctt acgattccga atcccgacct    360
tctacagttg cagcatcggg gaaagtcctt gtacctggaa tccagagtga tagctcctca    420
tcctcaacag accaatttga gttcactgag acagctccag aaaattcccc agcatcaact    480
gatgtggata gttcaacaat ggaacacgct agccagatta aaactgagaa cgatgacgtt    540
gagccgtcaa gtgatcttac aggaagtgtt gaagagttgg attttgcttc atcactacaa    600
ctacaagaag gtggtaaact ggaggagtct aaaacattaa atacttctga agagacaatt    660
attgatgaat ctgataggat cagagagagg ggcatccctc cacctggact tggtcagaag    720
atttatgaaa tagacccct tttgacaaac tatcgtcaac accttgatta caggtattca    780
cagtacaaga aaatgaggga ggcaattgac aagtatgagg gtggtttgga agcttttttct   840 cgtggttatg aaaaaatggg tttcactcgt agtgctacag gtatcactta ccgtgagtgg    900
gctcctggtg cccagtcagc tgctctcatt ggagatttca acaattggga cgcaaatgct    960
gacattatga ctcggaatga atttggtgtc tgggagattt ttctgccaaa taatgtggat   1020
ggttctcctg caattcctca tgggtccaga gtgaagatac gcatggacac ttcatcaggt   1080
gttaaggatt ccattcctgc ttggatcaac tactctttac agcttcctga tgaaattcca   1140
tataatggaa tatattatga tccacccgaa gaggagaggt atgtcttcca cacccacgg    1200 ccaaagaaac caaagtcgct gagaatatat gaatctcata ttggaatgag tagtccggag   1260
cctaaaatta actcatacgt gaattttaga gatgaagttc ttcctcgcat aaaaaacctt   1320
gggtacaatg cggtgcaaat tatggctatt caagagcatt cttattatgc tagttttggt   1380
tatcatgtca caatttttt tgcaccaagc agccgttttg gaacgcccga cgaccttaag    1440
tctttgattg ataaagctca tgagctagga attgttgttc tcatggacat tgttcacagc   1500
catgcatcaa ataatacttt agatggactg aacatgtttg acggcacaga tagttgttac   1560
tttcactctg gagctcgtgg ttatcattgg atgtgggatt cccgcctctt taactatgga   1620
aactgggagg tacttaggta tcttctctca aatgcgagat ggtggttgga tgagtgcaaa   1680
tttgrtggat ttagattcga tggtgtgaca tcaatgatgt atactcacca cggattatcg   1740
gtgggattca ctgggaacta cgaggaatac tttggactcg caactgatgt rgatgctgcc   1800
gtgtatctga tgctggccaa cgatcttatt catgggcttt tcccagatgc aattaccatt   1860
ggtgaagatg ttagcggaat gccgacattt tgtattcccg ttcaagatgg gggtgttggc   1920
tttgactatc ggctgcatat ggcaattgct gataaatgga ttgagttgct caagaaacgg   1980
gatgaggatt ggagagtggg tgatattgtt catacactga caaatagaag atggtcggaa   2040
aagtgtgttt catacgctga aagtcatgat caagctctag tcggtgataa aactatagca   2100
ttctggctga tggacaagga tatgtatgat tttatggctt tggatagacc gtcaacatca   2160
ttaatagatc gtgggatagc attgcacaag atgattaggc ttgtaactat gggattagga   2220
ggagaagggt acctaaattt catgggaaat gaattcggcc accctgagtg gattgatttc   2280
cctagggctg aacaacacct ctctgatggc tcagtaattc ccggaaacca attcagttat   2340
gataaatgca gacggagatt tgacctggga gatgcagaat attaagata ccgtgggttg    2400 caagaatttg accgggctat gcagtatctt gaagataaat atgagtttat gacttcagaa   2460
caccagttca tatcacgaaa ggatgaagga gataggatga ttgtatttga aaaggaaac    2520 ctagttttg tctttaattt tcactggaca aaaagctatt cagactatcg cataggctgg    2580
ctgaagcctg gaaaatacaa ggttgccttg gactcagatg atccacttt tggtggcttc    2640 gggagaattg atcataatgc cgaatgtttc acctttgaag gatggtatga tgatcgtcct   2700
```

-continued

```
cgttcaatta tggtgtatgc acctagtaga acagcagtgg tctatgcact agtagacaaa    2760
gaagaagaag aagaagaagt agcagtagta gaagaagtag tagtagaaga agaatgaacg    2820
aacttgtgat cgcgttgaaa gatttgaacg ctacatagag cttcttgacg tatctggcaa    2880
tattgcatca gtcttggcgg aatttcatgt gacaaaaggt ttgcaattct ttccactatt    2940
agtagtgcaa cgatatacgc agagatgaag tgctgaacaa acatatgtaa atcgatgaa     3000 tttatgtcga atgctgggac gggcttcagc aggttttgct tagtgagttc tgtaaattgt    3060
catctcttta natgtacagc ccactagaaa tcaattatgt gagacctaaa aaacaataac    3120
cataaaatgg aaatagtgct gatctaatga tgttttaanc cnnnnaaaaa aaaaaaaaaa    3180
actcgag                                                              3187
```

<210> SEQ ID NO 19
<211> LENGTH: 2578
<212> TYPE: DNA
<213> ORGANISM: Solanum tuberosum
<220> FEATURE:
<221> NAME/KEY: CDS
<222> LOCATION: (24)..(2564)

<400> SEQUENCE: 19

```
tcattaaaga ggagaaatta act atg aga gga tct cac cat cac cat cac cat        53
                        Met Arg Gly Ser His His His His His His
                         1               5                  10 ggg atc ttg gct gaa aag tct tct tac aat tcc gaa ttc cga cct tct         101
Gly Ile Leu Ala Glu Lys Ser Ser Tyr Asn Ser Glu Phe Arg Pro Ser
             15                  20                  25 aca gtt gca gca tcg ggg aaa gtc ctt gtg cct gga acc cag agt gat         149
Thr Val Ala Ala Ser Gly Lys Val Leu Val Pro Gly Thr Gln Ser Asp
         30                  35                  40 agc tcc tca tcc tca aca aac caa ttt gag ttc act gag aca tct cca         197
Ser Ser Ser Ser Ser Thr Asn Gln Phe Glu Phe Thr Glu Thr Ser Pro
     45                  50                  55 gaa aat tcc cca gca tca act gat gta gat agt tca aca atg gaa cac         245
Glu Asn Ser Pro Ala Ser Thr Asp Val Asp Ser Ser Thr Met Glu His
 60                  65                  70 gct agc cag att aaa act gag aac gat gac gtt gag ccg tca agt gat         293
Ala Ser Gln Ile Lys Thr Glu Asn Asp Asp Val Glu Pro Ser Ser Asp
 75                  80                  85                  90 ctt aca gga agt gtt gaa gag ctg gat ttt gct tca tca cta caa cta         341
Leu Thr Gly Ser Val Glu Glu Leu Asp Phe Ala Ser Ser Leu Gln Leu
                 95                 100                 105 caa gaa ggt ggt aaa ctg gag gag tct aaa aca tta aat act tct gaa         389
Gln Glu Gly Gly Lys Leu Glu Glu Ser Lys Thr Leu Asn Thr Ser Glu
            110                 115                 120 gag aca att att gat gaa tct gat agg atc aga gag agg ggc atc cct         437
Glu Thr Ile Ile Asp Glu Ser Asp Arg Ile Arg Glu Arg Gly Ile Pro
        125                 130                 135 cca cct gga ctt ggt cag aag att tat gaa ata gac ccc ttg tta aca         485
Pro Pro Gly Leu Gly Gln Lys Ile Tyr Glu Ile Asp Pro Leu Leu Thr
    140                 145                 150 aac tat cgt caa cac ctt gat tac agg tat tca cag tac aag aaa ctg         533
Asn Tyr Arg Gln His Leu Asp Tyr Arg Tyr Ser Gln Tyr Lys Lys Leu
155                 160                 165                 170 agg gag gca att gac aag tat gag ggt ggt ttg gaa gct ttt tct cgt         581
Arg Glu Ala Ile Asp Lys Tyr Glu Gly Gly Leu Glu Ala Phe Ser Arg
                175                 180                 185 ggt tat gaa aaa atg ggt ttc act cgt agt gct aca ggt atc act tac         629
```

-continued

| | | |
|---|---|---|
| Gly Tyr Glu Lys Met Gly Phe Thr Arg Ser Ala Thr Gly Ile Thr Tyr<br>                190                 195                 200 | | |
| cgt gag tgg gct cct ggt gcc cag tca gct gcc ctc att gga gat ttc<br>Arg Glu Trp Ala Pro Gly Ala Gln Ser Ala Ala Leu Ile Gly Asp Phe<br>        205                 210                 215 | | 677 |
| aac aat tgg gac gca aat gct gac att atg act cgg aat gaa ttt ggt<br>Asn Asn Trp Asp Ala Asn Ala Asp Ile Met Thr Arg Asn Glu Phe Gly<br>220                 225                 230 | | 725 |
| gtc tgg gag att ttt ctg cca aat aat gtg gat ggt tct cct gca att<br>Val Trp Glu Ile Phe Leu Pro Asn Asn Val Asp Gly Ser Pro Ala Ile<br>235                 240                 245                 250 | | 773 |
| cct cat ggg tcc aga gtg aag ata cgt atg gac act cca tca ggt gtt<br>Pro His Gly Ser Arg Val Lys Ile Arg Met Asp Thr Pro Ser Gly Val<br>                255                 260                 265 | | 821 |
| aag gat tcc att cct gct tgg atc aac tac tct tca cag ctt cct gat<br>Lys Asp Ser Ile Pro Ala Trp Ile Asn Tyr Ser Ser Gln Leu Pro Asp<br>        270                 275                 280 | | 869 |
| gaa att cca tat aat gga ata tat tat gat cca ccc gaa gag gag agg<br>Glu Ile Pro Tyr Asn Gly Ile Tyr Tyr Asp Pro Pro Glu Glu Glu Arg<br>285                 290                 295 | | 917 |
| tat atc ttc caa cac cca cgg cca aag aaa cca aag tcg ctg aga ata<br>Tyr Ile Phe Gln His Pro Arg Pro Lys Lys Pro Lys Ser Leu Arg Ile<br>300                 305                 310 | | 965 |
| tat gaa tct cat att gga atg agt agt ccg gag cct aaa att aac tca<br>Tyr Glu Ser His Ile Gly Met Ser Ser Pro Glu Pro Lys Ile Asn Ser<br>315                 320                 325                 330 | | 1013 |
| tac gtg aat ttt aga gat gaa gtt ctt cct cgc ata aaa aag ctt ggg<br>Tyr Val Asn Phe Arg Asp Glu Val Leu Pro Arg Ile Lys Lys Leu Gly<br>                335                 340                 345 | | 1061 |
| tac aat gcg gtg caa att atg gct att caa gag cat tct tat tat gct<br>Tyr Asn Ala Val Gln Ile Met Ala Ile Gln Glu His Ser Tyr Tyr Ala<br>        350                 355                 360 | | 1109 |
| agt ttt ggt tat cat gtc aca aat ttt ttt gca cca agc agc cgt ttt<br>Ser Phe Gly Tyr His Val Thr Asn Phe Phe Ala Pro Ser Ser Arg Phe<br>365                 370                 375 | | 1157 |
| gga acg ccc gac gac ctt aag tct ttg att gat aaa gct cat gag cta<br>Gly Thr Pro Asp Asp Leu Lys Ser Leu Ile Asp Lys Ala His Glu Leu<br>        380                 385                 390 | | 1205 |
| gga att gtt gtt ctc atg gac att gtt cac agc cat gca tca aat aat<br>Gly Ile Val Val Leu Met Asp Ile Val His Ser His Ala Ser Asn Asn<br>395                 400                 405                 410 | | 1253 |
| act tta gat gga ctg aac atg ttt gac ggc acc gat agt tgt tac ttt<br>Thr Leu Asp Gly Leu Asn Met Phe Asp Gly Thr Asp Ser Cys Tyr Phe<br>                415                 420                 425 | | 1301 |
| cac tct gga gct cgt ggt tat cat tgg atg tgg gat tcc cgc ctt ttt<br>His Ser Gly Ala Arg Gly Tyr His Trp Met Trp Asp Ser Arg Leu Phe<br>        430                 435                 440 | | 1349 |
| aac tat gga aac tgg gag gta ctt agg tat ctt ctc tca aat gcg aga<br>Asn Tyr Gly Asn Trp Glu Val Leu Arg Tyr Leu Leu Ser Asn Ala Arg<br>        445                 450                 455 | | 1397 |
| tgg tgg ttg gat gag ttc aaa ttt gat gga ttt aga ttt gat ggt gtg<br>Trp Trp Leu Asp Glu Phe Lys Phe Asp Gly Phe Arg Phe Asp Gly Val<br>        460                 465                 470 | | 1445 |
| aca tca atg atg tat act cac cac gga tta tcg gtg gga ttc act ggg<br>Thr Ser Met Met Tyr Thr His His Gly Leu Ser Val Gly Phe Thr Gly<br>475                 480                 485                 490 | | 1493 |
| aac tac gag gaa tac ttt gga ctc gca act gat gtg gat gct gtt gtg<br>Asn Tyr Glu Glu Tyr Phe Gly Leu Ala Thr Asp Val Asp Ala Val Val<br>                495                 500                 505 | | 1541 |

```
tat ctg atg ctg gtc aac gat ctt att cat ggg ctt ttc cca gat gca     1589
Tyr Leu Met Leu Val Asn Asp Leu Ile His Gly Leu Phe Pro Asp Ala
            510                 515                 520 att acc att ggt gaa gat gtt agc gga atg ccg aca ttt tgt att ccc     1637
Ile Thr Ile Gly Glu Asp Val Ser Gly Met Pro Thr Phe Cys Ile Pro
525                 530                 535 gtt caa gat ggg ggt gtt ggc ttt gac tat cgg ctg cat atg gca att     1685
Val Gln Asp Gly Gly Val Gly Phe Asp Tyr Arg Leu His Met Ala Ile
            540                 545                 550 gct gat aaa tgg att gag ttg ctc aag aaa cgg gat gag gat tgg aga     1733
Ala Asp Lys Trp Ile Glu Leu Leu Lys Lys Arg Asp Glu Asp Trp Arg
555                 560                 565                 570 gtg ggt gat att gtt cat aca ctg aca aat aga aga tgg tcg gaa aag     1781
Val Gly Asp Ile Val His Thr Leu Thr Asn Arg Arg Trp Ser Glu Lys
            575                 580                 585 tgt gtt tca tac gct gaa agt cat gat caa gct cta gtc ggt gat aaa     1829
Cys Val Ser Tyr Ala Glu Ser His Asp Gln Ala Leu Val Gly Asp Lys
            590                 595                 600 act ata gca ttc tgg ctg atg gac aag gat atg tat gat ttt atg gct     1877
Thr Ile Ala Phe Trp Leu Met Asp Lys Asp Met Tyr Asp Phe Met Ala
            605                 610                 615 ctg gat aga ccg cca aca tca tta ata gat cgt ggg ata gca ttg cac     1925
Leu Asp Arg Pro Pro Thr Ser Leu Ile Asp Arg Gly Ile Ala Leu His
620                 625                 630 aag atg att agg ctt gta act atg gga tta gga gga gaa ggg tac cta     1973
Lys Met Ile Arg Leu Val Thr Met Gly Leu Gly Gly Glu Gly Tyr Leu
635                 640                 645                 650 aat ttc atg gga aat gaa ttc ggc cac cct gag tgg att gat ttc cct     2021
Asn Phe Met Gly Asn Glu Phe Gly His Pro Glu Trp Ile Asp Phe Pro
            655                 660                 665 agg gct gaa caa cac ctc tct gat gac tca gta att ccc gga aac caa     2069
Arg Ala Glu Gln His Leu Ser Asp Asp Ser Val Ile Pro Gly Asn Gln
            670                 675                 680 ttc agt tat gat aaa tgc aga cgg aga ttt gac ctg gga gat gca gaa     2117
Phe Ser Tyr Asp Lys Cys Arg Arg Arg Phe Asp Leu Gly Asp Ala Glu
            685                 690                 695 tat tta aga tac cgt ggg ttg caa gaa ttt gac cgg gct atg cag tat     2165
Tyr Leu Arg Tyr Arg Gly Leu Gln Glu Phe Asp Arg Ala Met Gln Tyr
700                 705                 710 ctt gaa gat aaa tat gag ttt atg act tca gaa cac cag ttc ata tca     2213
Leu Glu Asp Lys Tyr Glu Phe Met Thr Ser Glu His Gln Phe Ile Ser
715                 720                 725                 730 cga aag gat gaa gga gat agg atg att gta ttt gaa aaa gga aac cta     2261
Arg Lys Asp Glu Gly Asp Arg Met Ile Val Phe Glu Lys Gly Asn Leu
                735                 740                 745 gtt ttt gtc ttt aat ttt cac tgg aca aaa agc tat tca gac tat cgc     2309
Val Phe Val Phe Asn Phe His Trp Thr Lys Ser Tyr Ser Asp Tyr Arg
            750                 755                 760 ata ggc tgc ctg aag cct gga aaa tac aag gtt gcc ttg gac tca gat     2357
Ile Gly Cys Leu Lys Pro Gly Lys Tyr Lys Val Ala Leu Asp Ser Asp
            765                 770                 775 gat cca ctt ttt ggt ggc ttc ggg aga att gat cat aat gcc gaa tat     2405
Asp Pro Leu Phe Gly Gly Phe Gly Arg Ile Asp His Asn Ala Glu Tyr
            780                 785                 790 ttc acc ttt gaa gga tgg tat gat gat cgt cct cgt tca att atg gtg     2453
Phe Thr Phe Glu Gly Trp Tyr Asp Asp Arg Pro Arg Ser Ile Met Val
795                 800                 805                 810 tat gca cct tgt aga aca gca gtg gtc tat gca cta gta gac aaa gaa     2501
Tyr Ala Pro Cys Arg Thr Ala Val Val Tyr Ala Leu Val Asp Lys Glu
            815                 820                 825
```

-continued

```
gaa gaa gaa gaa gaa gaa gaa gaa gta gca gta gta gaa gaa gta        2549
Glu Glu Glu Glu Glu Glu Glu Glu Val Ala Val Val Glu Glu Val
            830                 835                 840 gta gta gaa gaa gaa tgaacgaact tgtg                                2578
Val Val Glu Glu Glu
        845
```

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (12)..(12)
<223> OTHER INFORMATION: inosine

<400> SEQUENCE: 20
aatttyatgg gnaaygartt ygg                                           23

<210> SEQ ID NO 21
<211> LENGTH: 203
<212> TYPE: PRT
<213> ORGANISM: Zea mays

<400> SEQUENCE: 21

```
Pro Ser Thr Pro Thr Ile Asp Arg Gly Ile Ala Leu His Lys Met Ile
1               5                   10                  15

Arg Leu Ile Thr Met Gly Leu Gly Gly Glu Gly Tyr Leu Asn Phe Met
            20                  25                  30

Gly Asn Glu Phe Gly His Pro Glu Trp Ile Asp Phe Pro Arg Gly Pro
        35                  40                  45

Gln Arg Leu Pro Ser Gly Lys Phe Ile Pro Gly Asn Asn Asn Ser Tyr
    50                  55                  60

Asp Lys Cys Arg Arg Arg Phe Asp Leu Gly Asp Ala Asp Tyr Leu Arg
65                  70                  75                  80

Tyr His Gly Met Gln Glu Phe Asp Gln Ala Met Gln His Leu Glu Gln
                85                  90                  95

Lys Tyr Glu Phe Met Thr Ser Asp His Gln Tyr Ile Ser Arg Lys His
            100                 105                 110

Glu Glu Asp Lys Val Ile Val Phe Glu Lys Gly Asp Leu Val Phe Val
        115                 120                 125

Phe Asn Phe His Cys Asn Asn Ser Tyr Phe Asp Tyr Arg Ile Gly Cys
    130                 135                 140

Arg Lys Pro Gly Val Tyr Lys Val Val Leu Asp Ser Asp Ala Gly Leu
145                 150                 155                 160

Phe Gly Gly Phe Ser Arg Ile His His Ala Ala Glu His Phe Thr Ala
                165                 170                 175

Asp Cys Ser His Asp Asn Arg Pro Tyr Ser Phe Ser Val Tyr Thr Pro
            180                 185                 190

Ser Arg Thr Cys Val Val Tyr Ala Pro Val Glu
        195                 200
```

<210> SEQ ID NO 22
<211> LENGTH: 213
<212> TYPE: PRT
<213> ORGANISM: Lathyrus sp.

```
<400> SEQUENCE: 22

Pro Ser Thr Pro Leu Ile Asp Arg Gly Ile Ala Leu His Lys Met Ile
1               5                   10                  15

Arg Leu Ile Thr Met Gly Leu Gly Glu Gly Tyr Leu Asn Phe Met
            20                  25                  30

Gly Asn Glu Phe Gly His Pro Glu Trp Ile Asp Phe Pro Arg Gly Glu
            35                  40                  45

Gln His Leu Pro Asn Gly Lys Ile Val Pro Gly Asn Asn Asn Ser Tyr
        50                  55                  60

Asp Lys Cys Arg Arg Phe Asp Leu Gly Asp Ala Asp Tyr Leu Arg
65                  70                  75                  80

Tyr His Gly Met Gln Glu Phe Asp Arg Ala Met Gln His Leu Glu Glu
                85                  90                  95

Thr Tyr Gly Phe Met Thr Ser Glu His Gln Tyr Ile Ser Arg Lys Asn
                100                 105                 110

Glu Gly Asp Arg Val Ile Ile Phe Glu Arg Asp Asn Leu Val Phe Val
            115                 120                 125

Phe Asn Phe His Trp Thr Asn Ser Tyr Ser Asp Tyr Lys Val Gly Cys
130                 135                 140

Leu Lys Pro Gly Lys Tyr Lys Ile Val Leu Asp Ser Asp Thr Leu
145                 150                 155                 160

Phe Gly Gly Phe Asn Arg Leu Asn His Thr Ala Glu Tyr Phe Thr Ser
                165                 170                 175

Glu Gly Trp Tyr Asp Asp Arg Pro Arg Ser Phe Leu Val Tyr Ala Pro
            180                 185                 190

Ser Arg Thr Ala Val Val Tyr Ala Leu Ala Asp Gly Val Glu Ser Glu
            195                 200                 205

Pro Ile Glu Leu Ser
    210

<210> SEQ ID NO 23
<211> LENGTH: 258
<212> TYPE: PRT
<213> ORGANISM: Zea mays

<400> SEQUENCE: 23

Pro Ala Ser Pro Thr Ile Asp Arg Gly Ile Ala Leu Gln Lys Met Ile
1               5                   10                  15

His Phe Ile Thr Met Ala Leu Gly Gly Asp Gly Tyr Leu Asn Phe Met
            20                  25                  30

Gly Asn Glu Phe Gly His Pro Glu Trp Ile Asp Phe Pro Arg Glu Gly
            35                  40                  45

Asn Asn Trp Ser Tyr Asp Lys Cys Arg Arg Gln Trp Ser Leu Val Asp
    50                  55                  60

Thr Asp His Leu Arg Tyr Lys Tyr Met Asn Ala Phe Asp Gln Ala Met
65                  70                  75                  80

Asn Ala Leu Asp Glu Arg Phe Ser Phe Leu Ser Ser Lys Gln Ile
                85                  90                  95

Val Ser Asp Met Asn Asp Glu Glu Lys Val Ile Val Phe Glu Arg Gly
                100                 105                 110

Asp Leu Val Phe Val Phe Asn Phe His Pro Lys Lys Thr Tyr Glu Gly
            115                 120                 125

Tyr Lys Val Gly Cys Asp Leu Pro Gly Lys Tyr Arg Val Ala Leu Asp
    130                 135                 140
```

```
Ser Asp Ala Leu Val Phe Gly His Gly Arg Val Gly His Asp Val
145                 150                 155                 160

Asp His Phe Thr Ser Pro Glu Gly Val Pro Gly Val Pro Glu Thr Asn
                165                 170                 175

Phe Asn Asn Arg Pro Asn Ser Phe Lys Val Leu Ser Pro Pro Arg Thr
            180                 185                 190

Cys Val Ala Tyr Tyr Arg Val Asp Glu Ala Gly Ala Gly Arg Arg Leu
        195                 200                 205

His Ala Lys Ala Glu Thr Gly Lys Thr Ser Pro Ala Glu Ser Ile Asp
    210                 215                 220

Val Lys Ala Ser Arg Ala Ser Ser Lys Glu Asp Lys Glu Ala Thr Ala
225                 230                 235                 240

Gly Gly Lys Lys Gly Trp Lys Phe Ala Arg Gln Pro Ser Asp Gln Asp
                245                 250                 255

Thr Lys

<210> SEQ ID NO 24
<211> LENGTH: 210
<212> TYPE: PRT
<213> ORGANISM: Oryza sativa

<400> SEQUENCE: 24

Pro Ala Ser Pro Thr Ile Asn Arg Gly Ile Ala Leu Gln Lys Met Ile
1               5                   10                  15

His Phe Ile Thr Met Ala Leu Gly Gly Asp Gly Tyr Leu Asn Phe Met
            20                  25                  30

Gly Asn Glu Phe Gly His Pro Glu Trp Ile Asp Phe Pro Arg Glu Gly
        35                  40                  45

Asn Asn Trp Ser Tyr Asp Lys Cys Arg Arg Gln Trp Ser Leu Val Asp
    50                  55                  60

Thr Asp His Leu Arg Tyr Lys Tyr Met Asn Ala Phe Asp Gln Ala Met
65                  70                  75                  80

Asn Ala Leu Glu Glu Glu Phe Ser Phe Leu Ser Ser Ser Lys Gln Ile
                85                  90                  95

Val Ser Asp Met Asn Glu Lys Asp Lys Val Ile Val Phe Glu Arg Gly
            100                 105                 110

Asp Leu Val Phe Val Phe Asn Phe His Pro Asn Lys Thr Tyr Lys Gly
        115                 120                 125

Tyr Lys Val Gly Cys Asp Leu Pro Gly Lys Tyr Arg Val Ala Leu Asp
    130                 135                 140

Ser Asp Ala Leu Val Phe Gly His Gly Arg Val Gly His Asp Val
145                 150                 155                 160

Asp His Phe Thr Ser Pro Glu Gly Met Pro Gly Val Pro Glu Thr Asn
                165                 170                 175

Phe Asn Asn Arg Pro Asn Ser Phe Lys Val Leu Ser Pro Pro Arg Thr
            180                 185                 190

Cys Val Ala Tyr Tyr Arg Val Asp Glu Asp Arg Glu Glu Leu Arg Arg
        195                 200                 205

Gly Gly
210

<210> SEQ ID NO 25
<211> LENGTH: 210
<212> TYPE: PRT
<213> ORGANISM: Solanum tuberosum
```

```
<400> SEQUENCE: 25

Asp Ala Ser Pro Val Val Asp Ala Gly Ile Ala Leu Asp Lys Met Ile
1               5                   10                  15

His Phe Phe Thr Met Ala Leu Gly Gly Glu Gly Tyr Leu Asn Phe Met
                20                  25                  30

Gly Asn Glu Phe Gly His Pro Glu Trp Ile Asp Phe Pro Ser Glu Gly
            35                  40                  45

Asn Asn Trp Ser Tyr Asp Lys Cys Arg Arg Gln Trp Asn Leu Ala Asp
    50                  55                  60

Ser Glu His Leu Arg Tyr Lys Phe Met Asn Ala Phe Asp Arg Ala Met
65                  70                  75                  80

Asn Ser Leu Asp Glu Lys Phe Ser Phe Leu Ala Ser Gly Lys Gln Ile
                85                  90                  95

Val Ser Ser Met Asp Asp Asn Lys Val Val Phe Glu Arg Gly
                100                 105                 110

Asp Leu Val Phe Val Phe Asn Phe His Pro Asn Asn Thr Tyr Glu Gly
                115                 120                 125

Tyr Lys Val Gly Cys Asp Leu Pro Gly Lys Tyr Arg Val Ala Leu Asp
    130                 135                 140

Ser Asp Ala Trp Glu Phe Gly Gly His Gly Arg Ala Gly His Asp Val
145                 150                 155                 160

Asp His Phe Thr Ser Pro Glu Gly Ile Pro Gly Val Pro Glu Thr Asn
                165                 170                 175

Phe Asn Gly Arg Pro Asn Ser Phe Lys Val Leu Ser Pro Ala Arg Thr
            180                 185                 190

Cys Val Ala Tyr Tyr Arg Val Asp Glu Arg Met Ser Glu Thr Glu Asp
        195                 200                 205

Tyr Gln
    210

<210> SEQ ID NO 26
<211> LENGTH: 195
<212> TYPE: PRT
<213> ORGANISM: Homo sapiens

<400> SEQUENCE: 26

Pro Phe Thr Pro Val Ile Asp Arg Gly Ile Gln Leu His Lys Met Ile
1               5                   10                  15

Arg Leu Ile Thr His Gly Leu Gly Gly Glu Gly Tyr Leu Asn Phe Met
                20                  25                  30

Gly Asn Glu Phe Gly His Pro Glu Trp Leu Asp Phe Pro Arg Lys Gly
            35                  40                  45

Asn Asn Glu Ser Tyr His Tyr Ala Arg Arg Gln Phe His Leu Thr Asp
    50                  55                  60

Asp Asp Leu Leu Arg Tyr Lys Phe Leu Asn Asn Phe Arg Asp Met
65                  70                  75                  80

Asn Arg Leu Glu Glu Arg Tyr Gly Trp Leu Ala Ala Pro Gln Ala Tyr
                85                  90                  95

Val Ser Glu Lys His Glu Gly Asn Lys Ile Ile Ala Phe Glu Arg Ala
                100                 105                 110

Gly Leu Leu Phe Ile Phe Asn Phe His Pro Ser Lys Ser Tyr Thr Asp
            115                 120                 125

Tyr Arg Val Gly Thr Ala Leu Pro Gly Lys Phe Lys Ile Val Leu Asp
    130                 135                 140
```

```
Ser Asp Ala Ala Glu Tyr Gly Gly His Gln Arg Leu Asp His Ser Thr
145                 150                 155                 160

Asp Phe Phe Ser Glu Ala Phe Glu His Asn Gly Arg Pro Tyr Ser Leu
                165                 170                 175

Leu Val Tyr Ile Pro Ser Arg Val Ala Leu Ile Leu Gln Asn Val Asp
            180                 185                 190

Leu Pro Asn
        195
```

<210> SEQ ID NO 27
<211> LENGTH: 60
<212> TYPE: DNA
<213> ORGANISM: Homo sapiens

<400> SEQUENCE: 27
ggctatctca atttcatggg taatgaattt gggcatcctg aatggttaga cttcccaaga      60

<210> SEQ ID NO 28
<211> LENGTH: 60
<212> TYPE: DNA
<213> ORGANISM: Lathyrus sp.

<400> SEQUENCE: 28
gggtatttga attttatggg gaatgaattc ggacatcctg agtggatcga ttttccaagg      60

<210> SEQ ID NO 29
<211> LENGTH: 60
<212> TYPE: DNA
<213> ORGANISM: Solanum tuberosum

<400> SEQUENCE: 29
gggtacctca atttcatggg taacgagttt ggccatcctg agtggattga cttccctagt      60

<210> SEQ ID NO 30
<211> LENGTH: 60
<212> TYPE: DNA
<213> ORGANISM: Zea mays

<400> SEQUENCE: 30
ggctacttga attttatggg aaatgagttt ggtcacccag aatggattga ctttccaaga      60

<210> SEQ ID NO 31
<211> LENGTH: 60
<212> TYPE: DNA
<213> ORGANISM: Zea mays

<400> SEQUENCE: 31
ggctatctta atttcatggg aaatgagttt ggacatcctg aatggataga ttttccaaga      60

<210> SEQ ID NO 32
<211> LENGTH: 60
<212> TYPE: DNA
<213> ORGANISM: Oryza sativa

<400> SEQUENCE: 32
ggctacttaa attttatggg caatgagttt ggccatccag aatggattga ctttccaaga      60

<210> SEQ ID NO 33
<211> LENGTH: 692
<212> TYPE: PRT
<213> ORGANISM: Solanum tuberosum

<400> SEQUENCE: 33

```
Ile Tyr Glu Ile Asp Pro Leu Leu Thr Asn Tyr Arg Gln His Leu Asp
1               5                   10                  15

Tyr Arg Tyr Ser Gln Tyr Lys Lys Leu Arg Glu Ala Ile Asp Lys Tyr
            20                  25                  30

Glu Gly Gly Leu Glu Ala Phe Ser Arg Gly Tyr Glu Lys Met Gly Phe
            35                  40                  45

Thr Arg Ser Ala Thr Gly Ile Thr Tyr Arg Glu Trp Ala Leu Gly Ala
    50                  55                  60

Gln Ser Ala Ala Leu Ile Gly Asp Phe Asn Asn Trp Asp Ala Asn Ala
65                  70                  75                  80

Asp Ile Met Thr Arg Asn Glu Phe Gly Val Trp Glu Ile Phe Leu Pro
                85                  90                  95

Asn Asn Val Asp Gly Ser Pro Ala Ile Pro His Gly Ser Arg Val Lys
            100                 105                 110

Ile Arg Met Asp Thr Pro Ser Gly Val Lys Asp Ser Ile Pro Ala Trp
        115                 120                 125

Ile Asn Tyr Ser Leu Gln Leu Pro Asp Glu Ile Pro Tyr Asn Gly Ile
130                 135                 140

His Tyr Asp Pro Pro Glu Glu Glu Arg Tyr Ile Phe Gln His Pro Arg
145                 150                 155                 160

Pro Lys Lys Pro Lys Ser Leu Arg Ile Tyr Glu Ser His Ile Gly Met
                165                 170                 175

Ser Ser Pro Glu Pro Lys Ile Asn Ser Tyr Val Asn Phe Arg Asp Glu
            180                 185                 190

Val Leu Pro Arg Ile Lys Lys Leu Gly Tyr Asn Ala Leu Gln Ile Met
        195                 200                 205

Ala Ile Gln Glu His Ser Tyr Tyr Ala Ser Phe Gly Tyr His Val Thr
210                 215                 220

Asn Phe Phe Ala Pro Ser Ser Arg Phe Gly Thr Pro Asp Asp Leu Lys
225                 230                 235                 240

Ser Leu Ile Asp Lys Ala His Glu Leu Gly Ile Val Val Leu Met Asp
                245                 250                 255

Ile Val His Ser His Ala Ser Asn Asn Thr Leu Asp Gly Leu Asn Met
            260                 265                 270

Phe Asp Cys Thr Asp Ser Cys Tyr Phe His Ser Gly Ala Arg Gly Tyr
        275                 280                 285

His Trp Met Trp Asp Ser Arg Leu Phe Asn Tyr Gly Asn Trp Glu Val
    290                 295                 300

Leu Arg Tyr Leu Leu Ser Asn Ala Arg Trp Trp Leu Asp Ala Phe Lys
305                 310                 315                 320

Phe Asp Gly Phe Arg Phe Asp Gly Val Thr Ser Met Met Tyr Ile His
                325                 330                 335

His Gly Leu Ser Val Gly Phe Thr Gly Asn Tyr Glu Glu Tyr Phe Gly
            340                 345                 350

Leu Ala Thr Asp Val Asp Ala Val Val Tyr Leu Met Leu Val Asn Asp
        355                 360                 365

Leu Ile His Gly Leu Phe Pro Asp Ala Ile Thr Ile Gly Glu Asp Val
370                 375                 380

Ser Gly Met Pro Thr Phe Cys Ile Pro Val Gln Glu Gly Gly Val Gly
385                 390                 395                 400

Phe Asp Tyr Arg Leu His Met Ala Ile Ala Asp Lys Arg Ile Glu Leu
                405                 410                 415
```

```
Leu Lys Lys Arg Asp Glu Asp Trp Arg Val Gly Asp Ile Val His Thr
                420                 425                 430
Leu Thr Asn Arg Arg Trp Ser Glu Lys Cys Val Ser Tyr Ala Glu Ser
            435                 440                 445
His Asp Gln Ala Leu Val Gly Asp Lys Thr Ile Ala Phe Trp Leu Met
        450                 455                 460
Asp Lys Asp Met Tyr Asp Phe Met Ala Leu Asp Arg Pro Ser Thr Ser
465                 470                 475                 480
Leu Ile Asp Arg Gly Ile Ala Leu His Lys Met Ile Arg Leu Val Thr
                485                 490                 495
Met Gly Leu Gly Gly Glu Gly Tyr Leu Asn Phe Met Gly Asn Glu Phe
            500                 505                 510
Gly His Pro Glu Trp Ile Asp Phe Pro Arg Ala Glu Gln His Leu Ser
        515                 520                 525
Asp Gly Ser Val Ile Pro Gly Asn Gln Phe Ser Tyr Asp Lys Cys Arg
    530                 535                 540
Arg Arg Phe Asp Leu Gly Asp Ala Glu Tyr Leu Arg Tyr Arg Gly Leu
545                 550                 555                 560
Gln Glu Phe Asp Arg Pro Met Gln Tyr Leu Glu Asp Lys Tyr Glu Phe
                565                 570                 575
Met Thr Ser Glu His Gln Phe Ile Ser Arg Lys Asp Glu Gly Asp Arg
            580                 585                 590
Met Ile Val Phe Glu Lys Gly Asn Leu Val Phe Val Phe Asn Phe His
        595                 600                 605
Trp Thr Lys Ser Tyr Ser Asp Tyr Arg Ile Ala Cys Leu Lys Pro Gly
    610                 615                 620
Lys Tyr Lys Val Ala Leu Asp Ser Asp Pro Leu Phe Gly Gly Phe
625                 630                 635                 640
Gly Arg Ile Asp His Asn Ala Glu Tyr Phe Thr Phe Glu Gly Trp Tyr
                645                 650                 655
Asp Asp Arg Pro Arg Ser Ile Met Val Tyr Ala Pro Cys Lys Thr Ala
            660                 665                 670
Val Val Tyr Ala Leu Val Asp Lys Glu Glu Glu Glu Glu Glu Glu Glu
        675                 680                 685
Glu Glu Glu Val
    690

<210> SEQ ID NO 34
<211> LENGTH: 695
<212> TYPE: PRT
<213> ORGANISM: Solanum tuberosum

<400> SEQUENCE: 34

Leu Leu Asn Leu Asp Pro Thr Leu Glu Pro Tyr Leu Asp His Phe Arg
1               5                   10                  15
His Arg Met Lys Arg Tyr Val Asp Gln Lys Met Leu Ile Glu Lys Tyr
                20                  25                  30
Glu Gly Pro Leu Glu Glu Phe Ala Gln Gly Tyr Leu Lys Phe Gly Phe
            35                  40                  45
Asn Arg Glu Asp Gly Cys Ile Val Tyr Arg Glu Trp Ala Pro Ala Ala
        50                  55                  60
Gln Glu Ala Glu Val Ile Gly Asp Phe Asn Gly Trp Asn Gly Ser Asn
65                  70                  75                  80
His Met Met Glu Lys Asp Gln Phe Gly Val Trp Ser Ile Arg Ile Pro
                85                  90                  95
```

-continued

Asp Val Asp Ser Lys Pro Val Ile Pro His Asn Ser Arg Val Lys Phe
            100                 105                 110

Arg Phe Lys His Gly Asn Gly Val Trp Val Asp Arg Ile Pro Ala Trp
            115                 120                 125

Ile Lys Tyr Ala Thr Ala Asp Ala Thr Lys Phe Ala Ala Pro Tyr Asp
            130                 135                 140

Gly Val Tyr Trp Asp Pro Pro Ser Glu Arg Tyr His Phe Lys Tyr
145                 150                 155                 160

Pro Arg Pro Pro Lys Pro Arg Ala Pro Arg Ile Tyr Glu Ala His Val
                    165                 170                 175

Gly Met Ser Ser Glu Pro Arg Val Asn Ser Tyr Arg Glu Phe Ala
            180                 185                 190

Asp Asp Val Leu Pro Arg Ile Lys Ala Asn Asn Tyr Asn Thr Val Gln
            195                 200                 205

Leu Met Ala Ile Met Glu His Ser Tyr Tyr Gly Ser Phe Gly Tyr His
            210                 215                 220

Val Thr Asn Phe Phe Ala Val Ser Asn Arg Tyr Gly Asn Pro Glu Asp
225                 230                 235                 240

Leu Lys Tyr Leu Ile Asp Lys Ala His Ser Leu Gly Leu Gln Val Leu
            245                 250                 255

Val Asp Val Val His Ser His Ala Ser Asn Asn Val Thr Asp Gly Leu
            260                 265                 270

Asn Gly Phe Asp Ile Gly Gln Gly Ser Gln Glu Ser Tyr Phe His Ala
            275                 280                 285

Gly Glu Arg Gly Tyr His Lys Leu Trp Asp Ser Arg Leu Phe Asn Tyr
            290                 295                 300

Ala Asn Trp Glu Val Leu Arg Phe Leu Leu Ser Asn Leu Arg Trp Trp
305                 310                 315                 320

Leu Glu Glu Tyr Asn Phe Asp Gly Phe Arg Phe Asp Gly Ile Thr Ser
            325                 330                 335

Met Leu Tyr Val His His Gly Ile Asn Met Gly Phe Thr Gly Asn Tyr
            340                 345                 350

Asn Glu Tyr Phe Ser Glu Ala Thr Asp Val Asp Ala Val Val Tyr Leu
            355                 360                 365

Met Leu Ala Asn Asn Leu Ile His Lys Ile Phe Pro Asp Ala Thr Val
            370                 375                 380

Ile Ala Glu Asp Val Ser Gly Met Pro Gly Leu Ser Arg Pro Val Ser
385                 390                 395                 400

Glu Gly Gly Ile Gly Phe Asp Tyr Arg Leu Ala Met Ala Ile Pro Asp
            405                 410                 415

Lys Trp Ile Asp Tyr Leu Lys Asn Lys Asn Asp Glu Asp Trp Ser Met
            420                 425                 430

Lys Glu Val Thr Ser Ser Leu Thr Asn Arg Arg Tyr Thr Glu Lys Cys
            435                 440                 445

Ile Ala Tyr Ala Glu Ser His Asp Gln Ser Ile Val Gly Asp Lys Thr
450                 455                 460

Ile Ala Phe Leu Leu Met Asp Lys Glu Met Tyr Ser Gly Met Ser Cys
465                 470                 475                 480

Leu Thr Asp Ala Ser Pro Val Val Asp Arg Gly Ile Ala Leu His Lys
            485                 490                 495

Met Ile His Phe Phe Thr Met Ala Leu Gly Gly Glu Gly Tyr Leu Asn
            500                 505                 510

-continued

```
Phe Met Gly Asn Glu Phe Gly His Pro Glu Trp Ile Asp Phe Pro Arg
        515                 520                 525

Glu Gly Asn Asn Trp Ser Tyr Asp Lys Cys Arg Arg Gln Trp Asn Leu
            530                 535                 540

Ala Asp Ser Glu His Leu Arg Tyr Lys Phe Met Asn Ala Phe Asp Arg
545                 550                 555                 560

Ala Met Asn Ser Leu Asp Glu Lys Phe Ser Phe Leu Ala Ser Gly Lys
                565                 570                 575

Gln Ile Val Ser Ser Met Asp Asp Asn Lys Val Val Phe Glu
                580                 585                 590

Arg Gly Asp Leu Val Phe Val Phe Asn Phe His Pro Asn Asn Thr Tyr
            595                 600                 605

Glu Gly Tyr Lys Val Gly Cys Asp Leu Pro Gly Lys Tyr Arg Val Ala
        610                 615                 620

Leu Gly Ser Asp Ala Trp Glu Phe Gly Gly His Gly Arg Ala Gly His
625                 630                 635                 640

Asp Val Asp His Phe Thr Ser Pro Glu Gly Ile Pro Gly Val Pro Glu
                645                 650                 655

Thr Asn Phe Asn Gly Arg Pro Asn Ser Phe Lys Val Leu Ser Pro Ala
            660                 665                 670

Arg Thr Cys Val Ala Tyr Tyr Arg Val Asp Glu Arg Met Ser Glu Thr
        675                 680                 685

Glu Asp Tyr Gln Thr Asp Ile
690                 695

<210> SEQ ID NO 35
<211> LENGTH: 873
<212> TYPE: PRT
<213> ORGANISM: Solanum tuberosum

<400> SEQUENCE: 35

Met Val Tyr Thr Leu Ser Gly Val Arg Phe Pro Thr Val Pro Ser Val
1               5                   10                  15

Tyr Lys Ser Asn Gly Phe Ser Ser Asn Gly Asp Arg Arg Asn Ala Asn
            20                  25                  30

Val Ser Val Phe Leu Lys Lys His Ser Leu Ser Arg Lys Ile Leu Ala
        35                  40                  45

Glu Lys Ser Ser Tyr Asn Ser Glu Phe Arg Pro Ser Thr Val Ala Ala
    50                  55                  60

Ser Gly Lys Val Leu Val Pro Gly Thr Gln Ser Asp Ser Ser Ser Ser
65                  70                  75                  80

Ser Thr Asp Gln Phe Glu Phe Thr Glu Thr Ser Pro Glu Asn Ser Pro
                85                  90                  95

Ala Ser Thr Asp Val Asp Ser Ser Thr Met Glu His Ala Ser Gln Ile
            100                 105                 110

Lys Thr Glu Asn Asp Asp Val Glu Pro Ser Ser Asp Leu Thr Gly Ser
        115                 120                 125

Val Glu Glu Leu Asp Phe Ala Ser Ser Leu Gln Leu Gln Glu Gly Gly
    130                 135                 140

Lys Leu Glu Glu Ser Lys Thr Leu Asn Thr Ser Glu Glu Thr Ile Ile
145                 150                 155                 160

Asp Glu Ser Asp Arg Ile Arg Glu Arg Gly Ile Pro Pro Gly Leu
                165                 170                 175

Gly Gln Lys Ile Tyr Glu Ile Asp Pro Leu Leu Thr Asn Tyr Arg Gln
            180                 185                 190
```

-continued

```
His Leu Asp Tyr Arg Tyr Ser Gln Tyr Lys Leu Arg Glu Ala Ile
        195                 200                 205
Asp Lys Tyr Glu Gly Gly Leu Glu Ala Phe Ser Arg Gly Tyr Glu Lys
    210                 215                 220
Met Gly Phe Thr Arg Ser Ala Thr Gly Ile Thr Tyr Arg Glu Trp Ala
225                 230                 235                 240
Leu Gly Ala Gln Ser Ala Ala Leu Ile Gly Asp Phe Asn Asn Trp Asp
                245                 250                 255
Ala Asn Ala Asp Ile Met Thr Arg Asn Glu Phe Gly Val Trp Glu Ile
            260                 265                 270
Phe Leu Pro Asn Asn Val Asp Gly Ser Pro Ala Ile Pro His Gly Ser
        275                 280                 285
Arg Val Lys Ile Arg Met Asp Thr Pro Ser Gly Val Lys Asp Ser Ile
    290                 295                 300
Pro Ala Trp Ile Asn Tyr Ser Leu Gln Leu Pro Asp Glu Ile Pro Tyr
305                 310                 315                 320
Asn Gly Ile His Tyr Asp Pro Pro Glu Glu Arg Tyr Ile Phe Gln
                325                 330                 335
His Pro Arg Pro Lys Lys Pro Lys Ser Leu Arg Ile Tyr Glu Ser His
            340                 345                 350
Ile Gly Met Ser Ser Pro Glu Pro Lys Ile Asn Ser Tyr Val Asn Phe
        355                 360                 365
Arg Asp Glu Val Leu Pro Arg Ile Lys Lys Leu Gly Tyr Asn Ala Leu
    370                 375                 380
Gln Ile Met Ala Ile Gln Glu His Ser Tyr Tyr Ala Ser Phe Gly Tyr
385                 390                 395                 400
His Val Thr Asn Phe Phe Ala Pro Ser Ser Arg Phe Gly Thr Pro Asp
                405                 410                 415
Asp Leu Lys Ser Leu Ile Asp Lys Ala His Glu Leu Gly Ile Val Val
            420                 425                 430
Leu Met Asp Ile Val His Ser His Ala Ser Asn Asn Thr Leu Asp Gly
        435                 440                 445
Leu Asn Met Phe Asp Cys Thr Asp Ser Cys Tyr Phe His Ser Gly Ala
    450                 455                 460
Arg Gly Tyr His Trp Met Trp Asp Ser Arg Leu Phe Asn Tyr Gly Asn
465                 470                 475                 480
Trp Glu Val Leu Arg Tyr Leu Leu Ser Asn Ala Arg Trp Trp Leu Asp
                485                 490                 495
Ala Phe Lys Phe Asp Gly Phe Arg Phe Asp Gly Val Thr Ser Met Met
            500                 505                 510
Tyr Ile His His Gly Leu Ser Val Gly Phe Thr Gly Asn Tyr Glu Glu
        515                 520                 525
Tyr Phe Gly Leu Ala Thr Asp Val Asp Ala Val Val Tyr Leu Met Leu
    530                 535                 540
Val Asn Asp Leu Ile His Gly Leu Phe Pro Asp Ala Ile Thr Ile Gly
545                 550                 555                 560
Glu Asp Val Ser Gly Met Pro Thr Phe Cys Ile Pro Val Gln Glu Gly
                565                 570                 575
Gly Val Gly Phe Asp Tyr Arg Leu His Met Ala Ile Ala Asp Lys Arg
            580                 585                 590
Ile Glu Leu Leu Lys Lys Arg Asp Glu Asp Trp Arg Val Gly Asp Ile
        595                 600                 605
```

```
Val His Thr Leu Thr Asn Arg Arg Trp Ser Glu Lys Cys Val Ser Tyr
    610                 615                 620

Ala Glu Ser His Asp Gln Ala Leu Val Gly Asp Lys Thr Ile Ala Phe
625                 630                 635                 640

Trp Leu Met Asp Lys Asp Met Tyr Asp Phe Met Ala Leu Asp Arg Pro
                645                 650                 655

Ser Thr Ser Leu Ile Asp Arg Gly Ile Ala Leu His Lys Met Ile Arg
                660                 665                 670

Leu Val Thr Met Gly Leu Gly Gly Glu Gly Tyr Leu Asn Phe Met Gly
            675                 680                 685

Asn Glu Phe Gly His Pro Glu Trp Ile Asp Phe Pro Arg Ala Glu Gln
    690                 695                 700

His Leu Ser Asp Gly Ser Val Ile Pro Gly Asn Gln Phe Ser Tyr Asp
705                 710                 715                 720

Lys Cys Arg Arg Arg Phe Asp Leu Gly Asp Ala Glu Tyr Leu Arg Tyr
                725                 730                 735

Arg Gly Leu Gln Glu Phe Asp Arg Pro Met Gln Tyr Leu Glu Asp Lys
                740                 745                 750

Tyr Glu Phe Met Thr Ser Glu His Gln Phe Ile Ser Arg Lys Asp Glu
            755                 760                 765

Gly Asp Arg Met Ile Val Phe Glu Lys Gly Asn Leu Val Phe Val Phe
770                 775                 780

Asn Phe His Trp Thr Lys Ser Tyr Ser Asp Tyr Arg Ile Ala Cys Leu
785                 790                 795                 800

Lys Pro Gly Lys Tyr Lys Val Ala Leu Asp Ser Asp Pro Leu Phe
                805                 810                 815

Gly Gly Phe Gly Arg Ile Asp His Asn Ala Glu Tyr Phe Thr Phe Glu
            820                 825                 830

Gly Trp Tyr Asp Asp Arg Pro Arg Ser Ile Met Val Tyr Ala Pro Cys
            835                 840                 845

Lys Thr Ala Val Val Tyr Ala Leu Val Asp Lys Glu Glu Glu Glu
850                 855                 860

Glu Glu Glu Glu Glu Val Ala Ala
865                 870

<210> SEQ ID NO 36
<211> LENGTH: 861
<212> TYPE: PRT
<213> ORGANISM: Lathyrus sp.

<400> SEQUENCE: 36

Met Val Tyr Thr Ile Ser Gly Ile Arg Phe Pro Val Leu Pro Ser Leu
1               5                   10                  15

His Lys Ser Thr Leu Arg Cys Asp Arg Arg Ala Ser Ser His Ser Phe
            20                  25                  30

Phe Leu Lys Asn Asn Ser Ser Phe Ser Arg Thr Ser Leu Tyr Ala
                35                  40                  45

Lys Phe Ser Arg Asp Ser Glu Thr Lys Ser Ser Thr Ile Ala Glu Ser
50                  55                  60

Asp Lys Val Leu Ile Pro Glu Asp Gln Asp Asn Ser Val Ser Leu Ala
65                  70                  75                  80

Asp Gln Leu Glu Asn Pro Asp Ile Thr Ser Glu Asp Ala Gln Asn Leu
                85                  90                  95

Glu Asp Leu Thr Met Lys Asp Gly Asn Lys Tyr Asn Ile Asp Glu Ser
            100                 105                 110
```

```
Thr Ser Ser Tyr Arg Glu Val Gly Asp Glu Lys Gly Ser Val Thr Ser
            115                 120                 125

Ser Ser Leu Val Asp Val Asn Thr Asp Thr Gln Ala Lys Lys Thr Ser
    130                 135                 140

Val His Ser Asp Lys Lys Val Lys Val Asp Lys Pro Lys Ile Ile Pro
145                 150                 155                 160

Pro Pro Gly Ser Gly Gln Lys Ile Tyr Glu Ile Asp Pro Leu Leu Gln
                165                 170                 175

Ala His Arg Gln His Leu Asp Phe Arg Tyr Gly Gln Tyr Lys Arg Ile
            180                 185                 190

Arg Glu Glu Ile Asp Lys Tyr Glu Gly Gly Leu Asp Ala Phe Ser Arg
        195                 200                 205

Gly Tyr Glu Lys Phe Gly Phe Thr Arg Ser Ala Thr Gly Ile Thr Tyr
        210                 215                 220

Arg Glu Trp Gly Pro Gly Ala Lys Ser Ala Ala Leu Val Gly Asp Phe
225                 230                 235                 240

Asn Asn Trp Asn Pro Asn Ala Asp Val Met Thr Lys Asp Ala Phe Gly
            245                 250                 255

Val Trp Glu Ile Phe Leu Pro Asn Asn Ala Asp Gly Ser Pro Pro Ile
            260                 265                 270

Pro His Gly Ser Arg Val Lys Ile His Met Asp Thr Pro Ser Gly Ile
        275                 280                 285

Lys Asp Ser Ile Pro Ala Trp Ile Lys Phe Ser Val Gln Ala Pro Gly
        290                 295                 300

Glu Ile Pro Tyr Asn Gly Ile Tyr Tyr Asp Pro Pro Glu Glu Glu Lys
305                 310                 315                 320

Tyr Val Phe Lys His Pro Gln Pro Lys Arg Pro Gln Ser Ile Arg Ile
            325                 330                 335

Tyr Glu Ser His Ile Gly Met Ser Ser Pro Glu Pro Lys Ile Asn Thr
            340                 345                 350

Tyr Ala Asn Phe Arg Asp Asp Val Leu Pro Arg Ile Lys Lys Leu Gly
        355                 360                 365

Tyr Asn Ala Val Gln Ile Met Ala Ile Gln Glu His Ser Tyr Tyr Ala
        370                 375                 380

Ser Phe Gly Tyr His Val Thr Asn Phe Phe Ala Pro Ser Ser Arg Phe
385                 390                 395                 400

Gly Thr Pro Glu Asp Leu Lys Ser Leu Ile Asp Arg Ala His Glu Leu
            405                 410                 415

Gly Leu Leu Val Leu Met Asp Ile Val His Ser His Ser Ser Asn Asn
            420                 425                 430

Thr Leu Asp Gly Leu Asn Met Phe Asp Gly Thr Asp His Gly Tyr Phe
        435                 440                 445

His Pro Gly Ser Arg Gly Tyr His Trp Met Trp Asp Ser Arg Leu Phe
        450                 455                 460

Asn Tyr Gly Ser Trp Glu Val Leu Arg Tyr Leu Leu Ser Asn Ala Arg
465                 470                 475                 480

Trp Trp Leu Asp Glu Tyr Lys Phe Asp Gly Phe Arg Phe Asp Gly Val
            485                 490                 495

Thr Ser Met Met Tyr Thr His His Gly Leu Gln Val Ser Phe Thr Gly
            500                 505                 510

Asn Tyr Ser Glu Tyr Phe Gly Leu Ala Thr Asp Val Glu Ala Val Val
            515                 520                 525
```

```
Tyr Met Met Leu Val Asn Asp Leu Ile His Gly Leu Phe Pro Glu Ala
        530                 535                 540

Val Ser Ile Gly Glu Asp Val Ser Gly Met Pro Thr Phe Cys Leu Pro
545                 550                 555                 560

Thr Gln Asp Gly Gly Ile Gly Phe Asn Tyr Arg Leu His Met Ala Val
                565                 570                 575

Ala Asp Lys Trp Ile Glu Leu Leu Lys Lys Gln Asp Glu Asp Trp Arg
            580                 585                 590

Met Gly Asp Ile Val His Thr Leu Thr Asn Arg Arg Trp Leu Glu Lys
            595                 600                 605

Cys Val Val Tyr Ala Glu Ser His Asp Gln Ala Leu Val Gly Asp Lys
610                 615                 620

Thr Leu Ala Phe Trp Leu Met Asp Lys Asp Met Tyr Asp Phe Met Ala
625                 630                 635                 640

Leu Asp Arg Pro Ser Thr Pro Leu Ile Asp Arg Gly Ile Ala Leu His
                645                 650                 655

Lys Met Ile Arg Leu Ile Thr Met Gly Leu Gly Gly Glu Gly Tyr Leu
            660                 665                 670

Asn Phe Met Gly Asn Glu Phe Gly His Pro Glu Trp Ile Asp Phe Pro
        675                 680                 685

Arg Gly Glu Gln His Leu Pro Asn Gly Lys Ile Val Pro Gly Asn Asn
690                 695                 700

Asn Ser Tyr Asp Lys Cys Arg Arg Phe Asp Leu Gly Asp Ala Asp
705                 710                 715                 720

Tyr Leu Arg Tyr His Gly Met Gln Glu Phe Asp Arg Ala Met Gln His
                725                 730                 735

Leu Glu Glu Thr Tyr Gly Phe Met Thr Ser Glu His Gln Tyr Ile Ser
            740                 745                 750

Arg Lys Asn Glu Gly Asp Arg Val Ile Ile Phe Glu Arg Asp Asn Leu
        755                 760                 765

Val Phe Val Phe Asn Phe His Trp Thr Asn Ser Tyr Ser Asp Tyr Lys
770                 775                 780

Val Gly Cys Leu Lys Pro Gly Lys Tyr Lys Ile Val Leu Asp Ser Asp
785                 790                 795                 800

Asp Thr Leu Phe Gly Gly Phe Asn Arg Leu Asn His Thr Ala Glu Tyr
                805                 810                 815

Phe Thr Ser Glu Gly Trp Tyr Asp Asp Arg Pro Arg Ser Phe Leu Val
            820                 825                 830

Tyr Ala Pro Ser Arg Thr Ala Val Val Tyr Ala Leu Ala Asp Gly Val
        835                 840                 845

Glu Ser Glu Pro Ile Glu Leu Ser Asp Gly Val Glu Ser
850                 855                 860

<210> SEQ ID NO 37
<211> LENGTH: 2531
<212> TYPE: DNA
<213> ORGANISM: Solanum tuberosum
<220> FEATURE:
<221> NAME/KEY: CDS
<222> LOCATION: (5)..(2530)
<220> FEATURE:
<221> NAME/KEY: modified_base
<222> LOCATION: (2492)..(2492)
<223> OTHER INFORMATION: a, c, g, t, other or unknown
<220> FEATURE:
<221> NAME/KEY: modified_base
<222> LOCATION: (2499)..(2499)
<223> OTHER INFORMATION: a, c, g, t, other or unknown
```

```
<220> FEATURE:
<221> NAME/KEY: modified_base
<222> LOCATION: (2516)..(2516)
<223> OTHER INFORMATION: a, c, g, t, other or unknown
<220> FEATURE:
<221> NAME/KEY: modified_base
<222> LOCATION: (2520)..(2521)
<223> OTHER INFORMATION: a, c, g, t, other or unknown

<400> SEQUENCE: 37 ggat gct aat gtt tct gta ttc ttg aaa aag cac tct ctt tca cgg aag     49
     Ala Asn Val Ser Val Phe Leu Lys Lys His Ser Leu Ser Arg Lys
     1               5                  10                  15 atc ttg gct gaa aag tct tct tac aat tcc gaa tcc cga cct tct aca     97
Ile Leu Ala Glu Lys Ser Ser Tyr Asn Ser Glu Ser Arg Pro Ser Thr
                20                  25                  30 gtt gca gca tcg ggg aaa gtc ctt gtg cct gga ayc cag agt gat agc    145
Val Ala Ala Ser Gly Lys Val Leu Val Pro Gly Xaa Gln Ser Asp Ser
            35                  40                  45 tcc tca tcc tca aca gac caa ttt gag ttc act gag aca tct cca gaa    193
Ser Ser Ser Ser Thr Asp Gln Phe Glu Phe Thr Glu Thr Ser Pro Glu
        50                  55                  60 aat tcc cca gca tca act gat gta gat agt tca aca atg gaa cac gct    241
Asn Ser Pro Ala Ser Thr Asp Val Asp Ser Ser Thr Met Glu His Ala
    65                  70                  75 agc cag att aaa act gag aac gat gac gtt gag ccg tca agt gat ctt    289
Ser Gln Ile Lys Thr Glu Asn Asp Asp Val Glu Pro Ser Ser Asp Leu
80                  85                  90                  95 aca gga agt gtt gaa gag ctg gat ttt gct tca tca cta caa cta caa    337
Thr Gly Ser Val Glu Glu Leu Asp Phe Ala Ser Ser Leu Gln Leu Gln
                100                 105                 110 gaa ggt ggt aaa ctg gag gag tct aaa aca tta aat act tct gaa gag    385
Glu Gly Gly Lys Leu Glu Glu Ser Lys Thr Leu Asn Thr Ser Glu Glu
            115                 120                 125 aca att att gat gaa tct gat agg atc aga gag agg ggc atc cct cca    433
Thr Ile Ile Asp Glu Ser Asp Arg Ile Arg Glu Arg Gly Ile Pro Pro
        130                 135                 140 cct gga ctt ggt cag aag att tat gaa ata gac ccc ctt ttg aca aac    481
Pro Gly Leu Gly Gln Lys Ile Tyr Glu Ile Asp Pro Leu Leu Thr Asn
    145                 150                 155 tat cgt caa cac ctt gat tac agg tat tca cag tac aag aaa ctg agg    529
Tyr Arg Gln His Leu Asp Tyr Arg Tyr Ser Gln Tyr Lys Lys Leu Arg
160                 165                 170                 175 gag gca att gac aag tat gag ggt ggt ttg gaa gct ttt tct cgt ggt    577
Glu Ala Ile Asp Lys Tyr Glu Gly Gly Leu Glu Ala Phe Ser Arg Gly
                180                 185                 190 tat gaa aaa atg ggt ttc act cgt agt gct aca ggt atc act tac cgt    625
Tyr Glu Lys Met Gly Phe Thr Arg Ser Ala Thr Gly Ile Thr Tyr Arg
            195                 200                 205 gag tgg gct cct ggt gcc cag tca gct gcc ctc att gga gat ttc aac    673
Glu Trp Ala Pro Gly Ala Gln Ser Ala Ala Leu Ile Gly Asp Phe Asn
        210                 215                 220 aat tgg gac gca aat gct gac att atg act cgg aat gaa ttt ggt gtc    721
Asn Trp Asp Ala Asn Ala Asp Ile Met Thr Arg Asn Glu Phe Gly Val
    225                 230                 235 tgg gag att ttt ctg cca aat aat gtg gat ggt tct cct gca att cct    769
Trp Glu Ile Phe Leu Pro Asn Asn Val Asp Gly Ser Pro Ala Ile Pro
240                 245                 250                 255 cat ggg tcc aga gtg aag ata cgy atg gac act cca tca ggt gtt aag    817
His Gly Ser Arg Val Lys Ile Arg Met Asp Thr Pro Ser Gly Val Lys
                260                 265                 270
```

-continued

```
gat tcc att cct gct tgg atc aac tac tct tta cag ctt cct gat gaa      865
Asp Ser Ile Pro Ala Trp Ile Asn Tyr Ser Leu Gln Leu Pro Asp Glu
        275                 280                 285 att cca tat aat gga ata tat tat gat cca ccc gaa gag gag agg tat      913
Ile Pro Tyr Asn Gly Ile Tyr Tyr Asp Pro Pro Glu Glu Glu Arg Tyr
290                 295                 300 rtc ttc caa cac cca cgg cca aag aaa cca aag tcg ctg aga ata tat      961
Xaa Phe Gln His Pro Arg Pro Lys Lys Pro Lys Ser Leu Arg Ile Tyr
305                 310                 315 gaa tct cat att gga atg agt agt ccg gag cct aaa att aac tca tac     1009
Glu Ser His Ile Gly Met Ser Ser Pro Glu Pro Lys Ile Asn Ser Tyr
320                 325                 330                 335 gtg aat ttt aga gat gaa gtt ctt cct cgc ata aaa aas ctt ggg tac     1057
Val Asn Phe Arg Asp Glu Val Leu Pro Arg Ile Lys Xaa Leu Gly Tyr
                340                 345                 350 aat gcg gtg caa att atg gct att caa gag cat tct tat tat gct agt     1105
Asn Ala Val Gln Ile Met Ala Ile Gln Glu His Ser Tyr Tyr Ala Ser
                355                 360                 365 ttt ggt tat cat gtc aca aat ttt ttt gca cca agc agc cgt ttt gga     1153
Phe Gly Tyr His Val Thr Asn Phe Phe Ala Pro Ser Ser Arg Phe Gly
            370                 375                 380 acg ccc gac gac ctt aag tct ttg att gat aaa gct cat gag cta gga     1201
Thr Pro Asp Asp Leu Lys Ser Leu Ile Asp Lys Ala His Glu Leu Gly
385                 390                 395 att gtt gtt ctc atg gac att gtt cac agc cat gca tca aat aat act     1249
Ile Val Val Leu Met Asp Ile Val His Ser His Ala Ser Asn Asn Thr
400                 405                 410                 415 tta gat gga ctg aac atg ttt gac ggc aca gat agt tgt tac ttt cac     1297
Leu Asp Gly Leu Asn Met Phe Asp Gly Thr Asp Ser Cys Tyr Phe His
                420                 425                 430 tct gga gct cgt ggt tat cat tgg atg tgg gat tcc cgc ctc ttt aac     1345
Ser Gly Ala Arg Gly Tyr His Trp Met Trp Asp Ser Arg Leu Phe Asn
            435                 440                 445 tat gga aac tgg gag gta ctt agg tat ctt ctc tca aat gcg aga tgg     1393
Tyr Gly Asn Trp Glu Val Leu Arg Tyr Leu Leu Ser Asn Ala Arg Trp
        450                 455                 460 tgg ttg gat gag ttc aaa ttt gat gga ttt aga ttt gat ggt gtg aca     1441
Trp Leu Asp Glu Phe Lys Phe Asp Gly Phe Arg Phe Asp Gly Val Thr
465                 470                 475 tca atg atg tat act cac cac gga tta tcg gtg gga ttc act ggg aac     1489
Ser Met Met Tyr Thr His His Gly Leu Ser Val Gly Phe Thr Gly Asn
480                 485                 490                 495 tac gag gaa tac ttt gga ctc gca act gat gtg gat gct gtt gtg tat     1537
Tyr Glu Glu Tyr Phe Gly Leu Ala Thr Asp Val Asp Ala Val Val Tyr
                500                 505                 510 ctg atg ctg gtc aac gat ctt att cac ggg ctt ttc cca gat gca att     1585
Leu Met Leu Val Asn Asp Leu Ile His Gly Leu Phe Pro Asp Ala Ile
                515                 520                 525 acc att ggt gaa gat gtt agc gga atg ccg aca ttt tgt att ccc gtt     1633
Thr Ile Gly Glu Asp Val Ser Gly Met Pro Thr Phe Cys Ile Pro Val
            530                 535                 540 caa gat ggg ggt gtt ggc ttt gac tat cgg ctg cat atg gca att gct     1681
Gln Asp Gly Gly Val Gly Phe Asp Tyr Arg Leu His Met Ala Ile Ala
545                 550                 555 gat aaa tgg att gag ttg ctc aag aaa cgg gat gag gat tgg aga gtg     1729
Asp Lys Trp Ile Glu Leu Leu Lys Lys Arg Asp Glu Asp Trp Arg Val
560                 565                 570                 575 ggt gat att gtt cat aca ctg aca aat aga aga tgg tcg gaa aag tgt     1777
Gly Asp Ile Val His Thr Leu Thr Asn Arg Arg Trp Ser Glu Lys Cys
                580                 585                 590
```

| | | | | | | | | | | | | | | |
|---|---|---|---|---|---|---|---|---|---|---|---|---|---|---|
| gtt | tca | tmc | gct | gaa | agt | cat | gat | caa | gct | cta | gtc | ggt | gat | aaa act | 1825 |
| Val | Ser | Xaa | Ala | Glu | Ser | His | Asp | Gln | Ala | Leu | Val | Gly | Asp | Lys Thr | |
| | | 595 | | | | | 600 | | | | | 605 | | | |

```
gtt tca tmc gct gaa agt cat gat caa gct cta gtc ggt gat aaa act    1825
Val Ser Xaa Ala Glu Ser His Asp Gln Ala Leu Val Gly Asp Lys Thr
        595                 600                 605 ata gca tyc tgg ctg atg gac aag gat atg tat gat ttt atg gct ctg    1873
Ile Ala Xaa Trp Leu Met Asp Lys Asp Met Tyr Asp Phe Met Ala Leu
        610                 615                 620 gat aga ccg tca aca tca tta ata gat cgt ggg ata gca ttg cac aag    1921
Asp Arg Pro Ser Thr Ser Leu Ile Asp Arg Gly Ile Ala Leu His Lys
625                 630                 635 atg att agg ctt gta act atg gga tta gga gga gaa ggg tac cta aat    1969
Met Ile Arg Leu Val Thr Met Gly Leu Gly Gly Glu Gly Tyr Leu Asn
640                 645                 650                 655 ttc atg gga aat gaa ttc ggc cac cct gag tgg att gat ttc cct agg    2017
Phe Met Gly Asn Glu Phe Gly His Pro Glu Trp Ile Asp Phe Pro Arg
            660                 665                 670 gct gar caa cac ctc tct gat ggc tca gta att ccc gga aac caa ttc    2065
Ala Glu Gln His Leu Ser Asp Gly Ser Val Ile Pro Gly Asn Gln Phe
            675                 680                 685 agt tat gat aaa tgc aga cgg aga ttt gac ctg gga gat gca gaa tat    2113
Ser Tyr Asp Lys Cys Arg Arg Arg Phe Asp Leu Gly Asp Ala Glu Tyr
            690                 695                 700 tta aga tac cat ggg ttg caa gaa ttt gac cgg gct atg cag tat ctt    2161
Leu Arg Tyr His Gly Leu Gln Glu Phe Asp Arg Ala Met Gln Tyr Leu
705                 710                 715 gaa gat aaa tat gag ttt atg act tca gaa cac cag ttc ata tca cga    2209
Glu Asp Lys Tyr Glu Phe Met Thr Ser Glu His Gln Phe Ile Ser Arg
720                 725                 730                 735 aag gat gaa gga gat agg atg att gta ttt gaa ara gga aac cta gtt    2257
Lys Asp Glu Gly Asp Arg Met Ile Val Phe Glu Xaa Gly Asn Leu Val
            740                 745                 750 ttt gtc ttt aat ttt cac tgg aca aat agc tat tca gac tat cgc ata    2305
Phe Val Phe Asn Phe His Trp Thr Asn Ser Tyr Ser Asp Tyr Arg Ile
            755                 760                 765 ggc tgc ctg aag cct gga aaa tac aag gtt ggc ttg gac tca gat gat    2353
Gly Cys Leu Lys Pro Gly Lys Tyr Lys Val Gly Leu Asp Ser Asp Asp
            770                 775                 780 cca ctt ttt ggt ggc ttc ggg aga att gat cat aat gcc gaa tat ttc    2401
Pro Leu Phe Gly Gly Phe Gly Arg Ile Asp His Asn Ala Glu Tyr Phe
785                 790                 795 acc tct gaa gga tcg tat gat gat cgy ccy cgy yca att atg gtg tat    2449
Thr Ser Glu Gly Ser Tyr Asp Asp Arg Pro Arg Xaa Ile Met Val Tyr
800                 805                 810                 815 gca cct agt aga aca gca gtg gtc tat gca cta gta gac aaa nta gaa    2497
Ala Pro Ser Arg Thr Ala Val Val Tyr Ala Leu Val Asp Lys Xaa Glu
            820                 825                 830 gna gaa gaa gaa gaa gaa ncc gnn gaa gaa ttt t                      2531
Xaa Glu Glu Glu Glu Glu Xaa Xaa Glu Glu Phe
            835                 840
```

<210> SEQ ID NO 38
<211> LENGTH: 842
<212> TYPE: PRT
<213> ORGANISM: Solanum tuberosum
<220> FEATURE:
<221> NAME/KEY: MOD_RES
<222> LOCATION: (43)..(43)
<223> OTHER INFORMATION: Thr or Ile
<220> FEATURE:
<221> NAME/KEY: MOD_RES
<222> LOCATION: (304)..(304)
<223> OTHER INFORMATION: Val or Ile
<220> FEATURE:

```
<221> NAME/KEY: MOD_RES
<222> LOCATION: (348)..(348)
<223> OTHER INFORMATION: Lys or Asn
<220> FEATURE:
<221> NAME/KEY: MOD_RES
<222> LOCATION: (594)..(594)
<223> OTHER INFORMATION: Tyr or Ser
<220> FEATURE:
<221> NAME/KEY: MOD_RES
<222> LOCATION: (610)..(610)
<223> OTHER INFORMATION: Ser or Phe
<220> FEATURE:
<221> NAME/KEY: MOD_RES
<222> LOCATION: (747)..(747)
<223> OTHER INFORMATION: Arg or Lys
<220> FEATURE:
<221> NAME/KEY: MOD_RES
<222> LOCATION: (811)..(811)
<223> OTHER INFORMATION: Pro or Ser
<220> FEATURE:
<221> NAME/KEY: MOD_RES
<222> LOCATION: (830)..(830)
<223> OTHER INFORMATION: Ile, Val, or Leu
<220> FEATURE:
<221> NAME/KEY: MOD_RES
<222> LOCATION: (832)..(832)
<223> OTHER INFORMATION: Glu, Gly, Ala or Val
<220> FEATURE:
<221> NAME/KEY: MOD_RES
<222> LOCATION: (838)..(838)
<223> OTHER INFORMATION: Thr, Ala, Pro or Ser
<220> FEATURE:
<221> NAME/KEY: MOD_RES
<222> LOCATION: (839)..(839)
<223> OTHER INFORMATION: Glu, Asp, Gly, Ala or Val

<400> SEQUENCE: 38

Ala Asn Val Ser Val Phe Leu Lys Lys His Ser Leu Ser Arg Lys Ile
1               5                   10                  15

Leu Ala Glu Lys Ser Ser Tyr Asn Ser Glu Ser Arg Pro Ser Thr Val
            20                  25                  30

Ala Ala Ser Gly Lys Val Leu Val Pro Gly Xaa Gln Ser Asp Ser Ser
        35                  40                  45

Ser Ser Ser Thr Asp Gln Phe Glu Phe Thr Glu Thr Ser Pro Glu Asn
50                  55                  60

Ser Pro Ala Ser Thr Asp Val Asp Ser Ser Thr Met Glu His Ala Ser
65                  70                  75                  80

Gln Ile Lys Thr Glu Asn Asp Asp Val Glu Pro Ser Ser Asp Leu Thr
                85                  90                  95

Gly Ser Val Glu Glu Leu Asp Phe Ala Ser Ser Leu Gln Leu Gln Glu
            100                 105                 110

Gly Gly Lys Leu Glu Glu Ser Lys Thr Leu Asn Thr Ser Glu Glu Thr
        115                 120                 125

Ile Ile Asp Glu Ser Asp Arg Ile Arg Glu Arg Gly Ile Pro Pro Pro
130                 135                 140

Gly Leu Gly Gln Lys Ile Tyr Glu Ile Asp Pro Leu Leu Thr Asn Tyr
145                 150                 155                 160

Arg Gln His Leu Asp Tyr Arg Tyr Ser Gln Tyr Lys Lys Leu Arg Glu
                165                 170                 175

Ala Ile Asp Lys Tyr Glu Gly Gly Leu Glu Ala Phe Ser Arg Gly Tyr
            180                 185                 190

Glu Lys Met Gly Phe Thr Arg Ser Ala Thr Gly Ile Thr Tyr Arg Glu
        195                 200                 205

Trp Ala Pro Gly Ala Gln Ser Ala Ala Leu Ile Gly Asp Phe Asn Asn
210                 215                 220
```

-continued

Trp Asp Ala Asn Ala Asp Ile Met Thr Arg Asn Glu Phe Gly Val Trp
225                 230                 235                 240

Glu Ile Phe Leu Pro Asn Asn Val Asp Gly Ser Pro Ala Ile Pro His
            245                 250                 255

Gly Ser Arg Val Lys Ile Arg Met Asp Thr Pro Ser Gly Val Lys Asp
            260                 265                 270

Ser Ile Pro Ala Trp Ile Asn Tyr Ser Leu Gln Leu Pro Asp Glu Ile
        275                 280                 285

Pro Tyr Asn Gly Ile Tyr Tyr Asp Pro Pro Glu Glu Glu Arg Tyr Xaa
    290                 295                 300

Phe Gln His Pro Arg Pro Lys Lys Pro Lys Ser Leu Arg Ile Tyr Glu
305                 310                 315                 320

Ser His Ile Gly Met Ser Ser Pro Glu Pro Lys Ile Asn Ser Tyr Val
                325                 330                 335

Asn Phe Arg Asp Glu Val Leu Pro Arg Ile Lys Xaa Leu Gly Tyr Asn
            340                 345                 350

Ala Val Gln Ile Met Ala Ile Gln Glu His Ser Tyr Tyr Ala Ser Phe
            355                 360                 365

Gly Tyr His Val Thr Asn Phe Phe Ala Pro Ser Ser Arg Phe Gly Thr
        370                 375                 380

Pro Asp Asp Leu Lys Ser Leu Ile Asp Lys Ala His Glu Leu Gly Ile
385                 390                 395                 400

Val Val Leu Met Asp Ile Val His Ser His Ala Ser Asn Asn Thr Leu
                405                 410                 415

Asp Gly Leu Asn Met Phe Asp Gly Thr Asp Ser Cys Tyr Phe His Ser
            420                 425                 430

Gly Ala Arg Gly Tyr His Trp Met Trp Asp Ser Arg Leu Phe Asn Tyr
        435                 440                 445

Gly Asn Trp Glu Val Leu Arg Tyr Leu Leu Ser Asn Ala Arg Trp Trp
450                 455                 460

Leu Asp Glu Phe Lys Phe Asp Gly Phe Arg Phe Asp Gly Val Thr Ser
465                 470                 475                 480

Met Met Tyr Thr His His Gly Leu Ser Val Gly Phe Thr Gly Asn Tyr
            485                 490                 495

Glu Glu Tyr Phe Gly Leu Ala Thr Asp Val Asp Ala Val Val Tyr Leu
                500                 505                 510

Met Leu Val Asn Asp Leu Ile His Gly Leu Phe Pro Asp Ala Ile Thr
            515                 520                 525

Ile Gly Glu Asp Val Ser Gly Met Pro Thr Phe Cys Ile Pro Val Gln
        530                 535                 540

Asp Gly Gly Val Gly Phe Asp Tyr Arg Leu His Met Ala Ile Ala Asp
545                 550                 555                 560

Lys Trp Ile Glu Leu Leu Lys Lys Arg Asp Glu Asp Trp Arg Val Gly
            565                 570                 575

Asp Ile Val His Thr Leu Thr Asn Arg Arg Trp Ser Glu Lys Cys Val
            580                 585                 590

Ser Xaa Ala Glu Ser His Asp Gln Ala Leu Val Gly Asp Lys Thr Ile
    595                 600                 605

Ala Xaa Trp Leu Met Asp Lys Asp Met Tyr Asp Phe Met Ala Leu Asp
    610                 615                 620

Arg Pro Ser Thr Ser Leu Ile Asp Arg Gly Ile Ala Leu His Lys Met
625                 630                 635                 640

-continued

```
Ile Arg Leu Val Thr Met Gly Leu Gly Gly Glu Gly Tyr Leu Asn Phe
                645                 650                 655
Met Gly Asn Glu Phe Gly His Pro Glu Trp Ile Asp Phe Pro Arg Ala
            660                 665                 670
Glu Gln His Leu Ser Asp Gly Ser Val Ile Pro Gly Asn Gln Phe Ser
        675                 680                 685
Tyr Asp Lys Cys Arg Arg Phe Asp Leu Gly Asp Ala Glu Tyr Leu
    690                 695                 700
Arg Tyr His Gly Leu Gln Glu Phe Asp Arg Ala Met Gln Tyr Leu Glu
705                 710                 715                 720
Asp Lys Tyr Glu Phe Met Thr Ser Glu His Gln Phe Ile Ser Arg Lys
                725                 730                 735
Asp Glu Gly Asp Arg Met Ile Val Phe Glu Xaa Gly Asn Leu Val Phe
            740                 745                 750
Val Phe Asn Phe His Trp Thr Asn Ser Tyr Ser Asp Tyr Arg Ile Gly
        755                 760                 765
Cys Leu Lys Pro Gly Lys Tyr Lys Val Gly Leu Asp Ser Asp Pro
    770                 775                 780
Leu Phe Gly Gly Phe Gly Arg Ile Asp His Asn Ala Glu Tyr Phe Thr
785                 790                 795                 800
Ser Glu Gly Ser Tyr Asp Asp Arg Pro Arg Xaa Ile Met Val Tyr Ala
                805                 810                 815
Pro Ser Arg Thr Ala Val Val Tyr Ala Leu Val Asp Lys Xaa Glu Xaa
            820                 825                 830
Glu Glu Glu Glu Glu Xaa Xaa Glu Glu Phe
        835                 840
```

<210> SEQ ID NO 39
<211> LENGTH: 3003
<212> TYPE: DNA
<213> ORGANISM: Solanum tuberosum

<400> SEQUENCE: 39

```
gatggggcct tgaactcagc aatttgacac tcagttagtt acactgccat cacttatcag      60
atctctattt tttctcttaa ttccaaccaa ggaatgaata aaagataga tttgtaaaaa       120
ccctaaggag agaagaagaa agatggtgta tacactctct ggagttcgtt ttcctactgt      180
tccatcagtg tacaaatcta atggattcag cagtaatggt gatcggagga atgctaatat      240
ttctgtattc ttgaaaaaac actctctttc acggaagatc ttggctgaaa agtcttctta     300
caattccgaa tcccgacctt ctacaattgc agcatcgggg aaagtccttg tgcctggaat     360
ccagagtgat agctcctcat cctcaacaga tcaatttgag ttcgctgaga catctccaga      420
aaattcccca gcatcaactg atgtagatag ttcaacaatg aacacgcta gccagattaa      480
aactgagaac gatgacgttg agccgtcaag tgatcttaca ggaagtgttg aagagctgga      540
ttttgcttca tcactacaac tacaagaagg tggtaaactg gaggagtcta aaacattaaa      600
tacttctgaa gagacaatta ttgatgaatc tgataggatc agagagaggg gcatccctcc      660
acctggactt ggtcagaaga tttatgaaat agaccccctt ttgacaaact atcgtcaaca      720
ccttgattac aggtattcac agtacaagaa actgagggag gcaattgaca gtatgagggg      780
tggtttggaa gcttttctc gtggttatga agaatgggt ttcactcgta gtgctacagg       840
tatcacttac cgtgagtggg ctcctggtgc ccagtcagct gccctcattg gggatttcaa      900
caattgggac gcaaatgctg actttatgac tcggaatgaa tttggtgtct gagagatttt     960
```

```
tctgccaaat aatgtggatg gttctcctgc aattcctcat gggtccagag tgaagatacg    1020 tatgacact ccatcaggtg ttaaggattc cattcctgct tggatcaact actctttaca    1080
gcttcctgat gaaattccat ataatggaat atattatgat ccacccgaag aggagaggta    1140
tatcttccaa cacccacggc caaagaaacc aaagtcggtg agaatatatg aatctcatat    1200
tggaatgagt agtccggagc ctaaaattaa ctcatacgtg aattttagag atgaagttct    1260
tcctcgcata aaaaagctt gggtacaatg cggtgcaaat tatggctatt caagagcatt    1320
cttattatgc tagttttggt tatcatgtca caattttttt tgcaccaagc agccgttttg    1380
gaacgcccga cgaccttaag tctttgattg ataaagctca tgagctagga attgttgttc    1440
tcatggacat tgttcacagc catgcatcaa ataatacttt agatggactg aacatgtttg    1500
acggcacaga tagttgttac tttcactctg agctcgtgg ttatcattgg atgtgggatt    1560
tccgcctctt taactatgga aactgggagg tacttaggta tcttctctca aatgcgagat    1620
ggtggttgga tgagttcaaa tttgatggat ttagatttga tggtgtgaca tcaatgatgt    1680
gtactcacca cggattatcg gtgggattca ctgggaacta cgaggaatac tttggactcg    1740
caactgatgt ggatgctgtt gtgtatctga tgctggtcaa cgatcttatt catgggctt    1800 tcccagatgc aattaccatt ggtgaagatg ttagcggaat gccgacattt tgtgttcccg    1860
ttcaagatgg gggtgttggc tttgactatc ggctgcatat ggcaattgct gataaatgga    1920
ttgagttgct caagaaacgg gatgaggatt ggagagtggg tgatattgtt catacactga    1980
caaatagaag atggtcggaa aagtgtgttt catacgctga aagtcatgat caagctctag    2040
tcggtgataa aactatagca ttctggctga tggacaagga tatgtatgat tttatggctc    2100
tggatagacc gtcaacatca ttaatagatc gtgggatagc attacacaag atgattaggc    2160
ttgtaactat gggattagga ggagaagggt acctaaattt catgggaaat gaattcggcc    2220
accctgagtg gattgatttc cctagggctg acaacacct ctctgatggc tcagtaattc    2280
ccagaaacca attcagttat gataaatgca gacggagatt tgacctggga gatgcagaat    2340
atttaagata ccgtgggttg caagaatttg accgggctat gcagtatctt gaagataaat    2400
atgagtttat gacttcagaa caccagttca tatcacgaaa ggatgaagga gataggatga    2460
ttgtatttga aaaggaaac ctagttttg tctttaattt tcactggaca aaaggctatt    2520
cagactatcg cataggctgc ctgaagcctg gaaaatacaa ggttgccttg gactcagatg    2580
atccactttt tggtggcttc gggagaattg atcataatgc cgaatatttc acctttgaag    2640
gatggtatga tgatcgtcct cgttcaatta tggtgtatgc acctagtaga acagcagtgg    2700
tctatgcact agtagacaaa gaagaagaag aagaagaaga agtagcagta gtagaagaag    2760
tagtagtaga agaagaatga acgaacttgt gatcgcgttg aaagatttga acgccacata    2820
gagcttcttg acgtatctgg caatattgca ttagtcttgg cggaatttca tgtgacaaca    2880
ggtttgcaat tctttccact attagtagtg caacgatata cgcagagatg aagtgctgaa    2940
caaaaacata tgtaaaatcg atgaatttat gtcgaatgct gggacgatcg aattcctgca    3000
gcc                                                                  3003
```

<210> SEQ ID NO 40
<211> LENGTH: 2975
<212> TYPE: DNA
<213> ORGANISM: Solanum tuberosum

<400> SEQUENCE: 40

```
ttgatgggcc ttgaactcag caatttgaca ctcagttagt tacactccta tcacttatca      60
```

-continued

```
gatctctatt ttttctctta attccaacca ggggaatgaa taaaaggata gatttgtaaa       120
aaccctaagg agagaagaag aaagatggtg tatatactct ctggagttcg ttttcctact       180
gttccatcag tgtacaaatc taatggattc agcagtaatg gtgatcggag gaatgctaat       240
gtttctgtat tcttgaaaaa gcactctctt tcacggaaga tcttggctga aaagtcttct       300
tacaattccg aattccgacc ttctacagtt gcagcatcgg ggaaagtcct tgtgcctgga       360
acccagagtg atagctcctc atcctcaaca gaccaatttg agttcactga gacatctcca       420
gaaaattccc cagcatcaac tgatgtagat agttcaacaa tggaacacgc tagccagatt       480
aaaactgaga acgatgacgt tgagccgtca agtgatctta caggaagtgt tgaagagctg       540
gattttgctt catcactaca actacaagaa ggtggtaaac tggaggagtc taaaacatta       600
aatacttctg aagagacaat tattgatgaa tctgatagga tcagagagag gggcatccct       660
ccacctggac ttggtcagaa gatttatgaa atagacccccc ttttgacaaa ctatcgtcaa       720
caccttgatt acaggtattc acagtacaag aaactgaggg aggcaattga caagtatgag       780
ggtggtttgg aagcttttct cgtggttatg aaaaaatggg tttcactcgt agtgctacag       840
gtatcactta ccgtgagtgg gctcctggtg cccagtcagc tgccctcatt ggagatttca       900
acaattggga cgcaaatgct gacattatga ctcggaatga atttggtgtc tgggagattt       960
ttctgccaaa taatgtggat ggttctcctg caattcctca tgggtccaga gtgaagatac       1020
gtatggacac tccatcaggt gttaaggatt ccattcctgc ttggatcaac tactcttttac      1080 agcttcctga tgaaattcca tataatggaa tatattatga tccacccgaa gaggagaggt      1140
atatcttcca acaccacgg ccaaagaaac caaagtcgct gagaatatat gaatctcata      1200
ttggaatgag tagtccggag cctaaaatta actcatacgt gaattttaga gatgaagttc      1260
ttcctcgcat aaaaaagctt gggtacaatg cgctgcgaat tatggctatt caagagcatt      1320
cttattatgc tagttttggt tatcatgtca caaattttt tgcaccaagc agccgttttg      1380
gaacgcccga cgaccttaag tcttcgattg ataaagctca tgagctagga attgttgttc      1440
tcatggacat cgttcacagc catgcatcaa ataaatacttt agatggactg aacatgtttg      1500
acggcaccga tagttgttac tttcactctg gagctcgtgg ttatcattgg atgtgggatt      1560
ccgcctcttt aactatggaa actgggaggt acttaggtat cttctctcaa atgcgagatg      1620
gtggttggat gagttcaaat ttgatggatt tagattcgat ggtgtgacat caatgatgta      1680
tactcaccac ggattatcgg tgggattcac tgggaactac gaggaatact ttggactcgc      1740
aactgatgtg gatgctgttg tgtatctgat gctggtcaac gatcttattc ataggctttt      1800
cccagatgca attaccattg gtgaagatgt tagcggaatg ccgacatttt gtattcccgt      1860
tcaagatggg ggtgttggct ttgactatcg gctgcatatg gcaattgctg ataaatggat      1920
tgagttgctc aagaaacggg atgaggattg gagagtgggt gatattgttc atacactgac      1980
aaatagaaga tggtcggaaa agtgtgtttc atacgctgaa agtcatgatc aagctctagt      2040
cggtgataaa actatagcat tctggctgat ggacaaggat atgtatgatt ttatggctct      2100
ggatagaccg ccaacatcat taatagatcg tgggatagca ttgcacaaga tgattaggct      2160
tgtaactatg ggattaggag gagaagggta cctaaatttc atgggaaatg aattcggcca      2220
ccctgagtgg attgatttcc ctagggctga gccacacctt tctgatggct cagtaattcc      2280
cggaaaccaa ttcagttatg ataaatgcag acggagattt gacctgggag atgcagaata      2340
tttaagatac catgggttac aagaatttga ctgggctatg cagtatcttg aagataaata      2400
```

-continued

```
tgagtttatg acttcagaac accagttcat atcacgaaag gatgaaggag ataggatgat    2460
tgtatttgaa agaggaaacc tagttttcgt ctttaatttt cactggacaa atagctattc    2520
agactatcgc ataggctgcc tgaagcctgg aaaatacaag gttgtcttgg actcagatga    2580 tccactttt ggtggcttcg ggagaattga tcataatgcc gaatatttca cctctgaagg     2640
atcgtatgat gatcgtcctt gttcaattat ggtgtatgca cctagtagaa cagcagtggt    2700
ctatgcacta gtagacaaac tagaagtagc agtagtagaa gaacccattg aagaatgaac    2760
gaacttgtga tcgcgttgaa agatttgaac gttacttggt catccacata gagcttcttg    2820
acatcagtct tggcggaatt gcatgtgaca acaaggtttg cagttctttc cactattagt    2880
agtccaccga tatacgcaga gatgaagtgc tgaacaaaca tatgtaaaat cgatgaattt    2940
atgtcgaatg ctgggacgat cgaattcctg cagcc                              2975
```

<210> SEQ ID NO 41
<211> LENGTH: 3033
<212> TYPE: DNA
<213> ORGANISM: Solanum tuberosum

<400> SEQUENCE: 41

```
ttgatggggc cttgaactca gcaatttgac actcagttag ttacactcct atcacttatc     60
agatctctat ttttctctt aattccaacc aaggaatgaa taaaggata gatttgtaaa     120 aaccctaagg agagaagaag aaagatggtg tatacactct ctggagttcg ttttcctact    180
gttccatcag tgtacaaatc taatggattc agcagtaatg gtgatcggag gaatgctaat    240
gtttctgtat tcttgaaaaa gcactctctt tcacggaaga tcttggctga aaagtcttct    300
tacaattccg aattccgacc ttctacagtt gcagcatcgg ggaaagtcct tgtgcctgga    360
acccagagtg atagctcctc atcctcaaca gaccaatttg agttcactga gacatctcca    420
gaaaattccc cagcatcaac tgatgtagat agttcaacaa tggaacacgc tagccagatt    480
aaaactgaga acgatgacgt tgagccgtca agtgatctta caggaagtgt tgaagagctg    540
gattttgctt catcactaca actacaagaa ggtggtaaac tggaggagtc taaaacatta    600
aatacttctg aagagacaat tattgatgaa tctgatagga tcagagagag gggcatccct    660
ccacctggac ttggtcagaa gatttatgaa atagaccccc ttttgacaaa ctatcgtcaa    720
caccttgatt acaggtattc acagtacaag aaactgaggg aggcaattga caagtatgag    780 ggtggttttgg aagccttttc tcgtggttat gaaaaaatgg gtttcactcg tagtgctaca    840
ggtatcactt accgtgagtg ggctcttggt gcccagtcag ctgccctcat ggagatttc    900 aacaattggg acgcaaatgc tgacattatg actcggaatg aatttggtgt ctgggagatt    960
tttctgccaa ataatgtgga tggttctcct gcaattcctc atgggtccag agtgaagata    1020
cgtatggaca ctccatcagg tgttaaggat tccattcctg cttggatcaa ctactcttta    1080
cagcttcctg atgaaattcc atataatgga atacattatg atccacccga agaggagagg    1140
tatatcttcc aacacccacg gccaagaaaa ccaaagtcgc tgagaatata tgaatctcat    1200
attggaatga gtagtccgga gcctaaaatt aactcatacg tgaattttag agatgaagtt    1260
cttcctcgca taaaaaagct tgggtacaat gcgctgcaaa ttatggctat tcaagagcat    1320
tcttattacg ctagttttgg ttatcatgtc acaaattttt ttgcaccaag cagccgtttt    1380
ggaacgcccg acgacttaa gtctttgatt gataaagctc atgagctagg aattgttgtt    1440 ctcatgggaca ttgttcacag ccatgcatca ataatactt tagatggact gaacatgttt    1500
gactgcaccg atagttgtta cttcactct ggagctcgtg gttatcattg gatgtgggat    1560
```

```
tcccgcctct ttaactatgg aaactgggag gtacttaggt atcttctctc aaatgcgaga    1620
tggtggttgg atgcgttcaa atttgatgga tttagatttg atggtgtgac atcaatgatg    1680
tatattcacc acggattatc ggtgggattc actgggaact acgaggaata ctttggactc    1740
gcaactgatg tggatgctgt tgtgtatctg atgctggtca acgatcttat tcatgggctt    1800
ttcccagatg caattaccat tggtgaagat gttagcggaa tgccgacatt ttgtattccc    1860
gtccaagagg ggggtgttgg ctttgactat cggctgcata tggcaattgc tgataaacgg    1920
attgagttgc tcaagaaacg ggatgaggat tggagagtgg gtgatattgt tcatacactg    1980
acaaatagaa gatggtcgga aaagtgtgtt tcatacgctg aaagtcatga tcaagctcta    2040
gtcggtgata aaactatagc attctggctg atggacaagg atatgtatga ttttatggct    2100
ctggatagac cgtcaacatc attaatagat cgtgggatag cattgcacaa gatgattagg    2160
cttgtaacta tgggattagg aggagaaggg tacctaaatt tcatgggaaa tgaattcggc    2220
caccctgagt ggattgattt ccctagggct gaacaacacc tctctgatgg ctcagtaatc    2280
cccgaaaacc aattcagtta tgataaatgc agacggagtg ttgacctggg agatgcagaa    2340
tatttaagat accgtgggtt gcaagaattt gaccggccta tgcagtatct tgaagataaa    2400 tatgagtttta tgacttcaga acaccagttc atatcacgaa aggatgaagg agataggatg    2460
attgtatttg aaaaggaaa cctagttttt gtctttaatt ttcactggac aaaaagctat    2520
tcagactatc gcatagcctg cctgaagcct ggaaaataca aggttgcctt ggactcagat    2580
gatccacttt ttggtggctt cgggagaatt gatcataatg ccgaatattt caccttgaa    2640 ggatggtatg atgatcgtcc tcgttcaatt atggtgtatg caccttgtaa aacagcagtg    2700
gtctatgcac tagtagacaa agaagaagaa gaagaagaa aagaagaaga agaagtagca    2760
gcagtagaag aagtagtagt agaagaagaa tgaacgaact tgtgatcgcg ttgaaagatt    2820
tgaacgctac atagagcttc ttgacgtatc tggcaatatt gcatcagtct tggcggaatt    2880
tcatgtgaca caaggtttgc aattctttcc actattagta gtgcaacgat atacgcagag    2940
atgaagtgct gaacaaacat atgtaaaatc gatgaattta tgtcgaatgc tgggacgatc    3000
gaattcctgc aggccggggg accccttagt tct                                  3033
```

<210> SEQ ID NO 42
<211> LENGTH: 847
<212> TYPE: PRT
<213> ORGANISM: Solanum tuberosum

<400> SEQUENCE: 42

Met Arg Gly Ser His His His His His His Gly Ile Leu Ala Glu Lys
1               5                   10                  15

Ser Ser Tyr Asn Ser Glu Phe Arg Pro Ser Thr Val Ala Ala Ser Gly
            20                  25                  30

Lys Val Leu Val Pro Gly Thr Gln Ser Asp Ser Ser Ser Ser Ser Thr
        35                  40                  45

Asn Gln Phe Glu Phe Thr Glu Thr Ser Pro Asn Ser Pro Ala Ser
    50                  55                  60

Thr Asp Val Asp Ser Ser Thr Met Glu His Ala Ser Gln Ile Lys Thr
65                  70                  75                  80

Glu Asn Asp Asp Val Glu Pro Ser Ser Asp Leu Thr Gly Ser Val Glu
                85                  90                  95

Glu Leu Asp Phe Ala Ser Ser Leu Gln Leu Gln Glu Gly Gly Lys Leu
            100                 105                 110

-continued

```
Glu Glu Ser Lys Thr Leu Asn Thr Ser Glu Thr Ile Ile Asp Glu
        115                 120                 125
Ser Asp Arg Ile Arg Glu Arg Gly Ile Pro Pro Gly Leu Gly Gln
130                 135                 140
Lys Ile Tyr Glu Ile Asp Pro Leu Leu Thr Asn Tyr Arg Gln His Leu
145                 150                 155                 160
Asp Tyr Arg Tyr Ser Gln Tyr Lys Lys Leu Arg Glu Ala Ile Asp Lys
                165                 170                 175
Tyr Glu Gly Gly Leu Glu Ala Phe Ser Arg Gly Tyr Glu Lys Met Gly
                180                 185                 190
Phe Thr Arg Ser Ala Thr Gly Ile Thr Tyr Arg Glu Trp Ala Pro Gly
            195                 200                 205
Ala Gln Ser Ala Ala Leu Ile Gly Asp Phe Asn Asn Trp Asp Ala Asn
        210                 215                 220
Ala Asp Ile Met Thr Arg Asn Glu Phe Gly Val Trp Glu Ile Phe Leu
225                 230                 235                 240
Pro Asn Asn Val Asp Gly Ser Pro Ala Ile Pro His Gly Ser Arg Val
                245                 250                 255
Lys Ile Arg Met Asp Thr Pro Ser Gly Val Lys Asp Ser Ile Pro Ala
                260                 265                 270
Trp Ile Asn Tyr Ser Ser Gln Leu Pro Asp Glu Ile Pro Tyr Asn Gly
            275                 280                 285
Ile Tyr Tyr Asp Pro Pro Glu Glu Glu Arg Tyr Ile Phe Gln His Pro
        290                 295                 300
Arg Pro Lys Lys Pro Lys Ser Leu Arg Ile Tyr Glu Ser His Ile Gly
305                 310                 315                 320
Met Ser Ser Pro Glu Pro Lys Ile Asn Ser Tyr Val Asn Phe Arg Asp
                325                 330                 335
Glu Val Leu Pro Arg Ile Lys Lys Leu Gly Tyr Asn Ala Val Gln Ile
                340                 345                 350
Met Ala Ile Gln Glu His Ser Tyr Tyr Ala Ser Phe Gly Tyr His Val
            355                 360                 365
Thr Asn Phe Phe Ala Pro Ser Ser Arg Phe Gly Thr Pro Asp Asp Leu
        370                 375                 380
Lys Ser Leu Ile Asp Lys Ala His Glu Leu Gly Ile Val Val Leu Met
385                 390                 395                 400
Asp Ile Val His Ser His Ala Ser Asn Asn Thr Leu Asp Gly Leu Asn
                405                 410                 415
Met Phe Asp Gly Thr Asp Ser Cys Tyr Phe His Ser Gly Ala Arg Gly
                420                 425                 430
Tyr His Trp Met Trp Asp Ser Arg Leu Phe Asn Tyr Gly Asn Trp Glu
            435                 440                 445
Val Leu Arg Tyr Leu Leu Ser Asn Ala Arg Trp Trp Leu Asp Glu Phe
        450                 455                 460
Lys Phe Asp Gly Phe Arg Phe Asp Gly Val Thr Ser Met Met Tyr Thr
465                 470                 475                 480
His His Gly Leu Ser Val Gly Phe Thr Gly Asn Tyr Glu Glu Tyr Phe
                485                 490                 495
Gly Leu Ala Thr Asp Val Asp Ala Val Val Tyr Leu Met Leu Val Asn
                500                 505                 510
Asp Leu Ile His Gly Leu Phe Pro Asp Ala Ile Thr Ile Gly Glu Asp
            515                 520                 525
```

-continued

```
Val Ser Gly Met Pro Thr Phe Cys Ile Pro Val Gln Asp Gly Gly Val
    530                 535                 540
Gly Phe Asp Tyr Arg Leu His Met Ala Ile Ala Asp Lys Trp Ile Glu
545                 550                 555                 560
Leu Leu Lys Lys Arg Asp Glu Asp Trp Arg Val Gly Asp Ile Val His
                565                 570                 575
Thr Leu Thr Asn Arg Arg Trp Ser Glu Lys Cys Val Ser Tyr Ala Glu
            580                 585                 590
Ser His Asp Gln Ala Leu Val Gly Asp Lys Thr Ile Ala Phe Trp Leu
        595                 600                 605
Met Asp Lys Asp Met Tyr Asp Phe Met Ala Leu Asp Arg Pro Pro Thr
    610                 615                 620
Ser Leu Ile Asp Arg Gly Ile Ala Leu His Lys Met Ile Arg Leu Val
625                 630                 635                 640
Thr Met Gly Leu Gly Gly Glu Gly Tyr Leu Asn Phe Met Gly Asn Glu
                645                 650                 655
Phe Gly His Pro Glu Trp Ile Asp Phe Pro Arg Ala Glu Gln His Leu
            660                 665                 670
Ser Asp Asp Ser Val Ile Pro Gly Asn Gln Phe Ser Tyr Asp Lys Cys
        675                 680                 685
Arg Arg Arg Phe Asp Leu Gly Asp Ala Glu Tyr Leu Arg Tyr Arg Gly
    690                 695                 700
Leu Gln Glu Phe Asp Arg Ala Met Gln Tyr Leu Glu Asp Lys Tyr Glu
705                 710                 715                 720
Phe Met Thr Ser Glu His Gln Phe Ile Ser Arg Lys Asp Glu Gly Asp
                725                 730                 735
Arg Met Ile Val Phe Glu Lys Gly Asn Leu Val Phe Val Phe Asn Phe
            740                 745                 750
His Trp Thr Lys Ser Tyr Ser Asp Tyr Arg Ile Gly Cys Leu Lys Pro
        755                 760                 765
Gly Lys Tyr Lys Val Ala Leu Asp Ser Asp Asp Pro Leu Phe Gly Gly
    770                 775                 780
Phe Gly Arg Ile Asp His Asn Ala Glu Tyr Phe Thr Phe Glu Gly Trp
785                 790                 795                 800
Tyr Asp Asp Arg Pro Arg Ser Ile Met Val Tyr Ala Pro Cys Arg Thr
                805                 810                 815
Ala Val Val Tyr Ala Leu Val Asp Lys Glu Glu Glu Glu Glu Glu Glu
            820                 825                 830
Glu Glu Glu Val Ala Val Val Glu Val Val Val Glu Glu Glu
        835                 840                 845

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Asn Lys Arg Ile Asp Leu
  1               5
```

PLANT STARCH COMPOSITION

CROSS-REFERENCE TO RELATED APPLICATION

This application is a divisional of application Ser. No. 08/945,722, filed Sep. 18, 1997 now U.S. Pat. No. 6,825,342, which is a 371 of PCT/GB96/01075 filed May 3, 1996.

FIELD OF THE INVENTION

This invention relates to novel nucleotide sequences, polypeptides encoded thereby, vectors and host cells and host organisms comprising one or more of the novel sequences, and to a method of altering one or more characteristics of an organism. The invention also relates to starch having novel properties and to uses thereof.

BACKGROUND OF THE INVENTION

Starch is the major form of carbon reserve in plants, constituting 50% or more of the dry weight of many storage organs—e.g. tubers, seeds of cereals. Starch is used in numerous food and industrial applications. In many cases, however, it is necessary to modify the native starches, via chemical or physical means, in order to produce distinct properties to suit particular applications. It would be highly desirable to be able to produce starches with the required properties directly in the plant, thereby removing the need for additional modification. To achieve this via genetic engineering requires knowledge of the metabolic pathway of starch biosynthesis. This includes characterisation of genes and encoded gene products which catalyse the synthesis of starch. Knowledge about the regulation of starch biosynthesis raises the possibility of "re-programming" biosynthetic pathways to create starches with novel properties that could have new commercial applications.

The commercially useful properties of starch derive from the ability of the native granular form to swell and absorb water upon suitable treatment. Usually heat is required to cause granules to swell in a process known as gelatinization, which has been defined (W A Atwell et al, Cereal Foods World 33, 306–311, 1988) as " . . . the collapse (disruption) of molecular orders within the starch granule manifested in irreversible changes in properties such as granular swelling, native crystallite melting, loss of birefringence, and starch solubilization. The point of initial gelatinization and the range over which it occurs is governed by starch concentration, method of observation, granule type, and heterogeneities within the granule population under observation". A number of techniques are available for the determination of gelatinization as induced by heating, a convenient and accurate method being differential scanning calorimetry, which detects the temperature range and enthalpy associated with the collapse of molecular orders within the granule. To obtain accurate and meaningful results, the peak and/or onset temperature of the endotherm observed by differential scanning calorimetry is usually determined.

The consequence of the collapse of molecular orders within starch granules is that the granules are capable of taking up water in a process known as pasting, which has been defined (W A Atwell et al, Cereal Foods World 33, 306–311, 1988) as " . . . the phenomenon following gelatinization in the dissolution of starch. It involves granular swelling, exudation of molecular components from the granule, and eventually, total disruption of the granules". The best method of evaluating pasting properties is considered to be the viscoamylograph (Atwell et al, 1988 cited above) in which the viscosity of a stirred starch suspension is monitored under a defined time/temperature regime. A typical viscoamylograph profile for potato starch shows an initial rise in viscosity, which is considered to be due to granule swelling. In addition to the overall shape of the viscosity response in a viscoamylograph, a convenient quantitative measure is the temperature of initial viscosity development (onset). FIG. 1 shows such a typical viscosity profile for potato starch, during and after cooking, and includes stages A–D which correspond to viscosity onset (A), maximum viscosity (B), complete dispersion (C) and reassociation of molecules (or retrogradation, D). In the figure, the dotted line represents viscosity (in stirring number units) of a 10% w/w starch suspension and the unbroken line shows the temperature in degrees centigrade. At a certain point, defined by the viscosity peak, granule swelling is so extensive that the resulting highly expanded structures are susceptible to mechanically-induced fragmentation under the stirring conditions used. With increased heating and holding at 95° C., further reduction in viscosity is observed due to increased fragmentation of swollen granules. This general profile has previously always been found for native potato starch.

After heating starches in water to 95° C. and holding at that temperature (for typically 15 minutes), subsequent cooling to 50° C. results in an increase in viscosity due to the process of retrogradation or set-back. Retrogradation (or set-back) is defined (Atwell et al., 1988 cited above) as " . . . a process which occurs when the molecules comprising gelatinised starch begin to reassociate in an ordered structure . . . ". At 50° C., it is primarily the amylose component which reassociates, as indicated by the increase in viscoamylograph viscosity for starch from normal maize (21.6% amylose) compared with starch from waxy maize (1.1% amylose) as shown in FIG. 2. FIG. 2 is a viscoamylograph of 10% w/w starch suspensions from waxy maize (solid line), conventional maize (dots and dashes), high amylose variety (HYLON® V starch, dotted line) and a very high amylose variety (HYLON® VII starch, crosses). The temperature profile is also shown by a solid line, as in FIG. 1. The extent of viscosity increase in the viscoamylograph on cooling and holding at 50° C. depends on the amount of amylose which is able to reassociate due to its exudation from starch granules during the gelatinization and pasting processes. A characteristic of amylose-rich starches from maize plants is that very little amylose is exuded from granules by gelatinization and pasting up to 95° C., probably due to the restricted swelling of the granules. This is illustrated in FIG. 2 which shows low viscosities for a high amylose (44.9%) starch (HYLON® V starch) from maize during gelatinization and pasting at 95° C. and little increase in viscosity on cooling and holding at 50° C. This effect is more extreme for a higher amylose content (58%, as in HYLON® VII starch), which shows even lower viscosities in the viscoamylograph test (FIG. 2). For commercially-available high amylose starches (currently available from maize plants, such as those described above), processing at greater than 100° C. is usually necessary in order to generate the benefits of high amylose contents with respect to increased rates and strengths of reassociation, but use of such high temperatures is energetically unfavourable and costly. Accordingly, there is an unmet need for starches of high amylose content which can be processed below 100° C. and still show enhanced levels of reassociation, as indicated for example by viscoamylograph measurements.

The properties of potato starch are useful in a variety of both food and non-food (paper, textiles, adhesives etc.)

applications. However, for many applications, properties are not optimum and various chemical and physical modifications well known in the art are undertaken in order to improve useful properties. Two types of property manipulation which would be of use are: the controlled alteration of gelatinization and pasting temperatures; and starches which suffer less granular fragmentation during pasting than conventional starches.

Currently the only ways of manipulating the gelatinization and pasting temperatures of potato starch are by the inclusion of additives such as sugars, polyhydroxy compounds of salts (Evans & Haisman, Starke 34, 224–231, 1982) or by extensive physical or chemical pre-treatments (e.g. Stute, Starke 44, 205–214, 1992). The reduction of granule fragmentation during pasting can be achieved either by extensive physical pretreatments (Stute, Starke 44, 205–214, 1992) or by chemical cross-linking. Such processes are inconvenient and inefficient. It is therefore desirable to obtain plants which produce starch which intrinsically possesses such advantageous properties.

Starch consists of two main polysaccharides, amylose and amylopectin. Amylose is a generally linear polymer containing α-1,4 linked glucose units, while amylopectin is a highly branched polymer consisting of a α-1,4 linked glucan backbone with α-1,6 linked glucan branches. In most plant storage reserves amylopectin constitutes about 75% of the starch content. Amylopectin is synthesized by the concerted action of soluble starch synthase and starch branching enzyme [α-1,4 glucan: α-1,4 glucan 6-glycosyltransferase, EC 2.4.1.18]. Starch branching enzyme (SBE) hydrolyses α-1,4 linkages and rejoins the cleaved glucan, via an α-1,6 linkage, to an acceptor chain to produce a branched structure. The physical properties of starch are strongly affected by the relative abundance of amylose and amylopectin, and SBE is therefore a crucial enzyme in determining both the quantity and quality of starches produced in plant systems.

In most plants studied to date e.g. maize (Boyer & Preiss, 1978 Biochem. Biophys. Res. Comm. 80, 169–175), rice (Smyth, 1988 Plant Sci. 57, 1–8) and pea (Smith, Planta 175, 270–279), two forms of SBE have been identified, each encoded by a separate gene. A recent review by Burton et al., (1995 The Plant Journal 7, 3–15) has demonstrated that the two forms of SBE constitute distinct classes of the enzyme such that, in general, enzymes of the same class from different plants may exhibit greater similarity than enzymes of different classes from the same plant. In their review, Burton et al. termed the two respective enzyme families class "A" and class "B", and the reader is referred thereto (and to the references cited therein) for a detailed discussion of the distinctions between the two classes. One general distinction of note would appear to be the presence, in class A SBE molecules, of a flexible N-terminal domain, which is not found in class B molecules. The distinctions noted by Burton et al. are relied on herein to define class A and class B SBE molecules, which terms are to be interpreted accordingly.

However in potato, only one isoform of the SBE molecule (belonging to class B) has thus far been reported and only one gene cloned (Blennow & Johansson, 1991 Phytochem. 30, 437–444, and Koβmann et al., 1991 Mol. Gen. Genet. 230, 39–44). Further, published attempts to modify the properties of starch in potato plants (by preventing expression of the single known SBE) have generally not succeeded (e.g. Müller-Rober & Koβmann 1994 Plant Cell and Environment 17, 601–613).

SUMMARY OF THE INVENTION

In a first aspect the invention provides a nucleotide sequence encoding an effective portion of a class A starch branching enzyme (SBE) obtainable from potato plants.

Preferably the nucleotide sequence encodes a polypeptide comprising an effective portion of the amino acid sequence shown in FIG. 5 (excluding the sequence MINKRIDL, (SEQ ID No: 43) which does not represent part of the SBE molecule), or a functional equivalent thereof (which term is discussed below). The amino acid sequence shown in FIG. 5 (Seq ID No. 15) includes a leader sequence which directs the polypeptide, when synthesized in potato cells, to the amyloplast. Those skilled in the art will recognise that the leader sequence is removed to produce a mature enzyme and that the leader sequence is therefore not essential for enzyme activity. Accordingly, an "effective portion" of the polypeptide is one which possesses sufficient SBE activity to complement the branching enzyme mutation in E. coli KV 832 cells (described below) and which is active when expressed in E. coli in the phosphorylation stimulation assay. An example of an incomplete polypeptide which nevertheless constitutes an "effective portion" is the mature enzyme lacking the leader sequence. By analogy with the pea class A SBE sequence, the potato class A sequence shown in FIG. 5 probably possesses a leader sequence of about 48 amino acid residues, such that the N terminal amino acid sequence is thought to commence around the glutamic acid residue (E) at position 56 (EKSSYN. . . etc. residues 56–61 of SEQ ID No: 15). Those skilled in the art will appreciate that an effective portion of the enzyme may well omit other parts of the sequence shown in the figure without substantial detrimental effect. For example, the C-terminal glutamic acid-rich region could be reduced in length, or possibly deleted entirely, without abolishing class A SBE activity. A comparison with other known SBE sequences, especially other class A SBE sequences (see for example, Burton et al, 1995 cited above), should indicate those portions which are highly conserved (and thus likely to be essential for activity) and those portions which are less well conserved (and thus are more likely to tolerate sequence changes without substantial loss of enzyme activity).

Conveniently the nucleotide sequence will comprise substantially nucleotides 289 to 2790 of the DNA sequence (Seq ID No. 14) shown in FIG. 5 (which nucleotides encode the mature enzyme) or a functional equivalent thereof, and may also include further nucleotides at the 5' or 3' end. For example, for ease of expression, the sequence will desirably also comprise an in-frame ATG start codon, and may also encode a leader sequence. Thus, in one embodiment, the sequence further comprises nucleotides 145 to 288 of the sequence shown in FIG. 5. Other embodiments are nucleotides 228 to 2855 of the sequence labelled "psbe2con.seq" in FIG. 8, and nucleotides 57 to 2564 of the sequence shown in FIG. 12 (preferably comprising an in-frame ATG start codon, such as the sequence of nucleotides 24 to 56 in the same Figure), or functional equivalents of the aforesaid sequences.

The term "functional equivalent" as applied herein to nucleotide sequences is intended to encompass those sequences which differ in their nucleotide composition to that shown in FIG. 5 but which, by virtue of the degeneracy of the genetic code, encode polypeptides having identical or substantially identical amino acid sequences. It is intended that the term should also apply to sequences which are sufficiently homologous to the sequence of the invention that they can hybridise to the complement thereof under stringent hybridisation conditions—such equivalents will preferably possess at least 85%, more preferably at least 90%, and most preferably at least 95% sequence homology with the sequence of the invention as exemplified by nucleotides 289 to 2790 of the DNA sequence shown in FIG. 5. It will be apparent to those skilled in the art that the nucleotide sequence of the invention may also find useful application when present as an "antisense" sequence. Accordingly, functionally equivalent sequences will also include those sequences which can hybridise, under stringent hybridisation conditions, to the sequence of the invention (rather than the complement thereof). Such "antisense" equivalents will preferably possess at least 85%, more preferably at least 90%, and most preferably 95% sequence homology with the complement of the sequence of the invention as exemplified by nucleotides 289 to 2790 of the DNA sequence shown in FIG. 5. Particular functional equivalents are shown, for example, in FIGS. 8 and 10 (if one disregards the various frameshift mutations noted therein).

The invention also provides vectors, particularly expression vectors, comprising the nucleotide sequence of the invention. The vector will typically comprise a promoter and one or more regulatory signals of the type well known to those skilled in the art. The invention also includes provision of cells transformed (which term encompasses transduction and transfection) with a vector comprising the nucleotide sequence of the invention.

The invention further provides a class A SBE polypeptide, obtainable from potato plants. In particular the invention provides the polypeptide in substantially pure form, especially in a form free from other plant-derived (especially potato plant-derived) components, which can be readily accomplished by expression of the relevant nucleotide sequence in a suitable non-plant host (such as any one of the yeast strains routinely used from expression purposes, e.g. *Pichia spp.* or *Saccharomyces spp*). Typically the enzyme will substantially comprise the sequence of amino acid residues 49 to 882 (i.e., amino acid residues 56 to 889 of SEQ ID No: 15) shown in FIG. 5 (disregarding the sequence MINKRIDL, SEQ ID No: 43, which is not part of the enzyme), or a functional equivalent thereof. The polypeptide of the invention may be used in a method of modifying starch in vitro, comprising treating starch under suitable conditions (e.g. appropriate temperature, pH, etc) with an effective amount of the polypeptide according to the invention.

The term "functional equivalent", as applied herein to amino acid sequences, is intended to encompass amino acid sequences substantially similar to that shown in FIG. 5, such that the polypeptide possesses sufficient activity to complement the branching enzyme mutation in *E. coli* KV 832 cells (described below) and which is active in *E. coli* in the phosphorylation stimulation assay. Typically such functionally equivalent amino acid sequences will preferably possess at least 85%, more preferably at least 90%, and most preferably at least 95% sequence identity with the amino acid sequence of the mature enzyme (i.e. minus leader sequence) shown in FIG. 5. Those skilled in the art will appreciate that conservative substitutions may be made generally throughout the molecule without substantially affecting the activity of the enzyme. Moreover, some non-conservative substitutions may be tolerated, especially in the less highly conserved regions of the molecule. Such substitutions may be made, for example, to modify slightly the activity of the enzyme. The polypeptide may, if desired, include a leader sequence, such as that exemplified by residues 1 to 48 of the amino acid sequence shown in FIG. 5, although other leader sequences and signal peptides and the like are known and may be included.

A portion of the nucleotide sequence of the invention has been introduced into a plant and found to affect the characteristics of the plant. In particular, introduction of the sequence of the invention, operably linked in the antisense orientation to a suitable promoter, was found to reduce the amount of branched starch molecules in the plant. Additionally, it has recently been demonstrated in other experimental systems that "sense suppression" can also occur (i.e. expression of an introduced sequence operably linked in the sense orientation can interfere, by some unknown mechanism, with the expression of the native gene), as described by Matzke & Matzke (1995 Plant Physiol. 107, 679–685). Any one of the methods mentioned by Matzke & Matzke could, in theory, be used to affect the expression in a host of a homologous SBE gene.

It is believed that antisense methods are mainly operable by the production of antisense mRNA which hybridises to the sense mRNA, preventing its translation into functional polypeptide, possibly by causing the hybrid RNA to be degraded (e.g. Sheehy et al., 1988 PNAS 85, 8805–8809; Van der Krol et al., Mol. Gen. Genet. 220, 204–212). Sense suppression also requires homology between the introduced sequence and the target gene, but the exact mechanism is unclear. It is apparent however that, in relation to both antisense and sense suppression, neither a full length nucleotide sequence, nor a "native" sequence is essential. Preferably the "effective portion" used in the method will comprise at least one third of the full length sequence, but by simple trial and error other fragments (smaller or larger) may be found which are functional in altering the characteristics of the plant.

Thus, in a further aspect the invention provides a method of altering the characteristics of a plant, comprising introducing into the plant an effective portion of the sequence of the invention operably linked to a suitable promoter active in the plant. Conveniently the sequence will be linked in the anti-sense orientation to the promoter. Preferably the plant is a potato plant. Conveniently, the characteristic altered relates to the starch content and/or starch composition of the plant (i.e. amount and/or type of starch present in the plant).

Preferably the method of altering the characteristics of the plant will also comprise the introduction of one or more further sequences, in addition to an effective portion of the sequence of the invention. The introduced sequence of the invention and the one or more further sequences (which may be sense or antisense sequences) may be operably linked to a single promoter (which would ensure both sequences were transcribed at essentially the same time), or may be operably linked to separate promoters (which may be necessary for optimal expression). Where separate promoters are employed they may be identical to each other or different. Suitable promoters are well known to those skilled in the art and include both constitutive and inducible types. Examples include the CaMV 35S promoter (e.g. single or tandem repeat) and the patatin promoter. Advantageously the promoter will be tissue-specific. Desirably the promoter will cause expression of the operably linked sequence at substantial levels only in the tissue of the plant where starch synthesis and/or starch storage mainly occurs. Thus, for example, where the sequence is introduced into a potato plant, the operably linked promoter may be tuber-specific, such as the patatin promoter.

Desirably, for example, the method will also comprise the introduction of an effective portion of a sequence encoding a class B SBE, operably linked in the antisense orientation to a suitable promoter active in the plant. Desirably the further sequence will comprise an effective portion of the sequence encoding the potato class B SBE molecule. Conveniently the further sequence will comprise an effective portion of the sequence described by Blennow & Johansson (1991 Phytochem. 30, 437–444) or that disclosed in WO92/11375. More preferably, the further sequence will comprise at least an effective portion of the sequence disclosed in International Patent Application No. WO 95/26407. Use of antisense sequences against both class A and class B SBE in combination has now been found by the present inventors to result in the production of starch having very greatly altered properties (see below). Those skilled in the art will appreciate the possibility that, if the plant already comprises a sense or antisense sequence which efficiently inhibits the class B SBE activity, introduction of a sense or antisense sequence to inhibit class A SBE activity (thereby producing a plant with inhibition of both class A and class B activity) might alter greatly the properties of the starch in the plant, without the need for introduction of one or more further sequences. Thus the sequence of the invention is conveniently introduced into plants already having low levels of class A and/or class B SBE activity, such that the inhibition resulting from the introduction of the sequence of the invention is likely to have a more pronounced effect.

The sequence of the invention, and the one or more further sequences if desired, can be introduced into the plant by any one of a number of well-known techniques (e.g. Agrobacterium-mediated transformation, or by "biolistic" methods). The sequences are likely to be most effective in inhibiting SBE activity in potato plants, but theoretically could be introduced into any plant. Desirable examples include pea, tomato, maize, wheat, rice, barley, sweet potato and cassava plants. Preferably the plant will comprise a natural gene encoding an SBE molecule which exhibits reasonable homology with the introduced nucleic acid sequence of the invention.

In another aspect, the invention provides a plant cell, or a plant or the progeny thereof, which has been altered by the method defined above. The progeny of the altered plant may be obtained, for example, by vegetative propagation, or by crossing the altered plant and reserving the seed so obtained. The invention also provides parts of the altered plant, such as storage organs. Conveniently, for example, the invention provides tubers comprising altered starch, said tubers being obtained from an altered plant or the progeny thereof. Potato tubers obtained from altered plants (or the progeny thereof) will be particularly useful materials in certain industrial applications and for the preparation and/or processing of foodstuffs and may be used, for example, to prepare low-fat waffles and chips (amylose generally being used as a coating to prevent fat uptake), and to prepare mashed potato (especially "instant" mashed potato) having particular characteristics.

In particular relation to potato plants, the invention provides a potato plant or part thereof which, in its wild type possesses an effective SBE A gene, but which plant has been altered such that there is no effective expression of an SBE A polypeptide within the cells of at least part of the plant. The plant may have been altered by the method defined above, or may have been selected by conventional breeding to be deleted for the class A SBE gene, presence or absence of which can be readily determined by screening samples of the plants with a nucleic acid probe or antibody specific for the potato class A gene or gene product respectively.

The invention also provides starch extracted from a plant altered by the method defined above, or the progeny of such a plant, the starch having altered properties compared to starch extracted from equivalent, but unaltered, plants. The invention further provides a method of making altered starch, comprising altering a plant by the method defined above and extracting therefrom starch having altered properties compared to starch extracted from equivalent, but unaltered, plants. Use of nucleotide sequences in accordance with the invention has allowed the present inventors to produce potato starches having a wide variety of novel properties.

In particular the invention provides the following: a plant (especially a potato plant) altered by the method defined above, containing starch which, when extracted from the plant, has an elevated endotherm peak temperature as judged by DSC, compared to starch extracted from a similar, but unaltered, plant; a plant (especially a potato plant) altered by the method defined above, containing starch which, when extracted from the plant, has an elevated viscosity onset temperature (conveniently elevated by 10–25° C.) as judged by viscoamylograph compared to starch extracted from a similar, but unaltered, plant; a plant (especially a potato plant) altered by the method defined above, containing starch which, when extracted from the plant, has a decreased peak viscosity (conveniently decreased by 240–700SNUs) as judged by viscoamylograph compared to starch extracted from a similar, but unaltered, plant; a plant (especially a potato plant) altered by the method defined above, containing starch which, when extracted from the plant, has an increased pasting viscosity (conveniently increased by 37–260SNUs) as judged by viscoamylograph compared to starch extracted from a similar, but unaltered, plant; a plant (especially a potato plant) altered by the method defined above, containing starch which, when extracted from the plant, has an increased set-back viscosity (conveniently increased by 224–313 SNUs) as judged by viscoamylograph compared to starch extracted from a similar, but unaltered, plant; a plant (especially a potato plant) altered by the method defined above, containing starch which, when extracted from the plant, has a decreased set-back viscosity as judged by viscoamylograph compared to starch extracted from a similar, but unaltered, plant; and a plant (especially a potato plant) altered by the method defined above, containing starch which, when extracted from the plant, has an elevated amylose content as judged by iodometric assay (i.e. by the method of Morrison & Laignelet 1983, cited above) compared to starch extracted from a similar, but unaltered, plant. The invention also provides for starch obtainable or obtained from such plants as aforesaid.

In particular the invention provides for starch which, as extracted from a potato plant by wet milling at ambient temperature, has one or more of the following properties, as judged by viscoamylograph analysis performed according to the conditions defined below: viscosity onset temperature in the range 70–95° C. (preferably 75–95° C.); peak viscosity in the range 500–12 stirring number units; pasting viscosity in the range 214–434 stirring number units; set-back viscosity in the range 450–618 or 14–192 stirring number units; or displays no significant increase in viscosity during viscoamylograph. Peak, pasting and set-back viscosities are defined below. Viscosity onset temperature is the temperature at which there is a sudden, marked increase in viscosity from baseline levels during viscoamylograph, and is a term well-known to those skilled in the art.

In other particular embodiments, the invention provides starch which as extracted from a potato plant by wet milling at ambient temperature has a peak viscosity in the range 200–500 SNUs and a set-back viscosity in the range 275–618 SNUs as judged by viscoamylograph according to the protocol defined below; and starch which as extracted from a potato plant by wet milling at ambient temperature has a viscosity which does not decrease between the start of the heating phase (step 2) and the start of the final holding phase (step 5) and has a set-back viscosity of 303 SNUs or less as judged by viscoamylograph according to the protocol defined below.

For the purposes of the present invention, viscoamylograph conditions are understood to pertain to analysis of a 10% (w/w) aqueous suspension of starch at atmospheric pressure, using a Newport Scientific Rapid Visco Analyser with a heating profile of: holding at 50° C. for 2 minutes (step 1), heating from 50 to 95° C. at a rate of 1.5° C. per minute (step 2), holding at 95° C. for 15 minutes (step 3), cooling from 95 to 50° C. at a rate of 1.5° C. per minute (step 4), and then holding at 50° C. for 15 minutes (step 5). Peak viscosity may be defined for present purposes as the maximum viscosity attained during the heating phase (step 2) or the holding phase (step 3) of the viscoamylograph. Pasting viscosity may be defined as the viscosity attained by the starch suspensions at the end of the holding phase (step 3) of the viscoamylograph. Set-back viscosity may be defined as the viscosity of the starch suspension at the end of step 5 of the viscoamylograph.

In yet another aspect the invention provides starch from a potato plant having an apparent amylose content (% w/w) of at least 35%, as judged by iodometric assay according to the method described by Morrison & Laignelet (1983 J. Cereal Science 1, 9–20). Preferably the starch will have an amylose content of at least 40%, more preferably at least 50%, and most preferably at least 66%. Starch obtained directly from a potato plant and having such properties has not hitherto been produced. Indeed, as a result of the present invention, it is now possible to generate in vivo potato starch which has some properties analogous to the very high amylose starches (e.g. HYLON® VII starch) obtainable from maize.

Starches with high (at least 35%) amylose contents find commercial application as, amongst other reasons, the amylose component of starch reassociates more strongly and rapidly than the amylopectin component during retrogradation processes. This may result, for example, in pastes with higher viscosities, gels of greater cohesion, or films of greater strength for starches with high (at least 35%) compared with normal (less than 35%) amylose contents. Alternatively, starches may be obtained with very high amylose contents, such that the granule structure is substantially preserved during heating, resulting in starch suspensions which demonstrate substantially no increase in viscosity during cooking (i.e. there is no significant viscosity increase during viscoamylograph conditions defined above). Such starches typically exhibit a viscosity increase of less than 10% (preferably less than 5%) during viscoamylograph under the conditions defined above.

In commerce, these valuable properties are currently obtained from starches of high amylose content derived from maize plants. It would be of commercial value to have an alternative source of high amylose starches from potato as other characteristics such as granule size, organoleptic properties and textural qualities may distinguish application performances of high amylose starches from maize and potato plants.

Thus high amylose starch obtained by the method of the present invention may find application in many different technological fields, which may be broadly categorised into two groups: food products and processing; and "Industrial" applications. Under the heading of food products, the novel starches of the present invention may find application as, for example, films, barriers, coatings or gelling agents. In general, high amylose content starches absorb less fat during frying than starches with low amylose content, thus the high amylose content starches of the invention may be advantageously used in preparing low fat fried products (e.g. potato chips, crisps and the like). The novel starches may also be employed with advantage in preparing confectionery and in granular and retrograded "resistant" starches. "Resistant" starch is starch which is resistant to digestion by α-amylase. As such, resistant starch is not digested by α-amylases present in the human small intestine, but passes into the colon where it exhibits properties similar to soluble and insoluble dietary fibre. Resistant starch is thus of great benefit in foodstuffs due to its low calorific value and its high dietary fibre content. Resistant starch is formed by the retrogradation (akin to recrystallization) of amylose from starch gels. Such retrogradation is inhibited by amylopectin. Accordingly, the high amylose starches of the present invention are excellent starting materials for the preparation of resistant starch. Suitable methods for the preparation of resistant starch are well-known to those skilled in the art and include, for example, those described in U.S. Pat. No. 5,051,271 and U.S. Pat. No. 5,281,276. Conveniently the resistant starches provided by the present invention comprise at least 5% total dietary fibre, as judged by the method of Prosky et al., (1985 J. Assoc. Off. Anal. Chem. 68, 677), mentioned in U.S. Pat. No. 5,281,276.

Under the heading of "Industrial" applications, the novel starches of the invention may be advantageously employed, for example, in corrugating adhesives, in biodegradable products such as loose fill packaging and foamed shapes, and in the production of glass fibers and textiles.

Those skilled in the art will appreciate that the novel starches of the invention may, if desired, be subjected in vitro to conventional enzymatic, physical and/or chemical modification, such as cross-linking, introduction of hydrophobic groups (e.g. octenyl succinic acid, dodecyl succinic acid), or derivatization (e.g. by means of esterification or etherification).

In yet another aspect the invention provides high (35% or more) amylose starches which generate paste viscosities greater than those obtained from high amylose starches from maize plants after processing at temperatures below 100° C. This provides the advantage of more economical starch gelatinization and pasting treatments through the use of lower processing temperatures than are currently required for high amylose starches from maize plants.

The invention will now be further described by way of illustrative example and with reference to the drawings, of which:

FIG. 4a shows the amino acid alignment of the C-terminal portion of starch branching enzyme isoforms from various sources (SEQ ID Nos 21–26, respectively in order of appearance): amino acid residues matching the consensus sequence are shaded;

FIG. 4b shows the alignment of DNA sequences of various starch branching enzyme isoforms which encode a conserved amino acid sequence (SEQ ID Nos 27–32, respectively in order of appearance);

FIG. 5 shows the DNA sequence (Seq ID No. 14) and predicted amino acid sequence (Seq ID No. 15) of a full length potato class A SBE cDNA clone obtained by PCR;

FIG. 6 shows a comparison of the most highly conserved part of the amino acid sequences of potato class A (uppermost sequence, SEQ ID No: 33) and class B (lowermost sequence, SEQ ID No: 34) SBE molecules;

FIG. 7 shows a comparison of the amino acid sequence of the full length potato class A (uppermost sequence, SEQ ID No: 35) and pea (lowermost sequence, SEQ ID No: 36) class A SBE molecules;

FIG. 8 shows a DNA alignment of various full length potato class A SBE clones obtained by the inventors (SEQ ID No: 13, residues 1–3012 of SEQ ID Nos: 14, 12 and 18, respectively in order of appearance);

FIG. 9 shows the DNA sequence of a potato class A SBE clone determined by direct sequencing of PCR products (SEQ ID No: 37), together with the predicted amino acid sequence (SEQ ID No: 38);

FIG. 10 is a multiple DNA alignment of various full length potato SBE A clones obtained by the inventors (SEQ ID Nos: 39–41 and 16–17, respectively in order of appearance);

FIG. 12 shows the DNA sequence (SEQ ID No: 19) and predicted amino acid sequence (SEQ ID No: 42) of the full length potato class A SBE clone as present in the plasmid pSJ90.

EXAMPLES

Example 1

Cloning of Potato Class A SBE

Figure 3:
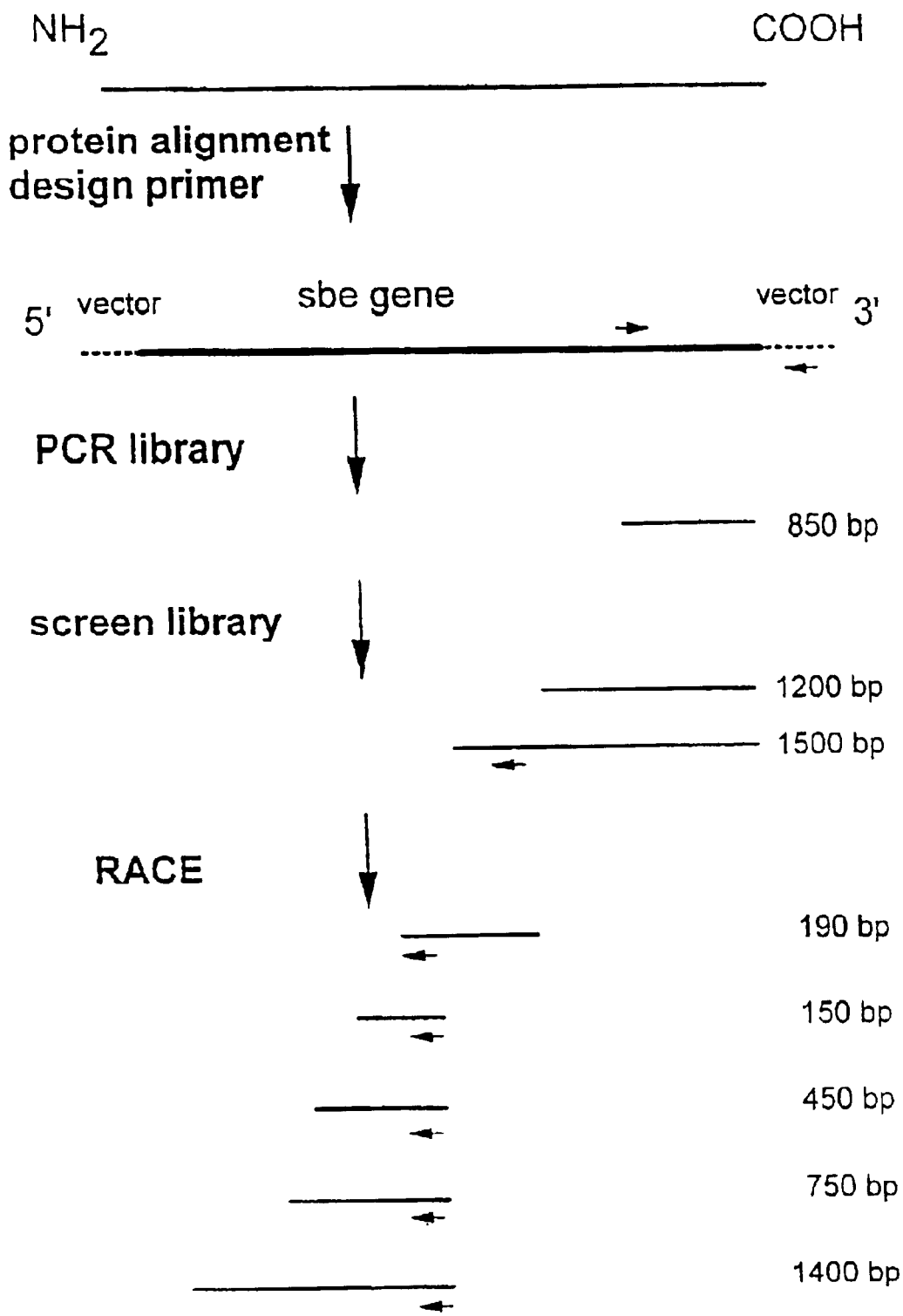
FIG. 3 is a schematic representation of the cloning strategy used by the present inventors.
Figure 4A:
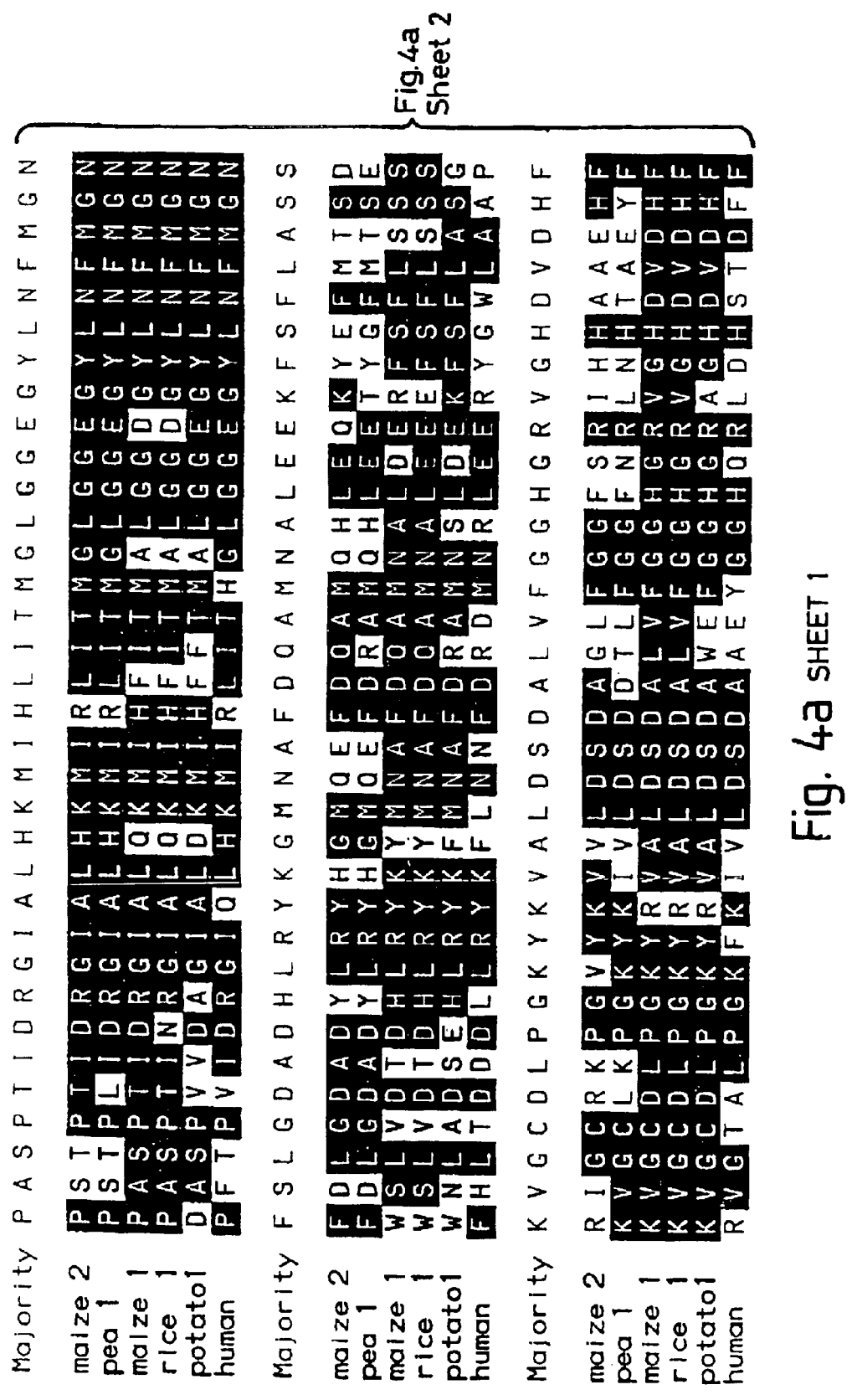
Figure 4A:
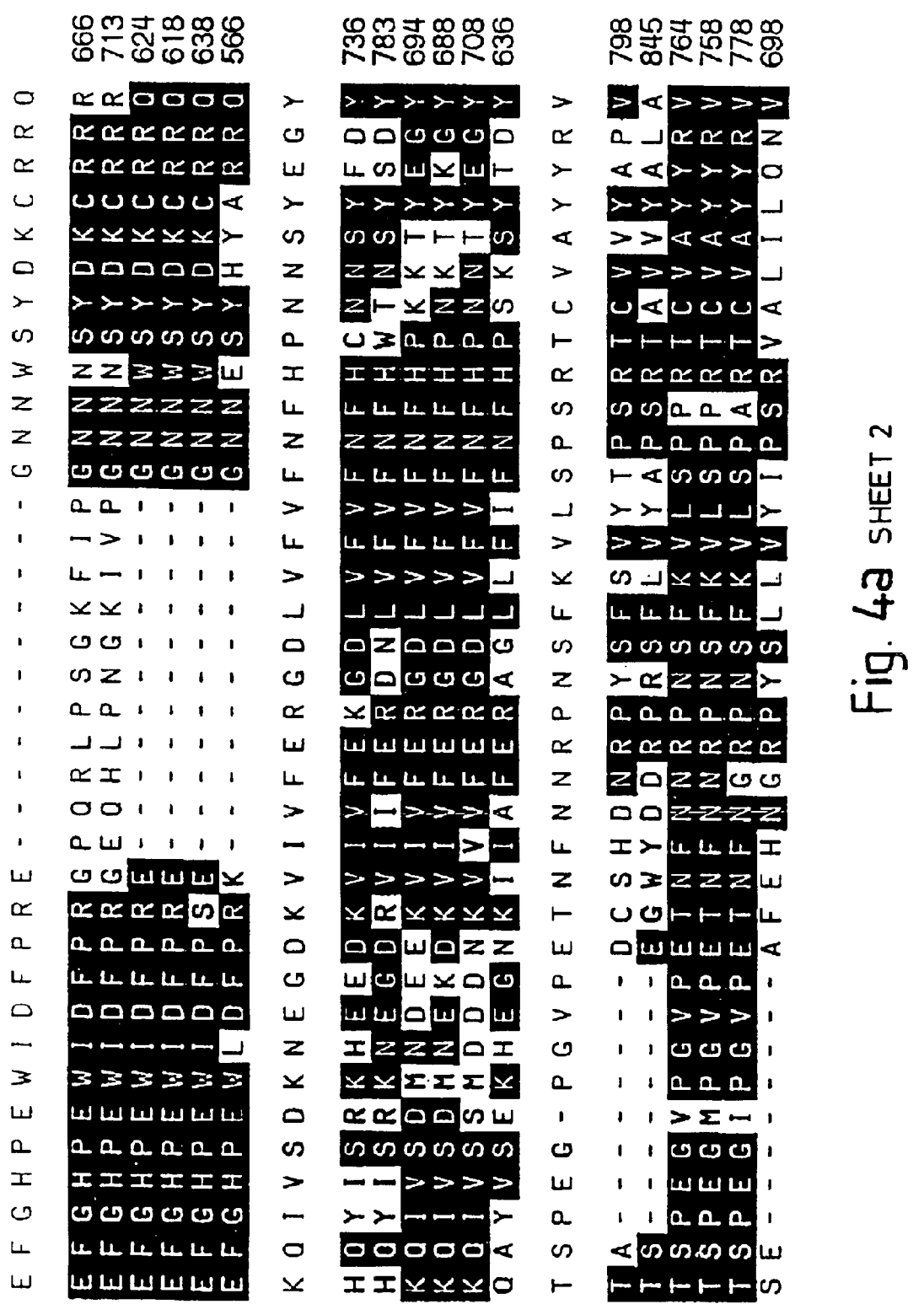
Figure 4B:
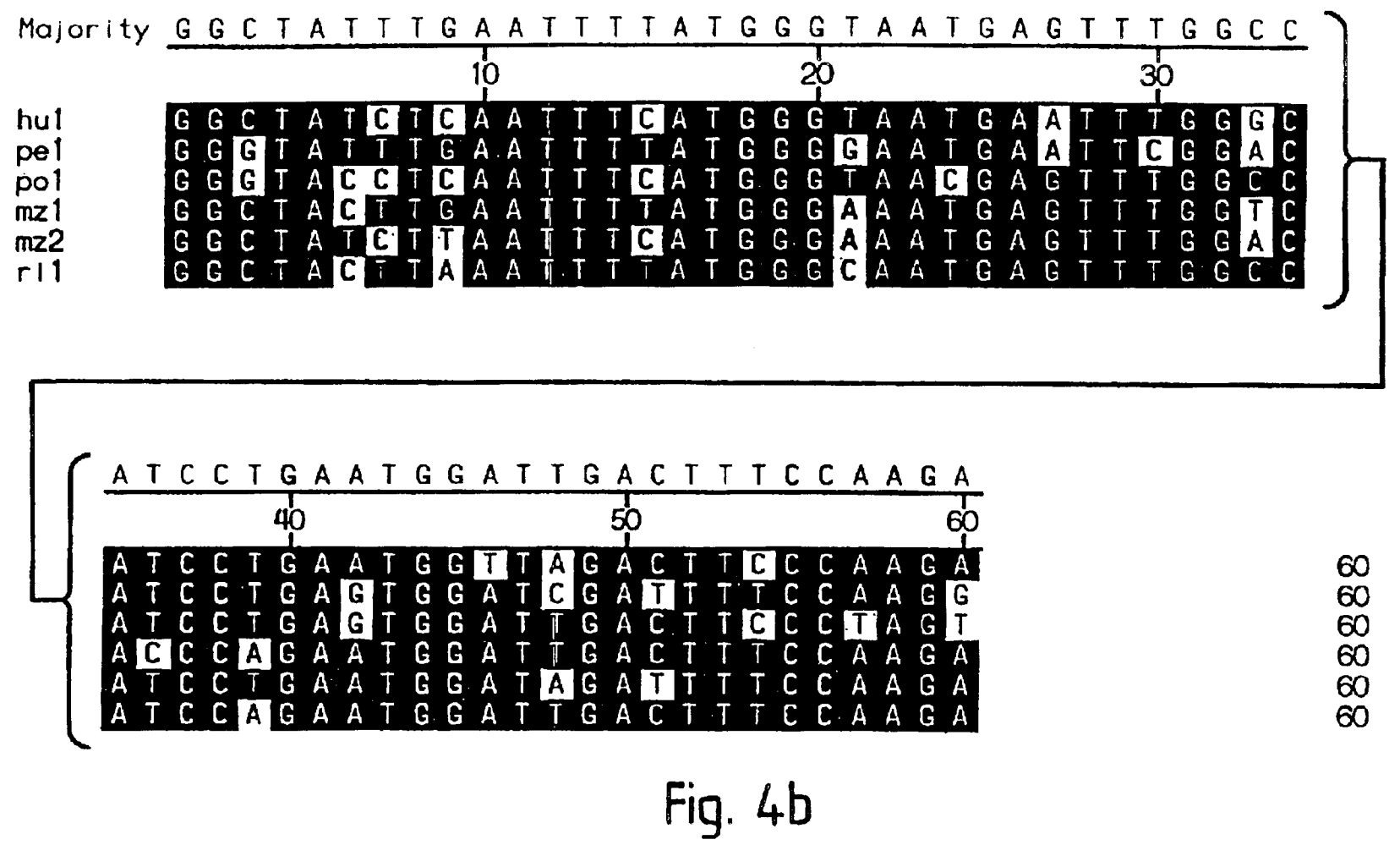

The strategy for cloning the second form of starch branching enzyme from potato is shown in FIG. 3. The small arrowheads represent primers used by the inventors in PCR and RACE protocols. The approximate size of the fragments isolated is indicated by the numerals on the right of the Figure. By way of explanation, a comparison of the amino acid sequences of several cloned plant starch branching enzymes (SBE) from maize (class A), pea (class A), maize (class B), rice (class B) and potato (class B), as well as human glycogen branching enzyme, allowed the inventors to identify a region in the carboxy-terminal one third of the protein which is almost completely conserved (GYLNFMGNEFGHPEWIDFPR, (residues 27–46 of SEQ ID No: 21 in FIG. 4a). A multiple alignment of the DNA sequences (human, pea class A, potato class B, maize class B, maize class A and rice class B, respectively) corresponding to this region is shown in FIG. 4b and was used to design an oligo which would potentially hybridize to all known plant starch branching enzymes: AATTT(C/T)ATGGGIAA(C/T)GA(A/G)TT(C/T)GG (Seq ID No. 20).

Library PCR

The initial isolation of a partial potato class A SBE cDNA clone was from an amplified potato tuber cDNA library in the λZap vector (Stratagene). One half μL of a potato cDNA library (titre 2.3×10$^9$ pfu/mL) was used as template in a 50 μL reaction containing 100 pmol of a 16 fold degenerate POTSBE primer and 25 pmol of a T7 primer (present in the λZap vector 3' to the cDNA sequences—see FIG. 3), 100 μM dNTPs, 2.5 U Taq polymerase and the buffer supplied with the Taq polymerase (Stratagene). All components except the enzyme were added to a 0.5 mL microcentrifuge tube, covered with mineral oil and incubated at 94° C. for 7 minutes and then held at 55° C., while the Taq polymerase was added and mixed by pipetting. PCR was then performed by incubating for 1 min at 94° C., 1 min at 58° C. and 3 minutes at 72° C., for 35 cycles. The PCR products were extracted with phenol/chloroform, ethanol precipitated and resuspended in TE pH 8.0 before cloning into the T/A cloning vector pT7BlueR (Invitrogen).

Several fragments between 600 and 1300 bp were amplified. These were isolated from an agarose gel and cloned into the pT7BlueR T/A cloning vector. Restriction mapping of 24 randomly selected clones showed that they belonged to several different groups (based on size and presence/absence of restriction sites). Initially four clones were chosen for sequencing. Of these four, two were found to correspond to the known potato class B SBE sequence, however the other two, although homologous, differed significantly and were more similar to the pea class A SBE sequence, suggesting that they belonged to the class A family of branching enzymes (Burton et al., 1995 The Plant Journal, cited above). The latter two clones (~800 bp) were sequenced fully. They both contained at the 5' end the sequence corresponding to the degenerate oligonucleotide used in the PCR and had a predicted open reading frame of 192 amino acids. The deduced amino acid sequence was highly homologous to that of the pea class A SBE.

The ~800 bp PCR derived cDNA fragment (corresponding to nucleotides 2281 to 3076 of the psbe2 con.seq sequence shown in FIG. 8) was used as a probe to screen the potato tuber cDNA library. From one hundred and eighty thousand plaques, seven positives were obtained in the primary screen. PCR analysis showed that five of these clones were smaller than the original 800 bp cDNA clone, so these were not analysed further. The two other clones (designated 3.2.1 and 3.1.1) were approximately 1200 and 1500 bp in length respectively. These were sequenced from their 5' ends and the combined consensus sequence aligned with the sequence from the PCR generated clones. The cDNA clone 3.2.1 was excised from the phage vector and plasmid DNA was prepared and the insert fully sequenced. Several attempts to obtain longer clones from the library were unsuccessful, therefore clones containing the 5' end of the full length gene were obtained using RACE (rapid amplification of cDNA ends).

Rapid Amplification of cDNA Ends (RACE) and PCR Conditions

RACE was performed essentially according to Frohman (1992 Amplifications 11–15). Two μg of total RNA from mature potato tubers was heated to 65° C. for 5 min and quick cooled on ice. The RNA was then reverse transcribed in a 20 μL reaction for 1 hour at 37° C. using BRL's M-MLV reverse transcriptase and buffer with 1 mM DTT, 1 mM dNTPs, 1 U/μL RNAsin (Promega) and 500 pmol random hexamers (Pharmacia) as primer. Excess primers were removed on a Centricon 100 column and cDNA was recovered and precipitated with isopropanol. cDNA was A-tailed in a volume of 20 μl using 10 units terminal transferase (BRL), 200 μM dATP for 10 min at 37° C., followed by 5 min at 65° C. The reaction was then diluted to 0.5 ml with TE pH 8 and stored at 4° C. as the cDNA pool. cDNA clones were isolated by PCR amplification using the primers $R_oR_fdT_{17}$, $R_o$ and POTSBE24. The PCR was performed in 50 μL using a hot start technique: 10 μL of the cDNA pool was heated to 94° C. in water for 5 min with 25 pmol POTSBE24, 25 pmol $R_o$ and 2.5 pmol of $R_oR_fdT_{17}$ and cooled to 75° C. Five μL of 10×PCR buffer (Stratagene), 200 μM dNTPs and 1.25 units of Taq polymerase were added, the mixture heated at 45° C. for 2 min and 72° C. for 40 min followed by 35 cycles of 94° C. for 45 sec, 50° C. for 25 sec, 72° C. for 1.5 min and a final incubation at 72° C. for 10 min. PCR products were separated by electrophoresis on 1% low melting agarose gels and the smear covering the range 600–800 bp fragments was excised and used in a second PCR amplification with 25 pmol of $R_I$ and POTSBE25 primers in a 50 µL reaction (28 cycles of 94° C. for 1 min, 50° C. 1 min, 72° C. 2 min). Products were purified by chloroform extraction and cloned into pT7 Blue. PCR was used to screen the colonies and the longest clones were sequenced.

The first round of RACE only extended the length of the SBE sequence approximately 100 bases, therefore a new A-tailed cDNA library was constructed using the class A SBE specific oligo POTSBE24 (10 pmol) in an attempt to recover longer RACE products. The first and second round PCR reactions were performed using new class A SBE primers (POTSBE 28 and 29 respectively) derived from the new sequence data. Conditions were as before except that the elongation step in the first PCR was for 3 min and the second PCR consisted of 28 cycles at 94° C. for 45 seconds, 55° C. for 25 sec and 72° C. for 1 min 45 sec.

Clones ranging in size from 400 bp to 1.4 kb were isolated and sequenced. The combined sequence of the longest RACE products and cDNA clones predicted a full length gene of about 3150 nucleotides, excluding the poly(A) tail (psbe 2con.seq in FIG. 8).

As the sequence of the 5' half of the gene was compiled from the sequence of several RACE products generated using Taq polymerase, it was possible that the compiled sequence did not represent that of a single mRNA species and/or had nucleotide sequence changes. The 5' 1600 bases of the gene was therefore re-isolated by PCR using Ultma, a thermostable DNA polymerase which, because it possesses a 3'-5' exonuclease activity, has a lower error rate compared to Taq polymerase. Several PCR products were cloned and restriction mapped and found to differ in the number of Hind III, Ssp I, and EcoR I sites. These differences do not represent PCR artefacts as they were observed in clones obtained from independent PCR reactions (data not shown) and indicate that there are several forms of the class A SBE gene transcribed in potato tubers.

In order to ensure that the sequence of the full length cDNA clone was derived from a single mRNA species it was therefore necessary to PCR the entire gene in one piece. cDNA was prepared according to the RACE protocol except that the adaptor oligo $R_oR_IdT_{17}$ (5 pmol) was used as a primer and after synthesis the reaction was diluted to 200 µL with TE pH 8 and stored at 4° C. Two µL of the cDNA was used in a PCR reaction of 50 µL using 25 pmol of class A SBE specific primers PBER1 and PBERT (see below), and thirty cycles of 94° for 1 min, 60° C. for 1 min and 72° C. for 3 min. If Taq polymerase was used the PCR products were cloned into pT7Blue whereas if Ultma polymerase was used the PCR products were purified by chloroform extraction, ethanol precipitation and kinased in a volume of 20 µL (and then cloned into pBSSK IIP which had been cut with EcoRV and dephosphorylated). At least four classes of cDNA were isolated, which again differed in the presence or absence of Hind III, Ssp I and EcoR I sites. Three of these clones were sequenced fully, however one clone could not be isolated in sufficient quantity to sequence.

The sequence of one of the clones (number 19) is shown in FIG. 5. The first methionine (initiation) codon starts a short open reading frame (ORF) of 7 amino acids which is out of frame with the next predicted ORF of 882 amino acids which has a molecular mass (Mr) of approximately 100 Kd. Nucleotides 6–2996 correspond to SBE sequence—the rest of the sequence shown is vector derived. FIG. 6 shows a comparison of the most highly conserved part of the amino acid sequence of potato class A SBE (residues 180–871, top, row) and potato class B SBE (bottom row, residues 98–792); the middle row indicates the degree of similarity, identical residues being denoted by the common letter, conservative changes by two dots and neutral changes by a single dot. Dashes indicate gaps introduced to optimise the alignment. The class A SBE protein has 44% identity over the entire length with potato class B SBE, and 56% identity therewith in the central conserved domain (FIG. 6), as judged by the "Megalign" program (DNASTAR). However, FIG. 7 shows a comparison between potato class A SBE (top row, residues 1–873) and pea class A SBE (bottom row, residues 1–861), from which it can be observed that cloned potato gene is more homologous to the class A pea enzyme, where the identity is 70% over nearly the entire length, and this increases to 83% over the central conserved region (starting at IPPP at position ~170). It is clear from this analysis that this cloned potato SBE gene belongs to the class A family of SBE genes.

An *E. coli* culture, containing the plasmid pSJ78 (which directs the expression of a full length potato SBE Class A gene), has been deposited (on 3 Jan. 1996) under the terms of the Budapest Treaty at The National Collections of Industrial and Marine Bacteria Limited (23 St Machar Drive, Aberdeen, AB2 1RY, United Kingdom), under accession number NCIMB 40781. Plasmid pSJ78 is equivalent to clone 19 described above. It represents a full length SBE A cDNA blunt-end ligated into the vector pBSSKIIP.

Polymorphism of Class A SBE Genes

Sequence analysis of the other two full length class A SBE genes showed that they contain frameshift mutations and are therefore unable to encode full length proteins and indeed they were unable to complement the branching enzyme deficiency in the KV832 mutant (described below). An alignment of the full length DNA sequences is shown in FIG. 8: "10con.seq" (Seq ID No. 12), "19con.seq" (residues 1–3012 of SEQ ID No: 14) and "11con.seq" (Seq ID No. 13) represent the sequence of full length clones 10, 19 and 11 obtained by PCR using the PBERI and PBERT primers (see below), whilst "psbe2con.seq" (Seq ID No. 18) represents the consensus sequence of the RACE clones and cDNA clone 3.2.1. Those nucleotides which differ from the overall consensus sequence (not shown) are shaded. Dashes indicate gaps introduced to optimise the alignment. Apart from the frameshift mutations these clones are highly homologous. It should be noted that the 5' sequence of psbe2con is longer because this is the longest RACE product and it also contains several changes compared to the other clones. The upstream methionine codon is still present in this clone but the upstream ORF is shortened to just 3 amino acids and in addition there is a 10 base deletion in the 5' untranslated leader.

The other significant area of variation is in the carboxy terminal region of the protein coding region. Closer examination of this area reveals a GAA trinucleotide repeat structure which varies in length between the four clones. These are typical characteristics of a microsatellite repeat region. The most divergent clone is #11 which has only one GAA triplet whereas clone 19 has eleven perfect repeats and the other two clones have five and seven GAA repeats. All of these deletions maintain the ORF but change the number of glutamic acid residues at the carboxy terminus of the protein.

Most of the other differences between the clones are single base changes. It is quite possible that some of these are PCR errors. To address this question direct sequencing of PCR fragments amplified from first strand cDNA was performed. FIG. 9 shows the DNA sequence, and predicted amino acid sequence, obtained by such direct sequencing.

Certain restriction sites are also marked. Nucleotides which could not be unambiguously assigned are indicated using standard IUPAC notation and, where this uncertainty affects the predicted amino acid sequence, a question mark is used. Sequence at the extreme 5' and 3' ends of the gene could not be determined because of the heterogeneity observed in the different cloned genes in these regions (see previous paragraph). However this can be taken as direct evidence that these differences are real and are not PCR or cloning artefacts.

There is absolutely no evidence for the frameshift mutations in the PCR derived sequence and it would appear that these mutations are an artefact of the cloning process, resulting from negative selection pressure in $E.$ $coli$. This is supported by the fact that it proved extremely difficult to clone the full length PCR products intact as many large deletions were seen and the full length clones obtained were all cloned in one orientation (away from the LacZ promoter), perhaps suggesting that expression of the gene is toxic to the cells. Difficulties of this nature may have been responsible, at least in part, for the previous failure of other researchers to obtain the present invention.

A comparison of all the full length sequences is shown in FIG. 10. In addition to clones 10, 11 and 19 are shown the sequences of a Bgl II—Xho I product cloned directly into the QE32 expression vector ("86CON.SEQ", Seq ID No. 16) and the consensus sequence of the directly sequenced PCR products ("pcrsbe2con.seq", Seq ID No. 17). Those nucleotides which differ from the consensus sequence (not shown) are shaded. Dashes indicate gaps introduced to optimise the alignment. There are 11 nucleotide differences predicted to be present in the mRNA population, which are indicated by asterisks above and below the sequence. The other differences are probably PCR artefacts or possibly sequencing errors.

Complementation of a Branching Enzyme Deficient $E.$ $coli$ Mutant

To determine if the isolated SBE gene encodes an active protein i.e. one that has branching enzyme activity, a complementation test was performed in the $E.$ $coli$ strain KV832. This strain is unable to make bacterial glycogen as the gene for the glycogen branching enzyme has been deleted (Keil et al., 1987 Mol. Gen. Genet. 207, 294–301). When wild type cells are grown in the presence of glucose they synthesise glycogen (a highly branched glucose polymer) which stains a brown colour with iodine, whereas the KV832 cells make only a linear chain glucose polymer which stains bluish green with iodine. To determine if the cloned SBE gene could restore the ability of the KV832 cells to make a branched polymer, the clone pSJ90 (Seq ID No. 19) was used and constructed as below. The construct is a PCR-derived, substantially full length fragment (made using primers PBE 2B and PBE 2X, detailed below), which was cut with Bgl II and Xho I and cloned into the BamH I/Sal I sites of the His-tag expression vector pQE32 (Qiagen). This clone, pSJ86, was sequenced and found to have a frameshift mutation of two bases in the 5' half of the gene. This frameshift was removed by digestion with Nsi I and SnaB I and replaced with the corresponding fragment from a Taq-generated PCR clone to produce the plasmid pSJ90 (sequence shown in FIG. 12; the first 10 amino acids are derived from the expression vector). The polypeptide encoded by pSJ90 would be predicted to correspond to amino acids 46–882 of the full SBE coding sequence. The construct pSJ90 was transformed into the branching enzyme deficient KV832 cells and transformants were grown on solid PYG medium (0.85% $KH_2PO_4$, 1.1% $K_2HPO_4$, 0.6% yeast extract) containing 1.0% glucose. To test for complementation, a loop of cells was scraped off and resuspended in 150 μl of water, to which was added 15 μl Lugol's solution (2 g KI and 1 g $I_2$ per 300 ml water). It was found that the potato SBE fragment-transformed KV832 cells now stained a yellow-brown colour with iodine whereas control cells containing only the pQE32 vector continued to stain blue-green.

Expression of Potato Class A SBE in $E.$ $coli$

Single colonies of KV832, containing one of the plasmids pQE32, pAGCR1 or pSJ90, were picked into 50 ml of 2×YT medium containing carbenicillin, kanamycin and streptomycin as appropriate (100, 50 and 25 mg/L, respectively) in a 250 ml flask and grown for 5 hours, with shaking, at 37° C. IPTG was then added to a final concentration of 1 mM to induce expression and the flasks were further incubated overnight at 25° C. The cells were harvested by centrifugation and resuspended in 50 mM sodium phosphate buffer (pH 8.0), containing 300 mM NaCl, 1 mg/ml lysozyme and 1 mM PMSF and left on ice for 1 hour. The cell lysates were then sonicated (3 pulses of 10 seconds at 40% power using a microprobe) and cleared by centrifugation at 12,000 g for 10 minutes at 4° C. Cleared lysates were concentrated approximately 10 fold in a Centricon™ 30 filtration unit. Duplicate 10 μl samples of the resulting extract were assayed for SBE activity by the phosphorylation stimulation method, as described in International Patent Application No. PCT/GB95/00634.

In brief, the standard assay reaction mixture (0.2 ml) was 200 mM 2-(N-morpholino) ethanesulphonic acid (MES) buffer pH6.5, containing 100 nCi of $^{14}C$ glucose-1-phosphate at 50 mM, 0.05 mg rabbit phosphorylase A, and $E.$ $coli$ lysate. The reaction mixture was incubated for 60 minutes at 30° C. and the reaction terminated and glucan polymer precipitated by the addition of 1 ml of 75% (v/v) methanol, 1% (w/v) potassium hydroxide, and then 0.1 ml glycogen (10 mg/ml). The results are presented below:

| Construct | SBE Activity (cpm) |
| --- | --- |
| pQE32 (control) | 1,829 |
| pSJ90 (potato class A SBE) | 14,327 |
| pAGCR1 (pea class A SBE) | 29,707 |

The potato class A SBE activity is 7–8 fold above background levels. It was concluded therefore that the potato class A SBE gene was able to complement the BE mutation in the phosphorylation stimulation assay and that the cloned gene does indeed code for a protein with branching enzyme activity.

Oligonucleotides

The following synthetic oligonucleotides (Seq ID No.s 1–11 respectively) were used:

$R_0R_1dT_{17}$
AAGGATCCGTCGACATCGATAATACGACTCACTATAGGGA(T)$_{17}$ $R_0$
AAGGATCCGTCGACATC $R_1$
GACATCGATAATACGAC

POTSBE24
CATCCAACCACCATCTCGCA

```
-continued
POTSBE25
TTGAGAGAAGATACCTAAGT

POTSBE28
ATGTTCAGTCCATCTAAAGT

POTSBE29
AGAACAACAATTCCTAGCTC

PBER 1
GGGGCCTTGAACTCAGCAAT

PBERT
CGTCCCAGCATTCGACATAA

PBE 2B
CTTGGATCCTTGAACTCAGCAATTTG

PBE 2X
TAACTCGAGCAACGCGATCACAAGTTCGT
```

Example 2

Production of Transgenic Plants

Figure 11:
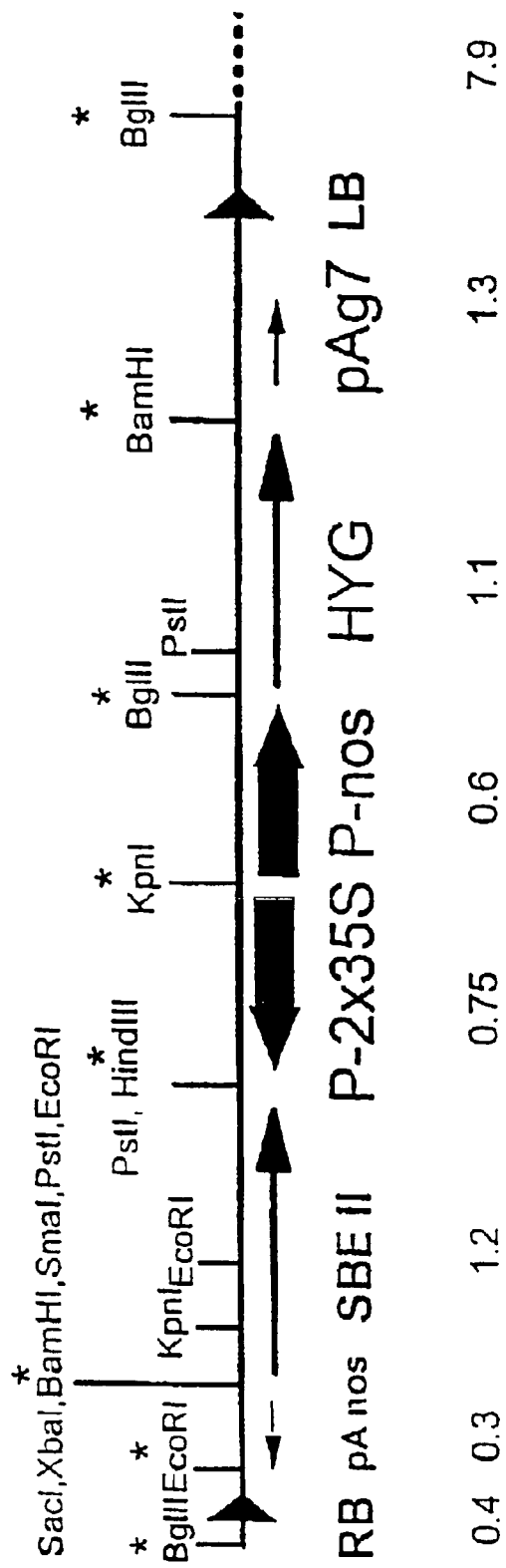
FIG. 11 is a schematic illustration of the plasmid pSJ64.

Construction of Plant Transformation Vectors with Antisense Starch Branching Enzyme Genes A 1200 bp Sac I-Xho I fragment, encoding approximately the —COOH half of the potato class A SBE (isolated from the rescued λZap clone 3.2.1), was cloned into the Sac I—Sal I sites of the plant transformation vector pSJ29 to create plasmid pSJ64, which is illustrated schematically in FIG. 11. In the figure, the black line represents the DNA sequence. The broken line represents the bacterial plasmid backbone (containing the origin of replication and bacterial selection marker), which is not shown in full. The filled triangles on the line denote the T-DNA borders (RB=right border, LB=left border). Relevant restriction sites are shown above the black line, with the approximate distances (in kilobases) between the sites (marked by an asterisk) given by the numerals below the line. The thinnest arrows indicate polyadenylation signals (pAnos=nopaline synthase, pAg7= Agrobacterium gene 7), the arrows intermediate in thickness denote protein coding regions (SBE II=potato class A SBE, HYG=hygromycin resistance gene) and the thickest arrows represent promoter regions (P-2×35=double CaMV 35S promoter, Pnos=nopaline synthase promoter). Thus pSJ64 contained the class A SBE gene fragment in an antisense orientation between the 2×35S CaMV promoter and the nopaline synthase polyadenylation signal.

For information, pSJ29 is a derivative of the binary vector pGPTV-HYG (Becker et al., 1992 Plant Molecular Biology 20, 1195–1197) modified as follows: an approximately 750 bp (Sac I, T4 DNA polymerase blunted—Sal I) fragment of pJIT60 (Guerineau et al., 1992 Plant Mol. Biol. 18, 815–818) containing the duplicated cauliflower mosaic virus (CaMV) 35S promoter (Cabb-JI strain, equivalent to nucleotides 7040 to 7376 duplicated upstream of 7040 to 7433, Frank et al., 1980 Cell 21, 285–294) wa cloned into the Hind III (Klenow polymerase repaired)—Sal I sites of pGPTV-HYG to create pSJ29.

Plant Transformation

Transformation was conducted on two types of potato plant explants; either wild type untransformed minitubers (in order to give single transformants containing the class A antisense construct alone) or minitubers from three tissue culture lines (which gave rise to plants #12, #15, #17 and #18 indicated in Table 1) which had already been successfully transformed with the class B (SBE I) antisense construct containing the tandem 35S promoter (so as to obtain double transformant plants, containing antisense sequences for both the class A and class B enzymes).

Details of the method of Agrobacterium transformation, and of the growth of transformed plants, are described in International Patent Application No. WO 95/26407, except that the medium used contained 3% sucrose (not 1%) until the final transfer and that the initial incubation with Agrobacterium (strain 3850) was performed in darkness. Transformants containing the class A antisense sequence were selected by growth in medium containing 15 mg/L hygromycin (the class A antisense construct comprising the HYG gene, i.e. hygromycin phosphotransferase).

Transformation was confirmed in all cases by production of a DNA fragment from the antisense gene after PCR in the presence of appropriate primers and a crude extract of genomic DNA from each regenerated shoot.

Characterisation of Starch from Potato Plants

Starch was extracted from plants as follows: potato tubers were homogenised in water for 2 minutes in a Waring blender operating at high speed. The homogenate was washed and filtered (initially through 2 mm, then through 1 mm filters) using about 4 liters of water per 100 gms of tubers (6 extractions). Washed starch granules were finally extracted with acetone and air dried.

Starch extracted from singly transformed potato plants (class A/SBE II antisense, or class B/SBE I antisense), or from double transformants (class A/SBE II and class B/SBE I antisense), or from untransformed control plants, was partially characterised. The results are shown in Table 1. The table shows the amount of SBE activity (units/gram tissue) in tubers from each transformed plant. The endotherm peak temperature (° C.) of starch extracted from several plants was determined by DSC, and the onset temperature (° C.) of pasting was determined by reference to a viscoamylograph ("RVA"), as described in WO 95/26407. The viscoamylograph profile was as follows: step 1—50° C. for 2 minutes; step 2—increase in temperature from 50° C. to 95° C. at a rate of 1.5° C. per minute; step 3—holding at 95° C. for 15 minutes; step 4—cooling from 95° C. to 50° C. at a rate of 1.5° C. per minute; and finally, step 5—holding at 50° C. for 15 minutes. Table 1 shows the peak, pasting and set-back viscosities in stirring number units (SNUs), which is a measure of the amount of torque required to stir the suspensions. Peak viscosity may be defined for present purposes as the maximum viscosity attained during the heating phase (step 2) or the holding phase (step 3) of the viscoamylograph. Pasting viscosity may be defined as the viscosity attained by the starch suspensions at the end of the holding phase (step 3) of the viscoamylograph. Set-back viscosity may be defined as the viscosity of the starch suspension at the end of step 5 of the viscoamylograph.

A determination of apparent amylose content (% w/w) was also performed, using the iodometric assay method of Morrison & Laignelet (1983 J. Cereal Sci. 1, 9–20). The results (percentage apparent amylose) are shown in Table 1. The untransformed and transformed control plants gave rise to starches having apparent amylose contents in the range 29(+/−3)%.

Generally similar values for amylose content were obtained for starch extracted from most of the singly transformed plants containing the class A (SBE II) antisense sequence. However, some plants (#152, 249) gave rise to starch having an apparent amylose content of 37–38%, notably higher than the control value. Starch extracted from these plants had markedly elevated pasting onset temperatures, and starch from plant 152 also exhibited an elevated endotherm peak temperature (starch from plant 249 was not tested by DSC).

TABLE 1

| Sample description | Sample. number | Tuber SBE activity (U/g starch) | DSC Peak temperature (° C.) | Viscoamytograph (RVA) | | | | Apparent amylose content (% w/w) | Phosphorus content (mg/100 g) |
|---|---|---|---|---|---|---|---|---|---|
| | | | | Onset temperature (° C.) | Peak viscosity (SNU) | Pasting viscosity (SNU) | Set-back viscosity (SNU) | | |
| Untransformed control | 146 | 7.6 | 65.8 | 65.5 | 545 | 161 | 260 | 31.2 | 68 |
| | 243 | 22.2 | nd | 62.6 | 761 | 135 | 241 | 29.1 | |
| AS-Class A SBE | 152 | 12.7 | 69.5 | 70.9 | 467 | 380 | 529 | 37.5 | 89 |
| | 249 | 13.9 | nd | 70.0 | 497 | 434 | 518 | 38.5 | |
| AS-Class B SBE(17) (control) | 145 | 0.7 | 66.9 | 66.8 | 669 | 177 | 305 | 29.8 | 111 |
| AS-Class B SBE(17) + AS-Class A SBE | 150 | 0.6 | 74.0 | 86.0 | 214 | 214 | 303 | 53.1 | 198 |
| | 161 | 0.5 | 73.0 | 76.6 | 349 | 324 | 618 | 40.9 | 206 |
| AS-Class B SBE(18) (control) | 144 | 1.6 | 64.5 | 64.7 | 714 | 154 | 258 | 29.0 | 97 |
| AS-Class B SBE(18) + AS-Class A SBE | 149 | 3.0 | 68.5 | 69.9 | 474 | 267 | 482 | 35.6 | 127 |
| AS-Class B SBE(15) (control) | 172 | 0.22 | nd | 65.4 | 707 | 167 | 290 | 28.8 | 130 |
| AS-Class B SBE(15) + AS-Class A SBE | 201 | 0.10 | nd | >95 | no peak | 12 | 13 | 66.4 | 210 |
| | 208a | 0.10 | nd | >95 | no peak | 12 | 13 | 66.1 | 210 |
| | 208 | 0.30 | 72.8–80.5 | >95 | no peak | 14 | 19 | 62.8 | 240 |
| | 202 | 0.02 | nd | 89.4 | no peak | 172 | 245 | 57.9 | |
| | 212 | 1.40 | nd | 78.0 | 306 | 296 | 541 | 49.5 | |
| | 220 | 1.40 | nd | 75.8 | 355 | 345 | 593 | 44.1 | |
| AS-Class B SBE(12) (control) | 170 | 0.2 | nd | 66.5 | 768 | 202 | 303 | 27.8 | |
| AS-Class B SBE(12) + AS-Class A SBE | 236 | 0.7 | nd | 95.0 | no peak | 23 | 14 | 60.4 | |
| | 208a | 0.9 | nd | 91.2 | no peak | 139 | 192 | 56.7 | |
| | 236a | 0.8 | nd | 77.8 | 244 | 239 | 450 | 48.2 | |

RVA profile 50° C.(2 min), 50–95° C.(1.5° C./min), 95° C.(15 min), 95–50° C.(1.5° C./min), 50° C.(15 min)
Pasting viscosity (47 min) at end of 50° C.(2 min), 50–95° C.(1.5° C./min), 95° C.(15 min)
Set-back viscosity (92 min) at end of profile
SBE Starch Branching Enzyme
SNU Instrument "Stirring Number Units" (arbitrary units)
nd not determined It should be noted that, even if other single transformants were not to provide starch with an altered amylose/amylopectin ratio, the starch from such plants might still have different properties relative to starch from conventional plants (e.g. different average molecular weight or different amylopectin branching patterns), which might be useful.

Double transformant plants, containing antisense sequences for both the class A and class B enzymes, had greatly reduced SBE activity (units/gm) compared to untransformed plants or single anti-sense class A transformants, (as shown in Table 1). Moreover, certain of the double transformant plants contained starch having very significantly altered properties. For example, starch extracted from plants #201, 202, 208, 208a, 236 and 236a had drastically altered amylose/amylopectin ratios, to the extent that amylose was the main constituent of starch from these plants. The pasting onset temperatures of starch from these plants were also the most greatly increased (by about 25–30° C). Starch from plants such as #150, 161, 212, 220 and 230a represented a range of intermediates, in that such starch displayed a more modest rise in both amylose content and pasting onset temperature. The results would tend to suggest that there is generally a correlation between % amylose content and pasting onset temperature, which is in agreement with the known behaviour of starches from other sources, notably maize.

The marked increase in amylose content obtained by inhibition of class A SBE alone, compared to inhibition of class B SBE alone (see PCT/GB95/00634) might suggest that it would be advantageous to transform plants first with a construct to suppress class A SBE expression (probably, in practice, an antisense construct), select those plants giving rise to starch with the most altered properties, and then to re-transform with a construct to suppress class B SBE expression (again, in practice, probably an antisense construct), so as to maximise the degree of starch modification.

Figure 13:
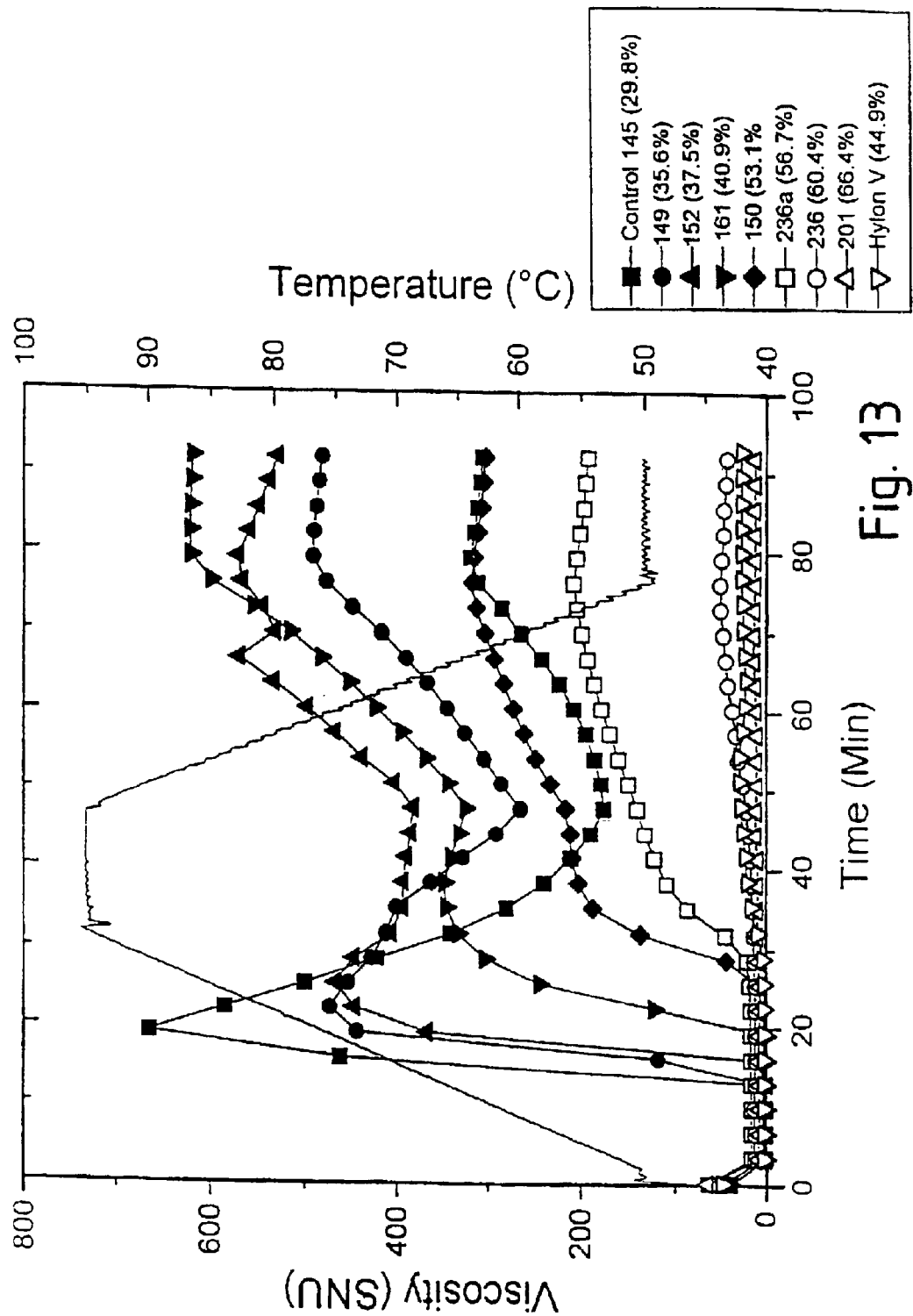
FIG. 13 shows viscoamylographs for 10% w/w suspensions of starch from various transgenic potato plants made by the relevant method aspect of the invention.

In addition to pasting onset temperatures, other features of the viscoamylograph profile e.g. for starches from plants #149, 150, 152, 161, 201, 236 and 236a showed significant differences to starches from control plants, as illustrated in FIG. 13. Referring to FIG. 13, a number of viscoamylograph traces are shown. The legend is as follows: shaded box—normal potato starch control (29.8% amylose content); shaded circle—starch from plant 149 (35.6% amylose); shaded triangle, pointing upwards—plant 152 (37.5%); shaded triangle, pointing downwards—plant 161 (40.9%); shaded diamond—plant 150 (53.1%); unshaded box—plant 236a (56.7%); unshaded circle—plant 236 (60.4%); unshaded triangle, pointing upwards—plant 201 (66.4%); unshaded triangle, pointing downwards—HYLON® V starch, from maize (44.9% amylose). The thin line denotes the heating profile.

With increasing amylose content, peak viscosities during processing to 95° C. decrease, and the drop in viscosity from the peak until the end of the holding period at 95° C. also generally decreases (indeed, for some of the starch samples there is an increase in viscosity during this period). Both of these results are indicative of reduced granule fragmentation, and hence increased granule stability during pasting. This property has not previously been available in potato starch without extensive prior chemical or physical modification. For applications where a maximal viscosity after processing to 95° C. is desirable (i.e. corresponding to the viscosity after 47 minutes in the viscoamylograph test), starch from plant #152 would be selected as starches with both lower (Controls, #149) and higher (#161, #150) amylose contents have lower viscosities following this gelatinization and pasting regime (FIG. 13 and Table 1). It is believed that the viscosity at this stage is determined by a combination of the extent of granule swelling and the resistance of swollen granules to mechanical fragmentation. For any desired viscosity behaviour, one skilled in the art would select a potato starch from a range containing different amylose contents produced according to the invention by performing suitable standard viscosity tests.

Figure 1:
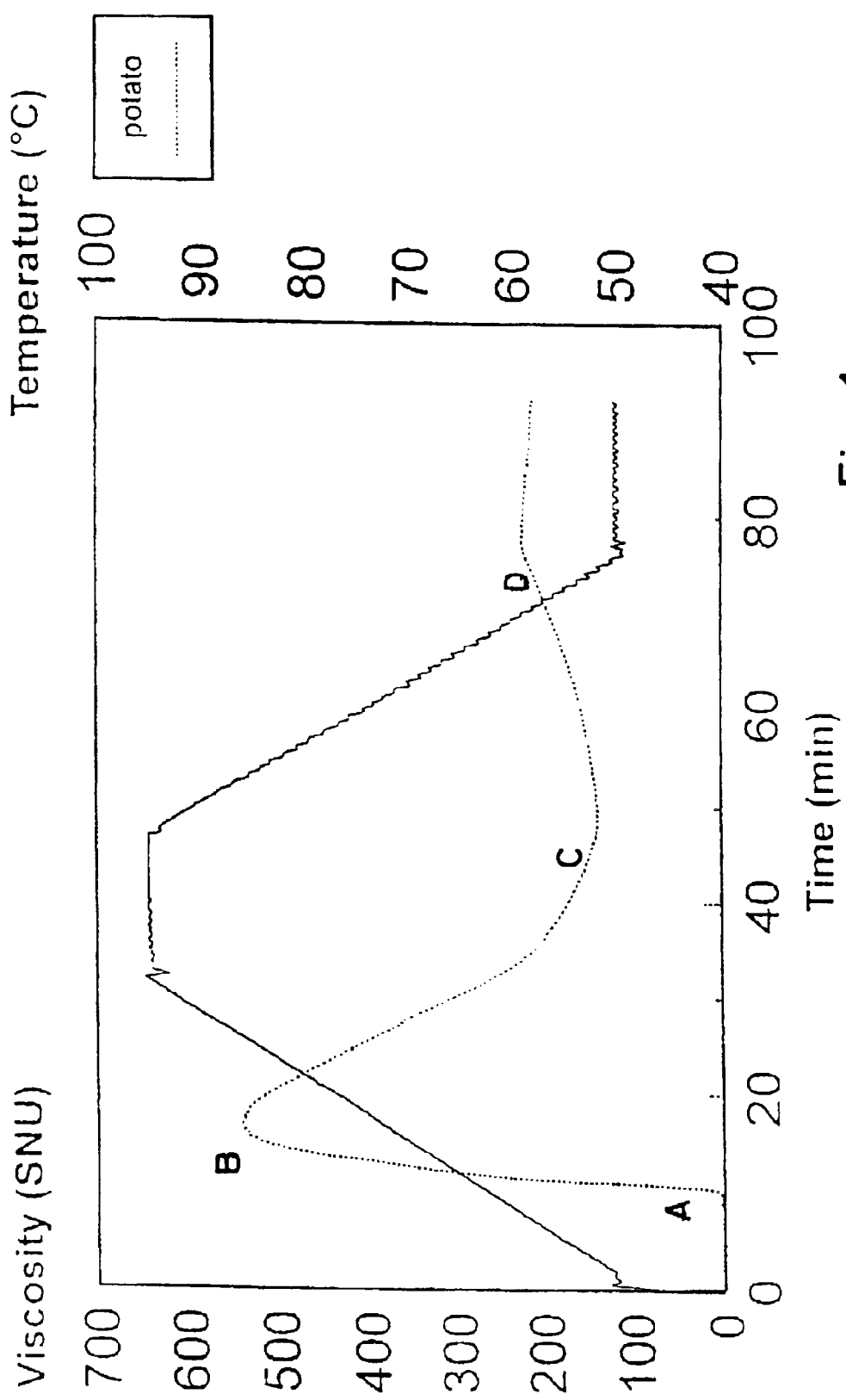
FIG. 1 shows a typical viscoamylograph for a 10% w/w suspension of potato starch.
Figure 2:
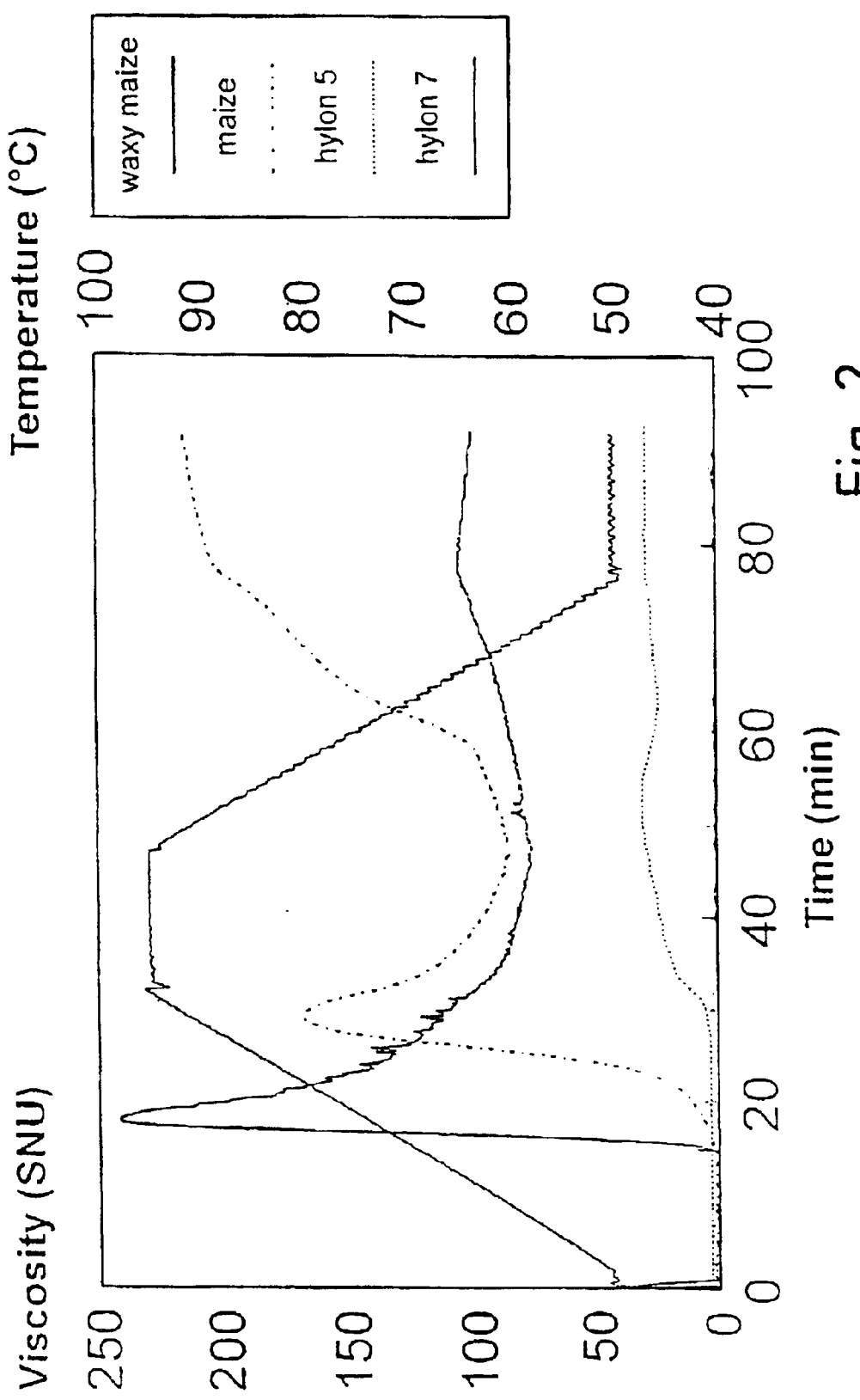
FIG. 2 shows vsicoamylographs for 10% suspensions of starch from various maize varieties.

Upon cooling pastes from 95° C. to 50° C., potato starches from most plants transformed in accordance with the invention showed an increase in viscoamylograph viscosity as expected for partial reassociation of amylose. Starches from plants #149, 152 and 161 all show viscosities at 50° C. significantly in excess of those for starches from control plants (FIG. 13 and Table 1). This contrasts with the effect of elevated amylose contents in starches from maize plants (FIG. 2) which show very low viscosities throughout the viscoamylograph test. Of particular note is the fact that, for similar amylose contents, starch from potato plant 150 (53% amylose) shows markedly increased viscosity compared with HYLON® V starch (44.9% amylose) as illustrated in FIG. 13. This demonstrates that useful properties which require elevated (35% or greater) amylose levels can be obtained by processing starches from potato plants below 100° C., whereas more energy-intensive processing is required in order to generate similarly useful properties from high amylose starches derived from maize plants.

Final viscosity in the viscoamylograph test (set-back viscosity after 92 minutes) is greatest for starch from plant #161 (40.9% amylose) amongst those tested (FIG. 13 and Table 1). Decreasing final viscosities are obtained for starches from plant #152 (37.5% amylose), #149 (35.6% amylose) and #150 (53.1% amylose). Set-back viscosity occurs where amylose molecules, exuded from the starch granule during pasting, start to re-associate outside the granule and form a viscous gel-like substance. It is believed that the set-back viscosity values of starches from transgenic potato plants represent a balance between the inherent amylose content of the starches and the ability of the amylose fraction to be exuded from the granule during pasting and therefore be available for the reassociation process which results in viscosity increase. For starches with low amylose content, increasing the amylose content tends to make more amylose available for re-association, thus increasing the set-back viscosity. However, above a threshold value, increased amylose content is thought to inhibit granule swelling, thus preventing exudation of amylose from the starch granule and reducing the amount of amylose available for re-association. This is supported by the RVA results obtained for the very high amylose content potato starches seen in the viscoamylograph profiles in FIG. 13. For any desired viscosity behaviour following set-back or retrogradation to any desired temperature over any desired timescale, one skilled in the art would select a potato starch from a range containing different amylose contents produced according to the invention by performing standard viscosity tests.

Further experiments with starch from plants #201 and 208 showed that this had an apparent amylose content of over 62% (see Table 1). Viscoamylograph studies showed that starch from these plants had radically altered properties and behaved in a manner similar to HYLON® V starch from maize plants (FIG. 13). Under the conditions employed in the viscoamylograph, this starch exhibited extremely limited (nearly undetectable) granule swelling. Thus, for example, unlike starch from control plants, starch from plants 201, 208 and 208a did not display a clearly defined pasting viscosity peak during the heating phase. Microscopic analysis confirmed that the starch granule structure underwent only minor swelling during the experimental heating process. This property may well be particularly useful in certain applications, as will be apparent to those skilled in the art.

Some re-grown plants have so far been found to increase still further the apparent amylose content of starch extracted therefrom. Such increases may be due to:

i) Growth and development of the first generation transformed plants may have been affected to some degree by the exogenous growth hormones present in the tissue culture system, which exogenous hormones were not present during growth of the second generation plants; and ii) Subsequent generations were grown under field conditions, which may allow for attainment of greater maturity than growth under laboratory conditions, it being generally held that amylose content of potato starch increases with maturity of the potato tuber.

Accordingly, it should be possible to obtain potato plants giving rise to tubers with starch having an amylose content in excess of the 66% level so far attained, simply by analysing a greater number of transformed plants and/or by re-growing transgenic plants through one or more generations under field conditions.

Table 1 shows that another characteristic of starch which is affected by the presence of anti-sense sequences to SBE is the phosphorus content. Starch from untransformed control plants had a phosphorus content of about 60–70 mg/100 gram dry weight (as determined according to the AOAC Official Methods of Analysis, 15th Edition, Method 948.09 "Phosphorus in Flour"). Introduction into the plant of an anti-sense SBE B sequence was found to cause a modest increase (about two-fold) in phosphorus content, which is in agreement with the previous findings reported at scientific meetings. Similarly, anti-sense to SBE A alone causes only a small rise in phosphorus content relative to untransformed controls. However, use of anti-sense to both SBE A and B in combination results in up to a four-fold increase in phosphorus content, which is far greater than any in planta phosphorus content previously demonstrated for potato starch.

This is useful in that, for certain applications, starch must be phosphorylated in vitro by chemical modification. The ability to obtain potato starch which, as extracted from the plant, already has a high phosphorus content will reduce the amount of in vitro phosphorylation required suitably to modify the starch. Thus, in another aspect the invention provides potato starch which, as extracted from the plant, has a phosphorus content in excess of 200 mg/100 gram dry weight starch. Typically the starch will have a phosphorus content in the range 200–240 mg/100 gram dry weight starch.

What is claimed is:

1. An isolated nucleotide sequence, wherein the isolated nucleotide sequence encodes the amino acid sequence of SEQ ID No: 15, or its complement, wherein the isolated nucleotide sequence comprises a 1200 bp fragment of a potato class A starch branching enzyme (SBE) gene.

2. The isolated nucleotide sequence according to claim 1 wherein the nucleotide sequence encodes the amino acid sequence of residues 56 to 889 of SEQ ID No: 15.

3. The isolated nucleotide sequence according to claim 1 comprising the sequence of nucleotides 289 to 2790 of SEQ ID No: 14.

4. The nucleotide sequence according to claim 3, further comprising the sequence of nucleotides 145 to 288 of SEQ ID No: 14.

5. An isolated nucleotide sequence, or its complement, comprising nucleotides 228 to 2855 of the sequence labeled psbe2con.seq in FIG. 8 (nucleotides 272 to 2899 of SEQ ID No: 18).

6. An isolated nucleotide sequence, or its complement comprising the sequence of nucleotides 57 to 2564 of the sequence labeled as psbe2con.seq in FIG. 12 (nucleotides 57 to 2564 of SEQ ID No: 19).

7. The nucleotide sequence according to any one of claims 1 to 6, comprising an in-frame ATG start codon, and optionally including a 5' and/or a 3' untranslated region.

8. The nucleotide sequence according to claim 1, comprising the sequence of nucleotides 45 to 3200 of the sequence labeled as psbe2con.seq in FIG. 8 (nucleotides 1 to 3156 of SEQ ID No: 18).

9. A nucleic acid construct comprising an isolated nucleotide sequence in accordance with claim 1.

10. An expression vector comprising a nucleic acid construct according to claim 9.

11. A host cell into which has been introduced an isolated nucleotide sequence in accordance with claim 1.

12. A method of altering the starch characteristics of a plant, comprising introducing into the plant an isolated nucleotide sequence in accordance with claim 1, operably linked to a suitable promoter active in the plant, so as to affect the expression of a gene present in the plant.

13. The method according to claim 12, wherein the nucleotide sequence is operably linked in the anti-sense orientation to a suitable promoter active in the plant.

14. The method according to claim 12, wherein the introduced sequence comprises at least one region selected from the group consisting of a 5' untranslated region, a 3' untranslated region, and a coding region of the potato class A starch branching enzyme (SBE) operably linked in the sense orientation to a promoter active in the plant, so as to cause sense suppression of an enzyme naturally expressed in the plant.

15. The method according to claim 12, further comprising introducing into the plant one or more further sequences.

16. The method according to claim 15, wherein one or more of the further sequences are operably linked in the anti-sense orientation to a suitable promoter active in the plant.

17. The method according to claim 15, wherein the further sequence comprises a portion of a class B SBE nucleotide sequence.

18. The method according claim 12 or 17, effective in altering the starch composition of a plant.

19. A plant, or the progeny of such a plant, or part of such a plant, or a plant cell each having starch characteristics altered by the method of claim 12 or 17.

20. The plant according to claim 19, selected from the group consisting of potato, pea, tomato, maize, wheat, rice, barley, sweet potato, and cassava.

21. A tuber or other storage organ from a plant according to claim 19.

22. The plant according to claim 19, containing starch which, as extracted from the plant by wet milling at ambient temperature, has an elevated viscosity onset temperature as judged by viscoamylograph compared to starch extracted from a similar, but unaltered, plant, wherein the viscoamylograph is performed at atmospheric pressure using the Newport Scientific Rapid Visco Analyser 3C with a heating profile of holding at 500° C. for 2 minutes, heating from 50° C. to 95° C. at a rate of 1.5° C. per minute, holding at 95° C. for 15 minutes, cooling from 95° C. to 50° C. at a rate of 1.5° C. per minute, and then holding at 50° C. for 15 minutes.

23. The plant according to claim 22, wherein the viscosity onset temperature is elevated by an amount in the range of 10 to 25° C.

24. The plant according to claim 19, containing starch which, as extracted from the plant by wet milling at ambient temperature, has a decreased peak viscosity as judged by viscoamylograph compared to starch extracted from a similar, but unaltered, plant, wherein the viscoamylograph is performed at atmospheric pressure using the Newport Scientific Rapid Visco Analyser 3C with a heating profile of holding at 50° C. for 2 minutes, heating from 50° C. to 95° C. at a rate of 1.5° C. per minute, holding at 95° C. for 15 minutes, cooling from 95 to 50° C. at a rate of 1.5° C. per minute, and then holding at 50° C. for 15 minutes.

25. The plant according to claim 24, wherein the peak viscosity is decreased by an amount in the range of 240 to 700 SNUs.

26. The plant according to claim 19, containing starch which, as extracted from the plant by wet milling at ambient temperature, has an increased pasting viscosity as judged by viscoamylograph compared to starch extracted from a similar, but unaltered, plant, wherein the viscoamylograph is performed at atmospheric pressure using the Newport Scientific Rapid Visco Analyser 3C with a heating profile of holding at 50° C. for 2 minutes, heating from 50° C. to 95° C. at a rate of 1.5° C. per minute, holding at 95° C. for 15 minutes, cooling from 95° C. to 50° C. at a rate of 1.5° C. per minute, and then holding at 50° C. for 15 minutes.

27. The plant according to claim 26, wherein the pasting viscosity is increased by an amount in the range of 37 to 260 SNUs.

28. The plant according to claim 19, containing starch which, as extracted from the plant by wet milling at ambient temperature, has an increased set-back viscosity as judged by viscoamylograph compared to starch extracted from a similar, but unaltered, plant, wherein the viscoamylograph is performed at atmospheric pressure using the Newport Scientific Rapid Visco Analyser 3C with a heating profile of holding at 50° C. for 2 minutes, heating from 50° C. to 95° C. at a rate of 1.5° C. per minute, holding at 95° C. for 15 minutes, cooling from 95° C. to 50° C. at a rate of 1.5° C. per minute, and then holding at 50° C. for 15 minutes.

29. The plant according to claim 28, wherein the set-back viscosity is increased by an amount in the range of 224 to 313 SNUs.

30. The plant according to claim 19, containing starch which, as extracted from the plant by wet milling at ambient temperature, has a decreased set-back viscosity as judged by viscoamylograph compared to starch extracted from a similar, but unaltered, plant, wherein the viscoamylograph is performed at atmospheric pressure using the Newport Scientific Rapid Visco Analyser 3C with a heating profile of holding at 50° C. for 2 minutes, heating from 50° C. to 95°

C. at a rate of 1.5° C. per minute, holding at 95° C. for 15 minutes, cooling from 95° C. to 50° C. at a rate of 1.5° C. per minute, and then holding at 50° C. for 15 minutes.

31. The plant according to claim 19, containing starch which, as extracted from the plant by wet milling at ambient temperature, has an elevated apparent amylose content as judged by iodometric assay according to the method of Morrison & Laignelet, compared to starch extracted from a similar, but unaltered, plant.

32. The plant according to claim 19, containing starch which, as extracted from the plant, has a phosphorus content in excess of 200 mg/ 100 grams dry weight starch.

33. A potato plant or part thereof which, in its wild type possesses an effective SBE A gene, but which plant has been altered such that there is no effective expression of an SBE A polypeptide within the cells of at l,past part of the plant, wherein the alteration is effected by a method according to claim 12 or 17.

34. The nucleotide sequence of claim 7, further comprising a 5' and/or a 3' untranslated region.

* * * * *